(12) United States Patent
Kole et al.

(10) Patent No.: US 11,071,749 B2
(45) Date of Patent: *Jul. 27, 2021

(54) OLIGONUCLEOTIDE ANALOGUES TARGETING HUMAN LMNA

(71) Applicant: SAREPTA THERAPEUTICS, INC., Cambridge, MA (US)

(72) Inventors: Ryszard Kole, Corvallis, OR (US); Richard Keith Bestwick, Corvallis, OR (US)

(73) Assignee: SAREPTA THERAPEUTICS, INC., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/387,002

(22) Filed: Apr. 17, 2019

(65) Prior Publication Data

US 2020/0147119 A1   May 14, 2020

Related U.S. Application Data

(63) Continuation of application No. 16/123,611, filed on Sep. 6, 2018, now abandoned, which is a continuation of application No. 15/595,820, filed on May 15, 2017, now Pat. No. 10,076,536, which is a continuation of application No. 14/709,355, filed on May 11, 2015, now Pat. No. 9,682,097, which is a continuation of application No. 13/708,708, filed on Dec. 7, 2012, now Pat. No. 9,066,967.

(60) Provisional application No. 61/568,590, filed on Dec. 8, 2011.

(51) Int. Cl.
| | |
|---|---|
| A61K 31/713 | (2006.01) |
| A61K 47/64 | (2017.01) |
| C12N 15/11 | (2006.01) |
| C12N 15/113 | (2010.01) |

(52) U.S. Cl.
CPC ........ *A61K 31/713* (2013.01); *A61K 47/6455* (2017.08); *C12N 15/111* (2013.01); *C12N 15/113* (2013.01); *C12N 2310/11* (2013.01); *C12N 2310/314* (2013.01); *C12N 2310/3233* (2013.01); *C12N 2310/3513* (2013.01); *C12N 2320/33* (2013.01)

(58) Field of Classification Search
None
See application file for complete search history.

(56) References Cited

U.S. PATENT DOCUMENTS

| | | |
|---|---|---|
| 4,794,499 A | 12/1988 | Ott |
| 5,034,506 A | 7/1991 | Summerton et al. |
| 5,142,047 A | 8/1992 | Summerton et al. |
| 5,166,315 A | 11/1992 | Summerton et al. |
| 5,185,444 A | 2/1993 | Summerton et al. |
| 5,217,866 A | 6/1993 | Summerton et al. |
| 5,506,337 A | 4/1996 | Summerton et al. |
| 5,521,063 A | 5/1996 | Summerton et al. |
| 5,539,082 A | 7/1996 | Nielsen et al. |
| 5,698,685 A | 12/1997 | Summerton et al. |
| 5,714,331 A | 2/1998 | Buchardt et al. |
| 5,719,262 A | 2/1998 | Buchardt et al. |
| 6,670,461 B1 | 12/2003 | Wengel et al. |
| 6,794,499 B2 | 9/2004 | Wengel et al. |
| 6,969,766 B2 | 11/2005 | Kim et al. |
| 7,022,851 B2 | 4/2006 | Kim et al. |
| 7,034,133 B2 | 4/2006 | Wengel et al. |
| 7,053,207 B2 | 5/2006 | Wengel |
| 7,060,809 B2 | 6/2006 | Wengel et al. |
| 7,084,125 B2 | 8/2006 | Wengel |
| 7,125,994 B2 | 10/2006 | Kim et al. |
| 7,145,006 B2 | 12/2006 | Kim et al. |
| 7,179,896 B2 | 2/2007 | Kim et al. |
| 7,211,668 B2 | 5/2007 | Kim et al. |
| 7,569,575 B2 | 8/2009 | Sorensen et al. |
| 7,572,582 B2 | 8/2009 | Wengel et al. |
| 7,943,462 B1 | 5/2011 | Beyer et al. |
| 7,943,762 B2 | 5/2011 | Weller et al. |
| 8,076,476 B2 | 12/2011 | Reeves et al. |
| 8,258,109 B2 | 9/2012 | Bennett et al. |
| 8,779,128 B2 | 7/2014 | Hanson et al. |
| 9,066,967 B2 | 6/2015 | Kole et al. |
| 9,278,987 B2 | 3/2016 | Hanson et al. |
| 9,326,992 B2 | 5/2016 | Kole et al. |
| 9,682,097 B2 | 6/2017 | Kole et al. |
| 9,833,468 B2 | 12/2017 | Kole et al. |
| 2010/0016215 A1 | 1/2010 | Moutlon et al. |

FOREIGN PATENT DOCUMENTS

| | | |
|---|---|---|
| JP | 2010-532168 A | 10/2010 |
| WO | 2007/047913 A2 | 4/2007 |
| WO | 2008/036127 A2 | 3/2008 |
| WO | 2009/005793 A2 | 1/2009 |
| WO | 2009/064471 A1 | 5/2009 |
| WO | 2009/086469 A2 | 7/2009 |

(Continued)

OTHER PUBLICATIONS

Cao et al. (2011) "Progerin and telomere dysfunction collaborate to trigger cellular senescence in normal human fibroblasts" The Journal of Clinical Investigation 121(7):2833-2844.

Chan et al. (2006) "Antisense Oligonucleotides: From Design to Therapeutic Application," Clinical and Experimental Pharmacology and Physiology 33:533-540.

(Continued)

*Primary Examiner* — Tracy Vivlemore

(74) *Attorney, Agent, or Firm* — Lathrop GPM LLP; Brian C. Trinque

(57) ABSTRACT

Provided are LMNA-targeted antisense oligonucleotides for reducing expression of one or more aberrantly spliced LMNA mRNA isoforms that encode progerin.

12 Claims, 8 Drawing Sheets

Specification includes a Sequence Listing.

(56) References Cited

FOREIGN PATENT DOCUMENTS

| WO | 2010/048586 A1 | 4/2010 |
|---|---|---|
| WO | 2011/060320 A1 | 5/2011 |
| WO | 2011/150408 A2 | 12/2011 |
| WO | 2012/150960 A1 | 11/2012 |

OTHER PUBLICATIONS

Egholm et al. (1993) "PNA hybridizes to complementary oligonucleotides obeying the Watson-Crick hydrogen-bonding rules," Nature 365:566-568.

Fong et al. (2009) "Activating the synthesis of progerin the mutant prelamin A in Hutchinson-Gilford progeria syndrome with antisense oligonucleotides," Human Molecular Genetics 18(13):2462-2471.

Fossel (2000) "Human Aging and Progeria," Journal of Pediatric Endocrinology and Metabolism 13 Suppl. 6:1477-1481.

Gene Tools "What Do We Make?" retrieved from: http://web.archive.org/web/20111105131436/http"//www.gene-tools.com/> retrieved on Aug. 12, 2016 2 pages.

Gonzalez et al. (2011) "A-type lamins and Hutchinson-Gilford progeria syndrome: pathogenesis and therapy," Frontiers in Bioscience S3:1133-1146.

Gregory et al. "*Homo sapiens* chromosome 1 GRCh37.P5 Primary Assembly," GenBank Online Accession No. NC_000001.10, Jul. 29, 2011 retrieved from: http://www.ncbi.nlm.nih.gov/nuccore/NC_000001.10?report=gbwithparts &log $=se qview&sat=16&satkey=3691223&from =156082546&to=156140089>, retrieved on Aug. 9, 2016 21, pages.

Hammond et al. (2011) "Genetic therapies for RNA mis-splicing diseases," Trends in Genetics 27(5):196-205.

Hayflick. (1976) "The cell biology of human aging," The New England Journal of Medicine 295(23):1302-1308.

Huang et al. (2005) "Correction of cellular phenotypes of Hutchinson-Gilford Progeria cells by RNA interference," Human Genetics 118:444-450.

Kinali et al. (2009) "Local restoration of dystrophin expression with the morpholino oligomer AVI-4658 in Duchenne muscular dystrophy: a single-blind placebo-controlled dose-escalation proof-of-concept study," Lancet Neurol 8:918-928.

Koshimizu et al. (2011) "Embryonic Senescence and Laminopathies in a Progeroid Zebrafish Model," PLoS ONE 6(3):e17688,17 pages.

Ly et al. (2000) "Mitotic Misregulation and Human Aging," Science 287:2486-2492.

Nelson et al. (2005) "Arginine-Rich Peptide Conjugation to Morpholino Oligomers: Effects on Antisense Activity and Specificity," Bioconjugate Chem 16:959-966.

Nielsen et al. (1991) "Sequence-Selective Recognition of DNA by Strand Displacement with a Thymine-Substituted Polyamide," Science 254:1497-1500.

Obika et al. (1997) "Synthesis of 2'-0,4'-C-Methyleneuridine and -cytidine. Novel Bicyclic Nucleosides Having a Fixed C3-endo Sugar Puckering," Tetrahedron Letters 38(50):8735-8738.

Okiba et al. (1998) "Stability and structural features of the duplexes containing nucleoside analogues with a fized N-type conformation, 2'),4'-C-methyleneribonucleosides," Tetrahedron Letters 39:5401:5404.

Obika et al. (2008) "Synthesis and properties of 3'-amino-2'4'-BNA a bridged nucleic acid with a N3'→P5' phosphoramidate linkage," Bioorganic & Medicinal Chemistry 16:9230-9237.

Osorio et al. (2011) "Splicing-Directed Therapy in a New Mouse Model of Human Accelerated Aging," Science Translation Medicine 3(103-106):145-155.

Pereira et al. (2008) "HGPS and related premature aging disorders: From genomic identification to the first therapeutic approaches," Mechanisms of Ageing and Development 129:449-459.

Scaffidi et al. (2005) "Reversal of the cellular phenotype in the premature aging disease Hutchinson-Gilford progeria syndrome," Nature Medicine 11(4):440-445.

Serio. (2011) "Unraveling the Mysteries of Aging Through a Hutchinson-Gilford Progeria Syndrome Model," Rejuvenation Research 14(2):133-141.

Singh et al. (1998) "LNA (locked nucleic acids): synthesis and high-affinity nucleic acid recognition," Chem Commun 455-456.

Svasti et al. (2009) "RNA repair restores hemoglobin expression in IVS2-654 thalassemic mice," PNAS 106(4): 1205-1210.

Uhlmann et al. (1990) "Antisense Oligonucleotides: A New Therapeutic Principle," Chemical Reviews 90(4):543-584.

Wengel. (1999) "Synthesis of 3'-C- and 4'-C-Branched Oligodeoxynucleotides and the Development of Locked Nucleic Acid (LNA)," Accounts of Chemical Research 32(4):301-310.

International Search Report dated Jun. 20, 2013 for international Application No. PCT/US2012/068606, 9 pages.

International Search Report dated Jun. 20, 2013 for International Application No. PCT/US2012/068609 9 pages.

Written Opinion of the International Searching Authority dated Jun. 20, 2013 for international Application No. PCT/US2012/068606, 11 pages.

Written Opinion of the International Searching Authority dated Jun. 20, 2013 for international Application No. PCT/US2012/068609 12 pages.

"Clarification of condition of progeria, national study group of which purpose is to establish and familiarize diagnosis/therapy method, progeria," Japan Intractable Diseases Information Center [online]; 2013, Japan Intractable Diseases (Nanbyo) Research Foundation [retrieved on Nov. 28, 2018], Internet: <URL:http://www.nanbyou.or.jp/kenkyuhan_pdf2013/s-sitei5.pdf>.

| SS#/510 ID No. | Intensity Mean (gray, @50nM) | |
|---|---|---|
| | Lamin A/C (%) | Progerin (%) |
| None | 100.000 | 100.000 |
| 711/16 | *61.786 | *59.663 |
| 709/14 | 108.805 | *64.186 |
| 705/10 | *108.207 | *67.607 |
| 699/4 | *87.305 | *75.803 |
| 706/11 | *115.919 | *79.194 |
| 708/13 | 85.908 | *82.588 |
| 700/5 | 91.136 | *82.817 |
| 698/3 | *77.241 | 89.421 |
| 707/12 | *90.455 | 92.44 |
| 702/7 | *111.877 | 95.114 |
| 703/8 | *116.475 | 104.998 |
| 701/6 | 96.477 | 106.397 |
| 704/9 | *136.971 | 111.343 |
| 710/15 | 99.673 | *123.422 |

* significant change (p < 0.05)

FIG. 2

OLIGONUCLEOTIDE ANALOGUES TARGETING HUMAN LMNA

CROSS REFERENCE TO RELATED APPLICATIONS

This application is U.S. application Ser. No. 16/387,002, filed Apr. 17, 2019, which is a continuation of U.S. application Ser. No. 16/123,611, filed Sep. 6, 2018, now abandoned, which is a continuation of U.S. application Ser. No. 15/595,820, filed May 15, 2017, now issued as U.S. Pat. No. 10,076,536, which is a continuation of U.S. application Ser. No. 14/709,355, filed May 11, 2015 now issued as U.S. Pat. No. 9,682,097 on Jun. 20, 2017, which is a continuation of U.S. application Ser. No. 13/708,708, filed Dec. 7, 2012 now issued as U.S. Pat. No. 9,066,967 on Jun. 30, 2015; which claims the benefit under 35 U.S.C. § 119(e) of U.S. Provisional Patent Application No. 61/568,590, filed Dec. 8, 2011; each of which is incorporated by reference in its entirety.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 605184-SPT-8106ACON4-SEQUENCE-LISTING.txt. The text file is about 15.6 KB, was created on Feb. 1, 2020, and is being submitted electronically via EFS web.

TECHNICAL FIELD

The present invention relates generally to human lamin A targeted antisense compounds.

DESCRIPTION OF THE RELATED ART

Hutchinson-Gilford progeria syndrome (HGPS) is a rare genetic disorder characterized by premature arteriosclerosis and degeneration of vascular smooth muscle cells (SMCs). HGPS manifests itself most notably as accelerated, premature aging in affected children. Children with HGPS have progressive symptoms such as growth retardation, alopecia, loss of subcutaneous fat, and bone abnormalities. Average lifespan is 12 years with the most common cause of death being myocardial infarction or stroke.

Most HGPS cases are caused by a single-point mutation in the lamin A (LMNA) gene, resulting in the generation of progerin, a truncated splicing mutant of lamin A. The single-point mutation is a de novo silent substitution (1824C>T, Gly608Gly) in exon 11 of the lamin A (LMNA) gene. The substitution activates a cryptic splice donor site, which leads to the production of a dominant negative mutant lamin A protein with an internal deletion of 50 amino acids. The mutant protein, named progerin, accumulates on the nuclear membrane, causing characteristic nuclear blebbing ((Scaffidi and Misteli 2005; Cao, Blair et al. 2011)).

It is known that aberrant splicing can be corrected using phosphorodiamidate morpholino oligonucleotides (PMOs), or more specifically, splice-switching oligonucleotides (SSOs). SSOs block aberrant splicing sites by hybridizing at or near the sites thereby preventing recognition by the cellular splicing machinery. Preferred SSOs are resistant to nucleases and the resulting double-stranded structure eliminates the possibility of RNA cleavage by RNase H. SSOs have been shown to effectively repair the splicing pattern both in vitro and in vivo for thalassemia and Duchenne muscular dystrophy. (Kinali, Arechavala-Gomeza et al. 2009; Svasti, Suwanmanee et al. 2009). The aberrant splicing of LMNA associated with HGPS has been shown to be reduced by correction of the aberrant splicing event using modified antisense oligonucleotides targeted to the activated cryptic splice site both in cell culture (Scaffidi and Misteli 2005) and in a relevant animal model (Osorio, Navarro et al. 2011).

Given the role of LMNA in HGPS, oligonucleotides that modulate splicing of LMNA pre-mRNA to eliminate expression of progerin are needed.

BRIEF SUMMARY

Embodiments of the present invention relate generally to compositions that modulate aberrant splicing of LMNA pre-mRNA. For example, according to one embodiment, there are provided antisense oligonucleotides for use in modulating aberrant splicing of a human LMNA pre-mRNA, the oligonucleotides being composed of morpholino subunits and phosphorus-containing intersubunit linkages joining a morpholino nitrogen of one subunit to a 5'-exocyclic carbon of an adjacent subunit, and:

(i) having a substantially uncharged, nuclease resistant backbone;

(ii) capable of uptake by mammalian host cells;

(iii) containing between about 12-40 nucleotide bases; and (iv) having a targeting sequence of at least about 12 contiguous subunits complementary to exon 10, intron 10, exon 11, or combinations thereof of a human LMNA pre-mRNA.

In more specific embodiments, the targeting sequence of the oligonucleotide is complementary to bases upstream of the exon 11 cryptic splice site of a human LMNA pre-mRNA. In other specific embodiments, the targeting sequence is complementary to bases downstream of the exon 11 cryptic splice site of a human LMNA pre-mRNA. In still other specific embodiments, the targeting sequence does not overlap the exon 11 cryptic splice site of the human LMNA pre-mRNA.

In additional embodiments, the targeting sequence in the oligonucleotide used in the methods of the invention does not overlap with the 1824C>T mutation.

In another specific embodiment, the 3'-most base of the targeting sequence is complementary to a base in LMNA exon 11 that is about 1-30 bases downstream of the exon 11 cryptic splice site of a human LMNA pre-mRNA.

In another specific embodiment, the 3'-most base of the targeting sequence is complementary to a base in LMNA exon 11 that is about 1-30 bases downstream of the exon 11 cryptic splice site of a human LMNA pre-mRNA.

In yet another specific embodiment, the 3'-most base of the targeting sequence is complementary to a base in LMNA exon 11 that is about 10-40 bases upstream of the exon 11 cryptic splice site of a human LMNA pre-mRNA.

In still another specific embodiment, the 3'-most base of the targeting sequence is complementary to a base in LMNA intron 10 that is about 1-60 bases upstream of LMNA exon 11.

In another specific embodiment, the 3'-most base of the targeting sequence is complementary to a base in LMNA exon 10 that is about 1-30 bases upstream of LMNA intron 10.

In still another specific embodiment, the targeting sequence is complementary to a region that overlaps the splice junction of splice donor (SD) or splice acceptor (SA) sites of exons 10 and 11 of LMNA pre-mRNA, and is complementary to a portion of an exonic region and a portion of an intronic region of the pre-processed mRNA.

The targeting sequence of the oligonucleotide, in even more specific embodiments of the invention, is complementary to at least 12 contiguous bases of any one of SEQ ID NOs: 3-34, or is at least 90% identical to any one of SEQ ID NOs 3-34, or comprises any one of SEQ ID NOs: 3-34, or consists of any one of SEQ ID NOs: 3-34.

The targeting sequence of the oligonucleotide, in even more specific embodiments of the invention, is complementary to at least 12 contiguous bases of any one of SEQ ID NOs: 3-7 or 14-16, or is at least 90% identical to any one of SEQ ID NOs: 3-7 or 14-16, or comprises any one of SEQ ID NOs: 3-7 or 14-16, or consists of any one of SEQ ID NOs: 3-7 or 14-16.

The targeting sequence of the oligonucleotide, in even more specific embodiments of the invention, is complementary to at least 12 contiguous bases of SEQ ID NO: 4, or is at least 90% identical to SEQ ID NO: 4, or comprises SEQ ID NO: 4, or consists of SEQ ID NO: 4.

The targeting sequence of the oligonucleotide, in other more specific embodiments of the invention, is complementary to at least 12 contiguous bases of SEQ ID NO: 11, or is at least 90% identical to SEQ ID NO: 11, or comprises SEQ ID NO: 11, or consists of SEQ ID NO: 11.

In other embodiments, the oligonucleotide is a phosphorodiamidate morpholino oligonucleotide (PMO), or a PMO comprising one or more piperazine-containing intersubunit linkages (PMOplus), or a PMO-X oligonucleotide.

Exemplary morpholino subunits, according to certain embodiments of the invention, are joined by phosphorodiamidate linkages, in accordance with the following structure:

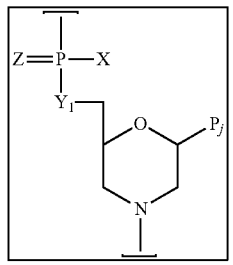

wherein Z is S or O,
X=$NR^1R^2$ or $OR^6$,
Y=O or $NR^7$,
and each said linkage is selected from:
(a) uncharged linkage (a), wherein each of $R^1$, $R^2$, $R^6$, and $R^7$ is independently selected from hydrogen and lower alkyl;
(b1) cationic linkage (b1), wherein X=$NR^1R^2$ and Y=O, and $NR^1R^2$ represents an optional substituted piperazino group, such that $R^1R^2$=
—CHRCHRN($R^3$)($R^4$)CHRCHR—, wherein
each $R^4$ is H, $CH_3$ or null, and
R3 is selected from H, lower alkyl, C(=NH)$NH_2$, Z-L-NHC(=NH)$NH_2$, and
[C(O)CHR'NH]$_m$H, wherein where Z is carbonyl (C(O)) or a direct bond, L is an optional linker up to 18 atoms in length having bonds selected from alkyl, alkoxy, and alkylamino, R' is a side chain of a naturally occurring amino acid or a one- or two-carbon homolog thereof, and m is 1 to 6;
(b2) cationic linkage (b2), wherein X=$NR^1R^2$ and Y=O, $R^1$=H or $CH_3$, and $R^2$=$LNR^3R^4R^5$, wherein L, $R^3$, and $R^4$ are defined as above, and $R^5$ is H, lower alkyl, or lower (alkoxy)alkyl; and
(b3) cationic linkage (b3), wherein Y=$NR^7$ and X=$OR^6$, and R7=$LNR^3R^4R^5$. wherein L, $R^3$, and $R^4$ and $R^5$ are defined as above, and $R^6$ is H or lower alkyl; and at least one said linkage is selected from cationic linkages (b1), (b2), and (b3).

In a more specific embodiment of the structure above, each of $R^1$ and $R^2$, in linkages of type (a), is methyl.

In another specific embodiment of the structure above, at least one linkage is of type (b1), where each R is H, $R^4$ is H, $CH_3$, or an electron pair, and $R^3$ is selected from H, $CH_3$, C(=NH)$NH_2$, and C(O)-L-NHC(=NH)$NH_2$.

In another specific embodiment of the structure above, at least one linkage is of type (b1), where each R is H, $R^4$ is an electron pair, and $R^3$ is selected from C(=NH)$NH_2$ and C(O)-L-NHC(=NH)$NH_2$.

In still another specific embodiment of the structure above, at least one linkage is of type (b1), where each R is H, $R^4$ is an electron pair, and $R^3$ is selected from C(=NH)$NH_2$ and C(O)-L-NHC(=NH)$NH_2$.

In yet another specific embodiment of the structure above, $R^3$ is C(O)-L-NHC(NH)NH2, and L is a hydrocarbon having the structure —$(CH_2)_n$—, where n is 1 to 12.

In another specific embodiment of the structure above, at least one linkage is of type (b1), where each R is H, and each of $R^3$ and $R^4$ is independently H or $CH_3$.

In other embodiments of the invention, the antisense oligonucleotide is covalently attached to a cell-penetrating peptide, such as an arginine-rich peptide. In a more specific embodiment, the arginine-rich peptide is attached at its C-terminus to the 5' end of the oligonucleotide through a one- or two-amino acid linker. Alternatively, in another embodiment, the peptide is attached at its C-terminus to the 3' end of the oligonucleotide through a one- or two-amino acid linker. In a preferred embodiment the cell-penetrating peptide is linked to the oligonucleotide through a glycine amino acid.

In additional embodiments of the invention, there is provided an oligonucleotide comprising a backbone, the backbone comprising a sequence of morpholino ring structures joined by intersubunit linkages, the intersubunit linkages joining a 3'-end of one morpholino ring structure to a 5'-end of an adjacent morpholino ring structure, wherein each morpholino ring structure is bound to a base-pairing moiety, such that the oligonucleotide can bind in a sequence-specific manner to a target nucleic acid, comprising a targeting sequence that is complementary to at least 12 bases of a sequence set forth in any one of SEQ ID NOs: 1-34, or which comprises any one or more of SEQ ID NOs: 3-34, wherein the intersubunit linkages have the following general structure (I):

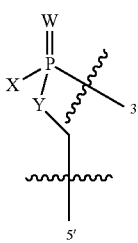

or a salt or isomer thereof, and wherein each of the intersubunit linkages (I) are independently linkage (A) or linkage (B):

wherein for linkage (A):
W is, at each occurrence, independently S or O;
X is, at each occurrence, independently —N(CH$_3$)$_2$, —NR$^1$R$^2$, —OR$^3$ or;

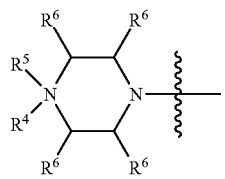
(II)

Y is, at each occurrence, independently O or —NR$^2$,
R$^1$ is, at each occurrence, independently hydrogen or methyl;
R$^2$ is, at each occurrence, independently hydrogen or -LNR$^4$R$^5$R$^7$;
R$^3$ is, at each occurrence, independently hydrogen or C$_1$-C$_6$ alkyl;
R$^4$ is, at each occurrence, independently hydrogen, C$_1$-C$_6$ alkyl, —C(=NH)NH$_2$, —Z-L-NHC(=NH)NH$_2$ or —[C(O)CHR'NH]$_m$H, where Z is carbonyl (C(O)) or a direct bond, R' is a side chain of a naturally occurring amino acid or a one- or two-carbon homolog thereof, and m is 1 to 6;
R$^5$ is, at each occurrence, independently hydrogen, methyl or an electron pair;
R$^6$ is, at each occurrence, independently hydrogen or methyl;
R$^7$ is, at each occurrence, independently hydrogen C$_1$-C$_6$ alkyl or C$_1$-C$_6$ alkoxyalkyl;
L is an optional linker up to 18 atoms in length comprising alkyl, alkoxy or alkylamino groups, or combinations thereof; and wherein for linkage (B):
W is, at each occurrence, independently S or O;
X is, at each occurrence, independently —NR$^8$R$^9$ or —OR$^3$; and
Y is, at each occurrence, independently O or —NR$^{10}$,
R$^8$ is, at each occurrence, independently hydrogen or C$_2$-C$_{12}$ alkyl;
R$^9$ is, at each occurrence, independently hydrogen, C$_1$-C$_{12}$ alkyl, C$_1$-C$_{12}$ aralkyl or aryl;
R$^{10}$ is, at each occurrence, independently hydrogen, C$_1$-C$_{12}$ alkyl or -LNR$^4$R$^5$R$^7$;
wherein R$^8$ and R$^9$ may join to form a 5-18 membered mono or bicyclic heterocycle or R$^8$, R$^9$ or R$^3$ may join with R$^{10}$ to form a 5-7 membered heterocycle, and wherein when X is 4-piparazino, X has the following structure (III):

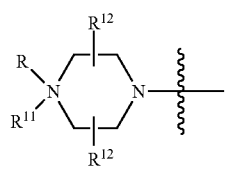
(III)

wherein:
R$^{11}$ is, at each occurrence, independently C$_2$-C$_{12}$ alkyl, C$_1$-C$_{12}$ aminoalkyl, C$_1$-C$_{12}$ alkylcarbonyl, aryl, heteroaryl or heterocyclyl; and
R is, at each occurrence, independently an electron pair, hydrogen or C$_1$-C$_{12}$ alkyl; and
R$^{12}$ is, at each occurrence, independently, hydrogen, C$_1$-C$_{12}$ alkyl, C$_1$-C$_{12}$ aminoalkyl, —NH$_2$, —NR$^{13}$R$^{14}$, —NR$^{13}$R$^{14}$R$^{15}$, C$_1$-C$_{12}$ alkylcarbonyl, oxo, —CN, trifluoromethyl, amidyl, amidinyl, amidinylalkyl, amidinylalkylcarbonyl guanidinyl, guanidinylalkyl, guanidinylalkylcarbonyl, cholate, deoxycholate, aryl, heteroaryl, heterocycle, —SR$^{13}$ or C$_1$-C$_{12}$ alkoxy, wherein R$^{13}$, R$^{14}$ and R$^{15}$ are, at each occurrence, independently C$_1$-C$_{12}$ alkyl; and wherein at least one of the intersubunit linkages is linkage (B).

In some embodiments of the structure above, at least 5% of the intersubunit linkages are linkage (B). In a related embodiment, 10% to 50% of the intersubunit linkages are linkages (B). In another related embodiment, each linkage (B) has the same structure at each occurrence. In yet another specific embodiment of the structure above, each Y and each W are O.

Still other embodiments of the invention provide an antisense oligonucleotide comprising a targeting sequence that is complementary to one or more bases of exon 10 or exon 11 in the human LMNA gene and that contains at least 12 contiguous bases complementary to a sequence set forth in any one of SEQ ID NOs: 3-34.

Further embodiments of the invention provide an antisense oligonucleotide comprising a backbone, the backbone comprising a sequence of morpholino ring structures joined by intersubunit linkages of type (A), (B), or combinations thereof, wherein each morpholino ring structure supports a base-pairing moiety, such that the oligonucleotide compound can bind in a sequence-specific manner to a target nucleic acid, comprising a target sequence that is complementary to at least 12 bases of SEQ ID NOs: 1-34, or which comprises any one or more of SEQ ID NOs:3-34, and wherein the oligonucleotide comprises a 3' terminus, a 5' terminus and has the following structure (XVII):

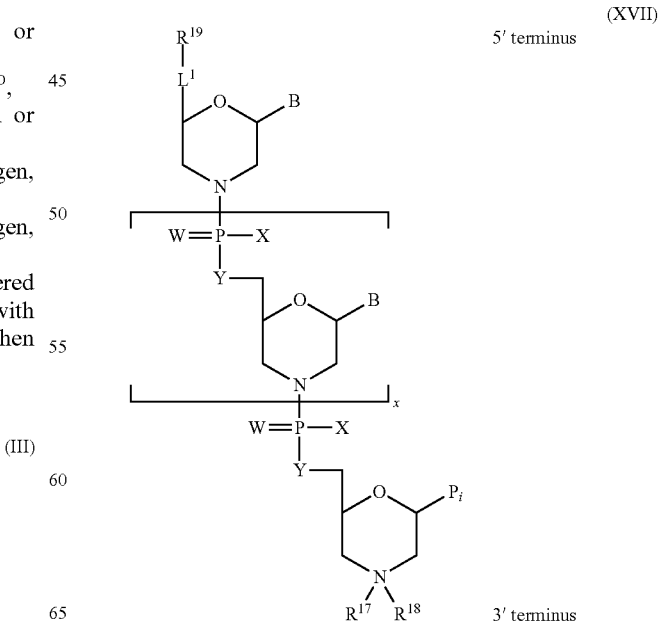
(XVII)

or a salt or isomer thereof, and
wherein for linkage (A):
W is, at each occurrence, independently S or O;
X is, at each occurrence, independently —N(CH$_3$)$_2$, —NR$^1$R$^2$, —OR$^3$ or;

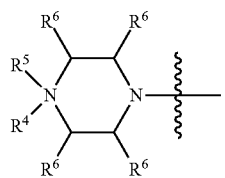
(II)

Y is, at each occurrence, independently O or —NR$^2$,
R$^1$ is, at each occurrence, independently hydrogen or methyl;
R$^2$ is, at each occurrence, independently hydrogen or -LNR$^4$R$^5$R$^7$;
R$^3$ is, at each occurrence, independently hydrogen or C$_1$-C$_6$ alkyl;
R$^4$ is, at each occurrence, independently hydrogen, methyl, —C(=NH)NH$_2$, —Z-L-NHC(=NH)NH$_2$ or —[C(O)CHR'NH]$_m$H, where Z is carbonyl (C(O)) or a direct bond, R' is a side chain of a naturally occurring amino acid or a one- or two-carbon homolog thereof, and m is 1 to 6;
R$^5$ is, at each occurrence, independently hydrogen, methyl or an electron pair;
R$^6$ is, at each occurrence, independently hydrogen or methyl;
R$^7$ is, at each occurrence, independently hydrogen C$_1$-C$_6$ alkyl or C$_1$-C$_6$ alkoxyalkyl;
L is an optional linker up to 18 atoms in length comprising alkyl, alkoxy or alkylamino groups, or combinations thereof; and
wherein for linkage (B):
W is, at each occurrence, independently S or O;
X is, at each occurrence, independently —NR$^8$R$^9$ or —OR$^3$; and
Y is, at each occurrence, independently O or —NR$^{10}$,
R$^8$ is, at each occurrence, independently hydrogen or C$_2$-C$_{12}$ alkyl;
R$^9$ is, at each occurrence, independently hydrogen, C$_1$-C$_{12}$ alkyl, C$_1$-C$_{12}$ aralkyl or aryl;
R$^{10}$ is, at each occurrence, independently hydrogen, C$_1$-C$_{12}$ alkyl or -LNR$^4$R$^5$R$^7$;
wherein R$^8$ and R$^9$ may join to form a 5-18 membered mono or bicyclic heterocycle or R$^8$, R$^9$ or R$^3$ may join with R$^{10}$ to form a 5-7 membered heterocycle, and wherein when X is 4-piparazino, X has the following structure (III):

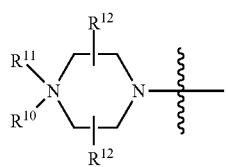
(III)

wherein:
R$^{10}$ is, at each occurrence, independently C$_2$-C$_{12}$ alkyl, C$_1$-C$_{12}$ aminoalkyl, C$_1$-C$_{12}$ alkylcarbonyl, aryl, heteroaryl or heterocyclyl; and R$^{11}$ is, at each occurrence, independently an electron pair, hydrogen or C$_1$-C$_{12}$ alkyl;
R$^{12}$ is, at each occurrence, independently, hydrogen, C$_1$-C$_{12}$ alkyl, C$_1$-C$_{12}$ aminoalkyl, —NH$_2$, —NR$^{13}$R$^{14}$, —NR$^{13}$R$^{14}$R$^{15}$, C$_1$-C$_{12}$ alkylcarbonyl, —CN, trifluoromethyl, amidyl, amidinyl, amidinylalkyl, amidinylalkylcarbonyl, guanidinyl, guanidinylalkyl, guanidinylalkylcarbonyl, cholate, deoxycholate, aryl, heteroaryl, heterocycle, —SR$^{13}$ or C$_1$-C$_{12}$ alkoxy, wherein R$^{13}$, R$^{14}$ and R$^{15}$ are, at each occurrence, independently C$_1$-C$_{12}$ alkyl; and
R$^{17}$ is, at each occurrence, independently absent, hydrogen or C$_1$-C$_6$ alkyl;
R$^{18}$ and R$^{19}$ are, at each occurrence, independently absent, hydrogen, a cell-penetrating peptide, a natural or non-natural amino acid, C$_2$-C$_{30}$ alkylcarbonyl, —C(=O)OR$^{21}$ or R$^{20}$;
R$^{20}$ is, at each occurrence, independently guanidinyl, heterocyclyl, C$_1$-C$_{30}$ alkyl, C$_3$-C$_8$ cycloalkyl; C$_6$-C$_{30}$ aryl, C$_7$-C$_{30}$ aralkyl, C$_3$-C$_{30}$ alkylcarbonyl, C$_3$-C$_8$ cycloalkylcarbonyl, C$_3$-C$_8$ cycloalkylalkylcarbonyl, C$_7$-C$_{30}$ arylcarbonyl, C$_7$-C$_{30}$ aralkylcarbonyl, C$_2$-C$_{30}$ alkyloxycarbonyl, C$_3$-C$_8$ cycloalkyloxycarbonyl, C$_7$-C$_{30}$ aryloxycarbonyl, C$_8$-C$_{30}$ aralkyloxycarbonyl, or —P(=O)(R$^{22}$)$_2$;
R$^{21}$ is C$_1$-C$_{30}$ alkyl comprising one or more oxygen or hydroxyl moieties or combinations thereof;
each R$^{22}$ is independently C$^6$-C$^{12}$ aryloxy;
B is a base-pairing moiety;
L$^1$ is an optional linker up to 18 atoms in length comprising bonds selected from alkyl, hydroxyl, alkoxy, alkylamino, amide, ester, carbonyl, carbamate, phosphorodiamidate, phosphoroamidate, phosphorothioate, piperazine and phosphodiester;
x is an integer of 0 or greater; and
wherein at least one of R$^{18}$ or R$^{19}$ is R$^{20}$ and provided that both of R$^{17}$ and R$^{18}$ are not absent.

These and other aspects of the invention will be apparent upon reference to the following detailed description. To this end, various references are set forth herein which describe in more detail certain background information, procedures, compounds and/or compositions, and are each hereby incorporated by reference in their entirety.

BRIEF DESCRIPTION OF THE DRAWINGS

FIG. 2 shows results for immunofluorescence screening of progerin and lamin A/C.

DETAILED DESCRIPTION OF THE INVENTION

Figure 1A:
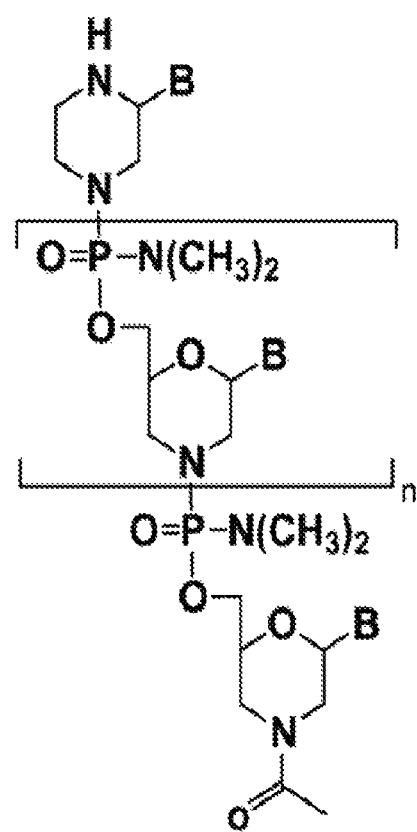
FIG. 1A shows an exemplary morpholino oligomer structure with a phosphorodiamidate linkage.

The present invention relates to oligonucleotides as described herein, and composition containing the same, as well as in vitro methods, wherein the oligonucleotides inhibit expression of mutant LMNA protein mRNA, e.g., by modulating splicing of LMNA pre-mRNA.

Definitions

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred methods and materials are described. For the purposes of the present invention, the following terms are defined below.

The articles "a" and "an" are used herein to refer to one or to more than one (i.e., to at least one) of the grammatical object of the article. By way of example, "an element" means one element or more than one element.

By "about" is meant a quantity, level, value, number, frequency, percentage, dimension, size, amount, weight or length that varies by as much as 30, 25, 20, 25, 10, 9, 8, 7, 6, 5, 4, 3, 2 or 1% to a reference quantity, level, value, number, frequency, percentage, dimension, size, amount, weight or length.

By "coding sequence" is meant any nucleic acid sequence that contributes to the code for the polypeptide product of a gene. By contrast, the term "non-coding sequence" refers to any nucleic acid sequence that does not contribute to the code for the polypeptide product of a gene.

Throughout this specification, unless the context requires otherwise, the words "comprise," "comprises," and "comprising" will be understood to imply the inclusion of a stated step or element or group of steps or elements but not the exclusion of any other step or element or group of steps or elements.

By "consisting of" is meant including, and limited to, whatever follows the phrase "consisting of." Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they materially affect the activity or action of the listed elements.

The terms "complementary" and "complementarity" refer to polynucleotides (i.e., a sequence of nucleotides) related by the base-pairing rules. For example, the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. While perfect complementarity is often desired, some embodiments can include one or more but preferably 6, 5, 4, 3, 2, or 1 mismatches with respect to the target RNA. Variations at any location within the oligomer are included. In certain embodiments, variations in sequence near the termini of an oligomer are generally preferable to variations in the interior, and if present are typically within about 6, 5, 4, 3, 2, or 1 nucleotides of the 5' and/or 3' terminus.

The terms "cell penetrating peptide" or "CPP" are used interchangeably and refer to cationic cell penetrating peptides, also called transport peptides, carrier peptides, or peptide transduction domains. The peptides, as shown herein, have the capability of inducing cell penetration within 30%, 40%, 50%, 60%, 70%, 80%, 90%, or 100% of cells of a given cell culture population, including all integers in between, and allow macromolecular translocation within multiple tissues in vivo upon systemic administration.

The terms "antisense oligomer" or "antisense compound" or "antisense oligonucleotide" or "oligonucleotide" are used interchangeably and refer to a sequence of cyclic subunits, each bearing a base-pairing moiety, linked by intersubunit linkages that allow the base-pairing moieties to hybridize to a target sequence in a nucleic acid (typically an RNA) by Watson-Crick base pairing, to form a nucleic acid:oligomer heteroduplex within the target sequence. The cyclic subunits may be based on ribose or another pentose sugar or, in certain embodiments, a morpholino group (see description of morpholino oligomers below). Also contemplated are peptide nucleic acids (PNAs), locked nucleic acids (LNAs), and 2'-O-Methyl oligonucleotides, and other antisense agents known in the art.

Such an antisense oligomer can be designed to block or inhibit translation of mRNA or to inhibit natural pre-mRNA splice processing, or induce degradation of targeted mRNAs, and may be said to be "directed to" or "targeted against" a target sequence with which it hybridizes. In certain embodiments, the target sequence is a region surrounding or including an AUG start codon of an mRNA, a 3' or 5' splice site of a pre-processed mRNA, or a branch point. The target sequence may be within an exon or within an intron or a combination. The target sequence for a splice site may include an mRNA sequence having its 5' end 1 to about 25 base pairs downstream of a normal splice acceptor junction in a preprocessed mRNA. A preferred target sequence for a splice is any region of a preprocessed mRNA that includes a splice site or is contained entirely within an exon coding sequence or spans a splice acceptor or donor site. An oligomer is more generally said to be "targeted against" a biologically relevant target such as, in the present invention, a human LMNA gene pre-mRNA encoding the lamin A protein, when it is targeted against the nucleic acid of the target in the manner described above. Exemplary targeting sequences include SEQ ID NOS: 3-34

Included are antisense oligonucleotides that comprise, consist essentially of, or consist of one or more of SEQ ID NOS:3-34. Also included are variants of these antisense oligomers, including variant oligomers having 80%, 85%, 90%, 95%, 97%, 98%, or 99% (including all integers in between) sequence identity or sequence homology to any one of SEQ ID NOS:3-34, and/or variants that differ from these sequences by about 1, 2, 3, 4, 5, 6, 7, 8, 9, or 10 nucleotides, preferably those variants that modulate progerin expression in a cell. Also included are oligonucleotides of any one or more of SEQ ID NOS: 3-34, which comprise a suitable number of cationic or other modified linkages, as described herein, e.g., up to about 1 per every 2-5 uncharged linkages, such as about 4-5 per every 10 uncharged linkages, and/or which comprise an Arg-rich cell-penetrating transport peptide attached thereto, as also described herein.

The terms "morpholino oligomer" or "PMO" (phosphoramidate- or phosphorodiamidate morpholino oligomer) refer to an oligonucleotide analog composed of morpholino subunit structures, where (i) the structures are linked together by phosphorus-containing linkages, one to three atoms long, preferably two atoms long, and preferably uncharged or cationic, joining the morpholino nitrogen of one subunit to a 5' exocyclic carbon of an adjacent subunit, and (ii) each morpholino ring bears a purine or pyrimidine or an equivalent base-pairing moiety effective to bind, by base specific hydrogen bonding, to a base in a polynucleotide. Variations can be made to this linkage as long as they do not interfere with binding or activity. For example, the oxygen attached to phosphorus may be substituted with sulfur (thiophosphorodiamidate). The 5' oxygen may be substituted with amino or lower alkyl substituted amino. The pendant nitrogen attached to phosphorus may be unsubstituted, monosubstituted, or disubstituted with (optionally substituted) lower alkyl. See also the discussion of cationic linkages below. The purine or pyrimidine base pairing moiety is typically adenine, cytosine, guanine, uracil, thymine or inosine. The synthesis, structures, and binding characteristics of morpholino oligomers are detailed in U.S. Pat. Nos. 5,698,685, 5,217,866, 5,142,047, 5,034,506, 5,166,315, 5,521,063, and 5,506,337, and PCT Appn. Nos. PCT/US07/11435 (cationic linkages) and U.S. Ser. No. 08/012,804 (improved synthesis), all of which are incorporated herein by reference.

"PMO+" refers to phosphorodiamidate morpholino oligomers comprising any number of (1-piperazino)phosphinylideneoxy, (1-(4-(ω-guanidino-alkanoyl))-piperazino) phosphinylideneoxy linkages (A2 and A3) that have been described previously (see e.g., PCT publication WO/2008/036127 which is incorporated herein by reference in its entirety.

"PMO-X" refers to phosphorodiamidate morpholino oligomers disclosed herein comprising at least one (B) linkage or at least one of the disclosed terminal modifications, and as disclosed in WO2011/150408 and US2012/0065169, which are incorporated herein by reference in their entireties. Further PMO-X phosphorodiamidate morpholino oligomers useful herein may be found in U.S. Provisional Application No. 61/561,806, filed Nov. 18, 2011, which is incorporated herein by reference in its entirety.

A "phosphoramidate" group comprises phosphorus having three attached oxygen atoms and one attached nitrogen atom, while a "phosphorodiamidate" group comprises phosphorus having two attached oxygen atoms and two attached nitrogen atoms. In the uncharged or the modified intersubunit linkages of the oligomers described herein and copending U.S. Patent Application Nos. 61/349,783 and Ser. No. 11/801,885, one nitrogen is always pendant to the backbone chain. The second nitrogen, in a phosphorodiamidate linkage, is typically the ring nitrogen in a morpholino ring structure.

"Thiophosphoramidate" or "thiophosphorodiamidate" linkages are phosphoramidate or phosphorodiamidate linkages, respectively, wherein one oxygen atom, typically the oxygen pendant to the backbone, is replaced with sulfur.

"Intersubunit linkage" refers to the linkage connecting two morpholino subunits, for example structure (I).

"Charged", "uncharged", "cationic" and "anionic" as used herein refer to the predominant state of a chemical moiety at near-neutral pH, e.g., about 6 to 8. For example, the term may refer to the predominant state of the chemical moiety at physiological pH, that is, about 7.4.

The term "oligonucleotide analog" refers to an oligonucleotide having (i) a modified backbone structure, e.g., a backbone other than the standard phosphodiester linkage found in natural oligo- and polynucleotides, and (ii) optionally, modified sugar moieties, e.g., morpholino moieties rather than ribose or deoxyribose moieties. Oligonucleotide analogs support bases capable of hydrogen bonding by Watson-Crick base pairing to standard polynucleotide bases, where the analog backbone presents the bases in a manner to permit such hydrogen bonding in a sequence-specific fashion between the oligonucleotide analog molecule and bases in a standard polynucleotide (e.g., single-stranded RNA or single-stranded DNA). Preferred analogs are those having a substantially uncharged, phosphorus containing backbone.

A substantially uncharged, phosphorus containing backbone in an oligonucleotide analog is one in which a majority of the subunit linkages, e.g., between 50-100%, typically at least 60% to 100% or 75% or 80% of its linkages, are uncharged, and contain a single phosphorous atom. Antisense oligonucleotides and oligonucleotide analogs may contain between about 8 and 40 subunits, typically about 8-25 subunits, and preferably about 12 to 25 subunits (including all integers and ranges in between). In certain embodiments, oligonucleotides may have exact sequence complementarity to the target sequence or near complementarity, as defined below.

A "subunit" of an oligonucleotide refers to one nucleotide (or nucleotide analog) unit. The term may refer to the nucleotide unit with or without the attached intersubunit linkage, although, when referring to a "charged subunit", the charge typically resides within the intersubunit linkage (e.g., a phosphate or phosphorothioate linkage or a cationic linkage).

The purine or pyrimidine base pairing moiety is typically adenine, cytosine, guanine, uracil, thymine or inosine. Also included are bases such as pyridin-4-one, pyridin-2-one, phenyl, pseudouracil, 2,4,6-trime115thoxy benzene, 3-methyl uracil, dihydrouridine, naphthyl, aminophenyl, 5-alkylcytidines (e.g., 5-methylcytidine), 5-alkyluridines (e.g., ribothymidine), 5-halouridine (e.g., 5-bromouridine) or 6-azapyrimidines or 6-alkylpyrimidines (e.g. 6-methyluridine), propyne, quesosine, 2-thiouridine, 4-thiouridine, wybutosine, wybutoxosine, 4-acetyltidine, 5-(carboxyhydroxymethyl)uridine, 5'-carboxymethylaminomethyl-2-thiouridine, 5-carboxymethylaminomethyluri dine, β-D-galactosylqueosine, 1-methyladenosine, 1-methylinosine, 2,2-dimethylguanosine, 3-methylcytidine, 2-methyladenosine, 2-methylguanosine, N6-methyladenosine, 7-methylguanosine, 5-methoxyaminomethyl-2-thiouridine, 5-methyl aminomethyluridine, 5-methylcarbonyhnethyluridine, 5-methyloxyuridine, 5-methyl-2-thiouridine, 2-methylthio-N6-isopentenyladenosine, β-D-mannosylqueosine, uridine-5-oxyacetic acid, 2-thiocytidine, threonine derivatives and others (Burgin et al., 1996, Biochemistry, 35, 14090; Uhlman & Peyman, supra). By "modified bases" in this aspect is meant nucleotide bases other than adenine (A), guanine (G), cytosine (C), thymine (T), and uracil (U), as illustrated above; such bases can be used at any position in the antisense molecule. Persons skilled in the art will appreciate that depending on the uses of the oligomers, Ts and Us are interchangeable. For instance, with other antisense chemistries such as 2'-O-methyl antisense oligonucleotides that are more RNA-like, the T bases may be shown as U (see, e.g., Sequence Listing).

An "amino acid subunit" or "amino acid residue" can refer to an α-amino acid residue (—CO—CHR—NH—) or a β- or other amino acid residue (e.g., —CO—$(CH_2)_n$CHR—NH—), where R is a side chain (which may include hydrogen) and n is 1 to 7, preferably 1 to 4.

The term "naturally occurring amino acid" refers to an amino acid present in proteins found in nature, such as the 20 (L)-amino acids utilized during protein biosynthesis as well as others such as 4-hydroxyproline, hydroxylysine, desmosine, isodesmosine, homocysteine, citrulline and ornithine. The term "non-natural amino acids" refers to those amino acids not present in proteins found in nature, examples include beta-alanine (β-Ala), 6-aminohexanoic acid (Ahx) and 6-aminopentanoic acid. Additional examples of "non-natural amino acids" include, without limitation, (D)-amino acids, norleucine, norvaline, p-fluorophenylalanine, ethionine and the like, which are known to a person skilled in the art.

By "isolated" is meant material that is substantially or essentially free from components that normally accompany it in its native state. For example, an "isolated polynucleotide" or "isolated oligonucleotide," as used herein, may refer to a polynucleotide that has been purified or removed from the sequences that flank it in a naturally-occurring state, e.g., a DNA fragment that has been removed from the sequences that are normally adjacent to the fragment.

An "effective amount" refers to an amount of antisense oligomer effective to modulate expression of progerin in vitro By "enhance" or "enhancing," or "increase" or "increasing," or "stimulate" or "stimulating," refers generally to the ability of one or antisense compounds or compositions to produce or cause a greater physiological response (i.e., downstream effects) in a cell, as compared to the response caused by either no antisense compound or a control compound. An "increased" or "enhanced" amount is typically a "statistically significant" amount, and may include an increase that is 1.1, 1.2, 2, 3, 4, 5, 6, 7, 8, 9, 10, 15, 20, 30, 40, 50 or more times (e.g., 500, 1000 times) (including all integers and decimal points in between and above 1), e.g., 1.5, 1.6, 1.7, 1.8, etc.) the amount produced by no antisense compound (the absence of an agent) or a control compound.

The term "reduce" or "inhibit" may relate generally to the ability of one or more antisense compounds of the invention to "decrease" a relevant physiological or cellular response, as measured according to routine techniques in the diagnostic art. Relevant physiological or cellular responses (in vivo or in vitro) will be apparent to persons skilled in the art, and may include, for example, reductions in expression of progerin as measured by mRNA and/or protein levels. A "decrease" in a response may be "statistically significant" as compared to the response produced by no antisense compound or a control composition, and may include a 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100% decrease, including all integers in between.

The term "target sequence" refers to a portion of the target RNA against which the oligonucleotide or antisense agent is directed, that is, the sequence to which the oligonucleotide will hybridize by Watson-Crick base pairing of a complementary sequence. In certain embodiments, the target sequence may be a contiguous region of a pre-mRNA that includes both intron and exon target sequence. In certain other embodiments, the target sequence will consist exclusively of either intron or exon sequences.

The term "targeting sequence" or "antisense targeting sequence" refers to the sequence in an oligonucleotide or other antisense agent that is complementary (meaning, in addition, substantially complementary) to the target sequence in the RNA genome. The entire sequence, or only a portion, of the antisense compound may be complementary to the target sequence. For example, in an oligonucleotide having 20-30 bases, about 6, 7, 8, 9, 10, 11, 12, 13, 14, 15, 16, 17, 18, 19, 20, 21, 22, 23, 24, 25, 26, 27, 28, or 29 may be targeting sequences that are complementary to the target region. Typically, the targeting sequence is formed of contiguous bases, but may alternatively be formed of non-contiguous sequences that when placed together, e.g., from opposite ends of the oligonucleotide, constitute sequence that spans the target sequence.

Target and targeting sequences are described as "complementary" to one another when hybridization occurs in an antiparallel configuration. A targeting sequence may have "near" or "substantial" complementarity to the target sequence and still function for the purpose of the present invention, that is, it may still be functionally "complementary." In certain embodiments, an oligonucleotide may have at most one mismatch with the target sequence out of 10 nucleotides, and preferably at most one mismatch out of 20. Alternatively, an oligonucleotide may have at least 90% sequence homology, and preferably at least 95% sequence homology, with the exemplary antisense targeting sequences described herein.

An oligonucleotide "specifically hybridizes" to a target polynucleotide if the oligomer hybridizes to the target under physiological conditions, with a Tm substantially greater than 45° C., preferably at least 50° C., and typically 60° C.-80° C. or higher. Such hybridization preferably corresponds to stringent hybridization conditions. At a given ionic strength and pH, the Tm is the temperature at which 50% of a target sequence hybridizes to a complementary polynucleotide. Again, such hybridization may occur with "near" or "substantial" complementarity of the antisense oligomer to the target sequence, as well as with exact complementarity.

"Homology" refers to the percentage number of amino acids that are identical or constitute conservative substitutions. Homology may be determined using sequence comparison programs such as GAP (Deveraux et al., 1984, *Nucleic Acids Research* 12, 387-395). In this way sequences of a similar or substantially different length to those cited herein could be compared by insertion of gaps into the alignment, such gaps being determined, for example, by the comparison algorithm used by GAP.

The terms "sequence identity" or, for example, comprising a "sequence 50% identical to," as used herein, refer to the extent that sequences are identical on a nucleotide-by-nucleotide basis or an amino acid-by-amino acid basis over a window of comparison. Thus, a "percentage of sequence identity" may be calculated by comparing two optimally aligned sequences over the window of comparison, determining the number of positions at which the identical nucleic acid base (e.g., A, T, C, G, I) or the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity.

Terms used to describe sequence relationships between two or more polynucleotides or polypeptides include "reference sequence," "comparison window," "sequence identity," "percentage of sequence identity," and "substantial identity". A "reference sequence" is at least 8 or 10 but frequently 15 to 18 and often at least 25 monomer units, inclusive of nucleotides and amino acid residues, in length. Because two polynucleotides may each comprise (1) a sequence (i.e., only a portion of the complete polynucleotide sequence) that is similar between the two polynucleotides, and (2) a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window" refers to a conceptual segment of at least 6 contiguous positions, usually about 50 to about 100, more usually about 100 to about 150 in which a sequence is compared to a reference sequence of the same number of contiguous positions after the two sequences are optimally aligned. The comparison window may comprise additions or deletions (i.e., gaps) of about 20% or less as compared to the reference sequence (which does not comprise additions or deletions) for optimal alignment of the two sequences.

Optimal alignment of sequences for aligning a comparison window may be conducted by computerized implementations of algorithms (GAP, BESTFIT, FASTA, and TFASTA in the Wisconsin Genetics Software Package Release 7.0, Genetics Computer Group, 575 Science Drive Madison, Wis., USA) or by inspection and the best alignment (i.e., resulting in the highest percentage homology over the comparison window) generated by any of the various methods selected. Reference also may be made to the BLAST family of programs as for example disclosed by Altschul et al., 1997, *Nucl. Acids Res.* 25:3389. A detailed discussion of sequence analysis can be found in Unit 19.3 of Ausubel et al., "Current Protocols in Molecular Biology," John Wiley & Sons Inc, 1994-1998, Chapter 15.

A "nuclease-resistant" oligomeric molecule (oligomer) refers to one whose backbone is substantially resistant to nuclease cleavage, in non-hybridized or hybridized form; by common extracellular and intracellular nucleases in the body; that is, the oligomer shows little or no nuclease cleavage under normal nuclease conditions in the body to which the oligomer is exposed.

An agent is "actively taken up by mammalian cells" when the agent can enter the cell by a mechanism other than passive diffusion across the cell membrane. The agent may be transported, for example, by "active transport," referring to transport of agents across a mammalian cell membrane by e.g., an ATP-dependent transport mechanism, or by "facilitated transport," referring to transport of antisense agents across the cell membrane by a transport mechanism that requires binding of the agent to a transport protein, which then facilitates passage of the bound agent across the membrane. For both active and facilitated transport, oligonucleotide analogs preferably have a substantially uncharged backbone, as defined below.

A "heteroduplex" refers to a duplex between an antisense oligonucleotide and the complementary portion of a target RNA. A "nuclease-resistant heteroduplex" refers to a heteroduplex formed by the binding of an antisense oligomer to its complementary target, such that the heteroduplex is substantially resistant to in vivo degradation by intracellular and extracellular nucleases, such as RNaseH, which are capable of cutting double-stranded RNA/RNA or RNA/DNA complexes.

As used herein, the term "body fluid" encompasses a variety of sample types obtained from a subject including, urine, saliva, plasma, blood, spinal fluid, or other sample of biological origin, such as skin cells or dermal debris, and may refer to cells or cell fragments suspended therein, or the liquid medium and its solutes.

The term "relative amount" is used where a comparison is made between a test measurement and a control measurement. The relative amount of a reagent forming a complex in a reaction is the amount reacting with a test specimen, compared with the amount reacting with a control specimen. The control specimen may be run separately in the same assay, or it may be part of the same sample (for example, normal tissue surrounding a malignant area in a tissue section).

A wild-type gene or gene product is that which is most frequently observed in a population and is thus arbitrarily designed the "normal" or "wild-type" form of the gene.

The chemical terms below have the following meanings, unless indicated otherwise:

"Amino" refers to the —$NH_2$ radical.

"Cyano" or "nitrile" refers to the —CN radical.

"Hydroxy" or "hydroxyl" refers to the —OH radical.

"Imino" refers to the =NH substituent.

"Guanidinyl" refers to the —NHC(=NH)$NH_2$ substituent.

"Amidinyl" refers to the —C(=NH)$NH_2$ substituent.

"Nitro" refers to the —$NO_2$ radical.

"Oxo" refers to the =O substituent.

"Thioxo" refers to the =S substituent.

"Cholate" refers to the following structure:

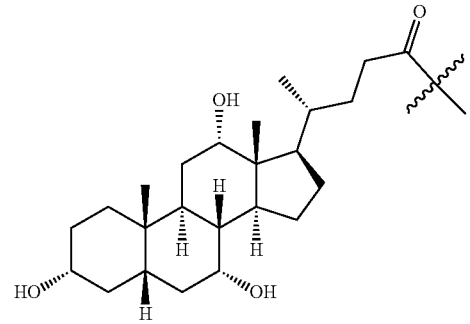

"Deoxycholate" refers to the following structure:

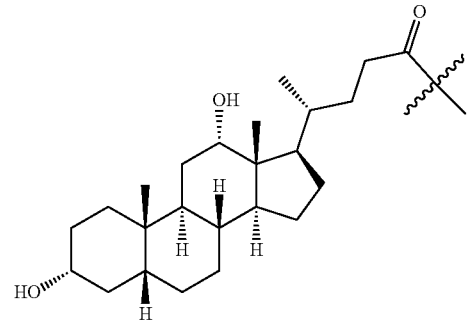

"Alkyl" refers to a straight or branched hydrocarbon chain radical which is saturated or unsaturated (i.e., contains one or more double and/or triple bonds), having from one to thirty carbon atoms, and which is attached to the rest of the molecule by a single bond. Alkyls comprising any number of carbon atoms from 1 to 30 are included. An alkyl comprising up to 30 carbon atoms is referred to as a $C_1$-$C_{30}$ alkyl, likewise, for example, an alkyl comprising up to 12 carbon atoms is a $C_1$-$C_{12}$ alkyl. Alkyls (and other moieties defined herein) comprising other numbers of carbon atoms are represented similarly. Alkyl groups include, but are not limited to, $C_1$-$C_{30}$ alkyl, $C_1$-$C_{20}$ alkyl, $C_1$-$C_{15}$ alkyl, $C_1$-$C_{10}$ alkyl, $C_1$-$C_8$ alkyl, $C_1$-$C_6$ alkyl, $C_1$-$C_4$ alkyl, $C_1$-$C_3$ alkyl, $C_1$-$C_2$ alkyl, $C_2$-$C_8$ alkyl, $C_3$-$C_8$ alkyl and $C_4$-$C_8$ alkyl. Representative alkyl groups include, but are not limited to, methyl, ethyl, n-propyl, 1-methylethyl (iso-propyl), n-butyl, i-butyl, s-butyl, n-pentyl, 1,1-dimethylethyl (t-butyl), 3-methylhexyl, 2-methylhexyl, ethenyl, prop-1-enyl, but-1-enyl, pent-1-enyl, penta-1,4-dienyl, ethynyl, propynyl, but-2-ynyl, but-3-ynyl, pentynyl, hexynyl, and the like. Unless stated otherwise specifically in the specification, an alkyl group may be optionally substituted as described below.

"Alkylene" or "alkylene chain" refers to a straight or branched divalent hydrocarbon chain linking the rest of the molecule to a radical group. Alkylenes may be saturated or unsaturated (i.e., contains one or more double and/or triple bonds). Representative alkylenes include, but are not limited to, $C_1$-$C_{12}$ alkylene, $C_1$-$C_8$ alkylene, $C_1$-$C_6$ alkylene, $C_1$-$C_4$ alkylene, $C_1$-$C_3$ alkylene, $C_1$-$C_2$ alkylene, $C_1$ alkylene. Representative alkylene groups include, but are not limited to, methylene, ethylene, propylene, n-butylene, ethenylene, propenylene, n-butenylene, propynylene, n-butynylene, and the like. The alkylene chain is attached to the rest of the molecule through a single or double bond and to the radical group through a single or double bond. The points of attachment of the alkylene chain to the rest of the molecule and to the radical group can be through one carbon or any two carbons within the chain. Unless stated otherwise specifically in the specification, an alkylene chain may be optionally substituted as described below.

"Alkoxy" refers to a radical of the formula —$OR_a$ where $R_a$ is an alkyl radical as defined. Unless stated otherwise specifically in the specification, an alkoxy group may be optionally substituted as described below.

"Alkoxyalkyl" refers to a radical of the formula —$R_bOR_a$ where $R_a$ is an alkyl radical as defined and where $R_b$ is an alkylene radical as defined. Unless stated otherwise specifically in the specification, an alkoxyalkyl group may be optionally substituted as described below.

"Alkylcarbonyl" refers to a radical of the formula —C(=O)$R_a$ where $R_a$ is an alkyl radical as defined above. Unless stated otherwise specifically in the specification, an alkylcarbonyl group may be optionally substituted as described below.

"Alkyloxycarbonyl" refers to a radical of the formula —C(=O)O$R_a$ where $R_a$ is an alkyl radical as defined. Unless stated otherwise specifically in the specification, an alkyloxycarbonyl group may be optionally substituted as described below.

"Alkylamino" refers to a radical of the formula —NH$R_a$ or —N$R_aR_a$ where each $R_a$ is, independently, an alkyl radical as defined above. Unless stated otherwise specifically in the specification, an alkylamino group may be optionally substituted as described below.

"Amidyl" refers to a radical of the formula —N(H)C(=O) $R_a$ where $R_a$ is an alkyl or aryl radical as defined herein. Unless stated otherwise specifically in the specification, an amidyl group may be optionally substituted as described below.

"Amidinylalkyl" refers a radical of the formula —$R_b$—C(=NH)NH$_2$ where $R_b$ is an alkylene radical as defined above. Unless stated otherwise specifically in the specification, an amidinylalkyl group may be optionally substituted as described below.

"Amidinylalkylcarbonyl" refers a radical of the formula —C(=O)$R_b$—C(=NH)NH$_2$ where $R_b$ is an alkylene radical as defined above. Unless stated otherwise specifically in the specification, an amidinylalkylcarbonyl group may be optionally substituted as described below.

"Aminoalkyl" refers to a radical of the formula —$R_b$—N$R_aR_a$ where $R_b$ is an alkylene radical as defined above, and each $R_a$ is independently a hydrogen or an alkyl radical.

"Thioalkyl" refers to a radical of the formula —S$R_a$ where $R_a$ is an alkyl radical as defined above. Unless stated otherwise specifically in the specification, a thioalkyl group may be optionally substituted.

"Aryl" refers to a radical derived from a hydrocarbon ring system comprising hydrogen, 6 to 30 carbon atoms and at least one aromatic ring. The aryl radical may be a monocyclic, bicyclic, tricyclic or tetracyclic ring system, which may include fused or bridged ring systems. Aryl radicals include, but are not limited to, aryl radicals derived from the hydrocarbon ring systems of aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, the term "aryl" or the prefix "ar-" (such as in "aralkyl") is meant to include aryl radicals that are optionally substituted.

"Aralkyl" refers to a radical of the formula —$R_b$—$R_c$ where $R_b$ is an alkylene chain as defined above and $R_c$ is one or more aryl radicals as defined above, for example, benzyl, diphenylmethyl, trityl and the like. Unless stated otherwise specifically in the specification, an aralkyl group may be optionally substituted.

"Arylcarbonyl" refers to a radical of the formula —C(=O)$R_c$ where $R_c$ is one or more aryl radicals as defined above, for example, phenyl. Unless stated otherwise specifically in the specification, an arylcarbonyl group may be optionally substituted.

"Aryloxycarbonyl" refers to a radical of the formula —C(=O)O$R_c$ where $R_c$ is one or more aryl radicals as defined above, for example, phenyl. Unless stated otherwise specifically in the specification, an aryloxycarbonyl group may be optionally substituted.

"Aralkylcarbonyl" refers to a radical of the formula —C(=O)$R_b$—$R_c$ where $R_b$ is an alkylene chain as defined above and R, is one or more aryl radicals as defined above, for example, phenyl. Unless stated otherwise specifically in the specification, an aralkylcarbonyl group may be optionally substituted.

"Aralkyloxycarbonyl" refers to a radical of the formula —C(=O)O$R_b$—$R_c$ where $R_b$ is an alkylene chain as defined above and R, is one or more aryl radicals as defined above, for example, phenyl. Unless stated otherwise specifically in the specification, an aralkyloxycarbonyl group may be optionally substituted.

"Aryloxy" refers to a radical of the formula —O$R_c$ where $R_c$ is one or more aryl radicals as defined above, for example, phenyl. Unless stated otherwise specifically in the specification, an arylcarbonyl group may be optionally substituted.

"Cycloalkyl" refers to a stable, non-aromatic, monocyclic or polycyclic carbocyclic ring, which may include fused or bridged ring systems, which is saturated or unsaturated, and attached to the rest of the molecule by a single bond. Representative cycloalkyls include, but are not limited to, cycloaklyls having from three to fifteen carbon atoms and from three to eight carbon atoms, Monocyclic cyclcoalkyl radicals include, for example, cyclopropyl, cyclobutyl, cyclopentyl, cyclohexyl, cycloheptyl, and cyclooctyl. Polycyclic radicals include, for example, adamantyl, norbornyl, decalinyl, and 7,7-dimethyl-bicyclo[2.2.1]heptanyl. Unless otherwise stated specifically in the specification, a cycloalkyl group may be optionally substituted.

"Cycloalkylalkyl" refers to a radical of the formula —$R_bR_d$ where $R_b$ is an alkylene chain as defined above and $R_d$ is a cycloalkyl radical as defined above. Unless stated otherwise specifically in the specification, a cycloalkylalkyl group may be optionally substituted.

"Cycloalkylcarbonyl" refers to a radical of the formula —C(=O)$R_d$ where $R_d$ is a cycloalkyl radical as defined above. Unless stated otherwise specifically in the specification, a cycloalkylcarbonyl group may be optionally substituted.

Cycloalkyloxycarbonyl" refers to a radical of the formula —C(=O)O$R_d$ where $R_d$ is a cycloalkyl radical as defined above. Unless stated otherwise specifically in the specification, a cycloalkyloxycarbonyl group may be optionally substituted.

"Fused" refers to any ring structure described herein which is fused to an existing ring structure. When the fused ring is a heterocyclyl ring or a heteroaryl ring, any carbon atom on the existing ring structure which becomes part of the fused heterocyclyl ring or the fused heteroaryl ring may be replaced with a nitrogen atom.

"Guanidinylalkyl" refers a radical of the formula —$R_b$—NHC(=NH)$NH_2$ where $R_b$ is an alkylene radical as defined above. Unless stated otherwise specifically in the specification, a guanidinylalkyl group may be optionally substituted as described below.

"Guanidinylalkylcarbonyl" refers a radical of the formula —C(=O)$R_b$—NHC(=NH)$NH_2$ where $R_b$ is an alkylene radical as defined above. Unless stated otherwise specifically in the specification, a guanidinylalkylcarbonyl group may be optionally substituted as described below.

"Halo" or "halogen" refers to bromo, chloro, fluoro or iodo.

"Haloalkyl" refers to an alkyl radical, as defined above, that is substituted by one or more halo radicals, as defined above, e.g., trifluoromethyl, difluoromethyl, fluoromethyl, trichloromethyl, 2,2,2-trifluoroethyl, 1,2-difluoroethyl, 3-bromo-2-fluoropropyl, 1,2-dibromoethyl, and the like. Unless stated otherwise specifically in the specification, a haloalkyl group may be optionally substituted.

"Perhalo" or "perfluoro" refers to a moiety in which each hydrogen atom has been replaced by a halo atom or fluorine atom, respectively.

"Heterocyclyl" or "heterocyclic ring" refers to a stable 3- to 24-membered non-aromatic ring radical comprising 2 to 23 carbon atoms and from one to 8 heteroatoms selected from the group consisting of nitrogen, oxygen, phosphorous and sulfur. Unless stated otherwise specifically in the specification, the heterocyclyl radical may be a monocyclic, bicyclic, tricyclic or tetracyclic ring system, which may include fused or bridged ring systems; and the nitrogen, carbon or sulfur atoms in the heterocyclyl radical may be optionally oxidized; the nitrogen atom may be optionally quaternized; and the heterocyclyl radical may be partially or fully saturated. Examples of such heterocyclyl radicals include, but are not limited to, dioxolanyl, thienyl[1,3] dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, 1,1-dioxo-thiomorpholinyl, 12-crown-4, 15-crown-5, 18-crown-6, 21-crown-7, aza-18-crown-6, diaza-18-crown-6, aza-21-crown-7, and diaza-21-crown-7. Unless stated otherwise specifically in the specification, a heterocyclyl group may be optionally substituted.

"Heteroaryl" refers to a 5- to 14-membered ring system radical comprising hydrogen atoms, one to thirteen carbon atoms, one to six heteroatoms selected from the group consisting of nitrogen, oxygen, phosphorous and sulfur, and at least one aromatic ring. For purposes of this invention, the heteroaryl radical may be a monocyclic, bicyclic, tricyclic or tetracyclic ring system, which may include fused or bridged ring systems; and the nitrogen, carbon or sulfur atoms in the heteroaryl radical may be optionally oxidized; the nitrogen atom may be optionally quaternized. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e., thienyl). Unless stated otherwise specifically in the specification, a heteroaryl group may be optionally substituted.

All the above groups may be either substituted or unsubstituted. The term "substituted" as used herein means any of the above groups (i.e., alkyl, alkylene, alkoxy, alkoxyalkyl, alkylcarbonyl, alkyloxycarbonyl, alkylamino, amidyl, amidinylalkyl, amidinylalkylcarbonyl, aminoalkyl, aryl, aralkyl, arylcarbonyl, aryloxycarbonyl, aralkylcarbonyl, aralkyloxycarbonyl, aryloxy, cycloalkyl, cycloalkylalkyl, cycloalkylcarbonyl, cycloalkylalkylcarbonyl, cycloalkyloxycarbonyl, guanidinylalkyl, guanidinylalkylcarbonyl, haloalkyl, heterocyclyl and/or heteroaryl), may be further functionalized wherein at least one hydrogen atom is replaced by a bond to a non-hydrogen atom substituent. Unless stated specifically in the specification, a substituted group may include one or more substituents selected from: oxo, —$CO_2H$, nitrile, nitro, hydroxyl, thiooxy, alkyl, alkylene, alkoxy, alkoxyalkyl, alkylcarbonyl, alkyloxycarbonyl, aryl, aralkyl, arylcarbonyl, aryloxycarbonyl, aralkylcarbonyl, aralkyloxycarbonyl, aryloxy, cycloalkyl, cycloalkylalkyl, cycloalkylcarbonyl, cycloalkylalkylcarbonyl, cycloalkyloxycarbonyl, heterocyclyl, heteroaryl, dialkylamines, arylamines, alkylarylamines, diarylamines, N-oxides, imides, and enamines; a silicon atom in groups such as trialkylsilyl groups, dialkylarylsilyl groups, alkyldiarylsilyl groups, triarylsilyl groups, perfluoroalkyl or perfluoroalkoxy, for example, trifluoromethyl or trifluoromethoxy. "Substituted" also means any of the above groups in which one or more hydrogen atoms are replaced by a higher-order bond (e.g., a double- or triple-bond) to a heteroatom such as oxygen in oxo, carbonyl, carboxyl, and ester groups; and nitrogen in groups such as imines, oximes, hydrazones, and nitriles. For example, "substituted" includes any of the above groups in which one or more hydrogen atoms are replaced with —$NR_gC(=O)NR_gR_h$, —$NR_gC(=O)OR_h$, —$NR_gSO_2R_h$, —OC(=O)$NR_gR_h$, —$OR_g$, —$SR_g$, —$SOR_g$, —$SO_2R_g$, —$OSO_2R_g$, —$SO_2OR_g$, =$NSO_2R_g$, and —$SO_2NR_gR_h$.

"Substituted" also means any of the above groups in which one or more hydrogen atoms are replaced with —C(=O)R$_g$, —C(=O)OR$_g$, —CH$_2$SO$_2$R$_g$, —CH$_2$SO$_2$NR$_g$R$_h$, —SH, —SR$_g$ or —SSR$_g$. In the foregoing, R$_g$ and R$_h$ are the same or different and independently hydrogen, alkyl, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl. In addition, each of the foregoing substituents may also be optionally substituted with one or more of the above substituents. Furthermore, any of the above groups may be substituted to include one or more internal oxygen or sulfur atoms. For example, an alkyl group may be substituted with one or more internal oxygen atoms to form an ether or polyether group. Similarly, an alkyl group may be substituted with one or more internal sulfur atoms to form a thioether, disulfide, etc. Amidyl moieties may be substituted with up to 2 halo atoms, while other groups above may be substituted with one or more halo atoms. With the exception of alkyl groups, all other groups may also be substituted with amino or monoalklyamino. With the exception of alkyl and alkylcarbonyl groups, all other groups may also be substituted with guanidinyl or amidynyl. Optional substitutents for any of the above groups also include arylphosphoryl, for example —R$_a$P(Ar)$_3$ wherein R$_a$ is an alkylene and Ar is aryl moiety, for example phenyl.

"Lower alkyl" refers to an alkyl radical of one to six carbon atoms, as exemplified by methyl, ethyl, n-butyl, i-butyl, t-butyl, isoamyl, n-pentyl, and isopentyl. In certain embodiments, a "lower alkyl" group has one to four carbon atoms. In other embodiments a "lower alkyl" group has one to two carbon atoms; i.e. methyl or ethyl. Analogously, "lower alkenyl" refers to an alkenyl radical of two to six, preferably three or four, carbon atoms, as exemplified by allyl and butenyl.

A "non-interfering" substituent is one that does not adversely affect the ability of an antisense oligomer as described herein to bind to its intended target. Such substituents include small and/or relatively non-polar groups such as methyl, ethyl, methoxy, ethoxy, or fluoro.

LMNA Targeting

Examples include antisense oligonucleotides that target SEQ ID NOs: 1 and/or 2, discussed below.

Certain antisense oligonucleotides may comprise a targeting sequence that is complementary to one or more bases of exon 11 in the human LMNA gene including the wild-type sequence (SEQ ID NO: 1) and/or the sequence found in HGPS patients, as shown in SEQ ID NO: 2. These target sequences are shown in Table 1 below:

TABLE 1

Exemplary LMNA Target Sequences

| NAME | SEQUENCE | SEQ ID NO: |
|---|---|---|
| LMNA exon 11 | GGCTCCCACTGCAGCAGCTCGGG GGACCCCGCTGAGTACAACCTGC GCTCGCGCACCGTGCTGTGCGGG ACCTGCGGGCAGCCTGCCGACAA GGCATCTGCCAGCGGCTCAGGAG CCCAGGTGGGCGGACCCATCTCC TCTGGCTCTTCTGCCTCCAGTGT CACGGTCACTCGCAGCTACCGCA GTGTGGGGGGCAGTGGGGGTGGC AGCTTCGGGGACAATCTGGTCAC CCGCTCCTACCTCCTGGGCAACT CCAGCCCCCGAACCCAG | 1 |

TABLE 1-continued

Exemplary LMNA Target Sequences

| NAME | SEQUENCE | SEQ ID NO: |
|---|---|---|
| HGPS exon 11 | GGCTCCCACTGCAGCAGCTCGGG GGACCCCGCTGAGTACAACCTGC GCTCGCGCACCGTGCTGTGCGGG ACCTGCGGGCAGCCTGCCGACAA GGCATCTGCCAGCGGCTCAGGAG CCC<u>AGGTGGGT</u>GGACCCATCTCC TCTGGCTCTTCTGCCTCCAGTGT CACGGTCACTCGCAGCTACCGCA GTGTGGGGGGCAGTGGGGGTGGC AGCTTCGGGGACAATCTGGTCAC CCGCTCCTACCTCCTGGGCAACT CCAGCCCCCGAACCCAG | 2 |

Examples include antisense oligonucleotides that are fully complementary to LMNA exon 11 (SEQ ID NO: 1 or 2) including those that are also complementary to the cryptic splice site of LMNA exon 11 underlined in SEQ ID NO:1 and 2 in Table 1 (e.g., <u>CAGGTGGGC/T</u>). Certain antisense oligonucleotides may comprise a targeting sequence where the 3'-most base is complementary to a base in LMNA exon 11 that is 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 bases downstream of the underlined cryptic splice site in SEQ ID NO:1 or 2 (see Table 1), or which is complementary to a base in LMNA exon 11 that is 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 upstream of the cryptic splice site. Exemplary oligonucleotides of this type are among those listed below as SEQ ID NOs: 3-16. Certain antisense oligonucleotides may comprise a targeting sequence where the 3'-most base is complementary to a base in LMNA intron 10 that is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59 or 60 bases upstream of LMNA exon 11 SEQ ID NO: 1 or 2 (see Table 1). Certain antisense oligonucleotides may comprise a targeting sequence where the 3'-most base is complementary to a base in LMNA exon 10 that is 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 bases upstream of LMNA intron 10. Certain embodiments relate to the use of a combination of these antisense agents. Specific embodiments include antisense oligonucleotides comprising all or a portion (e.g., 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 bases) of SEQ ID NO: 1 and/or 2.

Antisense oligonucleotides can also be targeted against, or be complementary to, a variety of region(s) in a pre-processed LMNA mRNA, such as an exon, an intron, an exon-intron junction, or a splice junction. For instance, certain antisense oligonucleotides may comprise a targeting sequence that is complementary to a region (target sequence) that overlaps the splice junction of a splice donor (SD) or splice acceptor (SA) sites of exons 10 and 11 of LMNA pre-mRNA, and is complementary to a portion of an exonic region (e.g., 1, 2, 3, 4, 5, 6, 7, 8, 9, 10, 11, 12, 13, 14, 15, 16, 17, 18, 19, 20, 21, 22, 23, 24 or 25 nucleotides) and a portion of an intronic region (e.g., 8, 9, 10, 11, 12, 13, 14, 15, 16, 17, 18, 19, 20, 21, 22, 23, 24 or 25 nucleotides) of the pre-processed mRNA. Exemplary targeting sequences of the above types are listed below as SEQ ID NOs 17-34.

Selected antisense targeting sequences can be made shorter, e.g., about 12 bases, or longer, e.g., about 40 bases, and include a small number of mismatches, as long as the sequence is sufficiently complementary to effect splicing, and/or other form of inhibition upon hybridization with the target, and forms with the target RNA, a heteroduplex having a Tm of 45° C. or greater.

In certain embodiments, the degree of complementarity between the target and antisense targeting sequence is sufficient to form a stable duplex. The region of complementarity of the antisense oligomers with the target RNA sequence may be as short as 8-11 bases, but is preferably 12-15 bases or more, e.g., 12-20 bases, 12-25, or 15-25 bases, including all integers and ranges in between these ranges. An antisense oligomer of about 14-15 bases is generally long enough to have a unique complementary sequence in the target mRNA. In certain embodiments, a minimum length of complementary bases may be required to achieve the requisite binding Tm, as discussed below.

In certain embodiments, oligomers as long as 40 bases may be suitable, where at least a minimum number of bases, e.g., 10-12 bases, are complementary to the target sequence. In general, however, facilitated or active uptake in cells is optimized at oligomer lengths less than about 30. For PMO oligomers, described further below, an optimum balance of binding stability and uptake generally occurs at lengths of 18-30 bases. Included are antisense oligomers (e.g., PNAs, LNAs, 2'-OMe, MOE, PMOs) that consist of about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 bases, in which at least about 6, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 contiguous and/or non-contiguous bases are complementary to a target sequence described herein, including the target sequences of SEQ ID NOs: 1 and/or 2, or variants thereof.

In certain embodiments, antisense oligomers may be 100% complementary to the LMNA pre-mRNA nucleic acid target sequence, or they may include mismatches, e.g., to accommodate variants, as long as a heteroduplex formed between the oligomer and the target sequence is sufficiently stable to withstand the action of cellular nucleases and other modes of degradation or displacement which may occur in vivo. Oligomer backbones which are less susceptible to cleavage by nucleases are discussed below. Mismatches, if present, are less destabilizing toward the end regions of the hybrid duplex than in the middle. The number of mismatches allowed will depend on the length of the oligomer, the percentage of G:C base pairs in the duplex, and the position of the mismatch(es) in the duplex, according to well understood principles of duplex stability. Although such an antisense oligomer is not necessarily 100% complementary to the target sequence, it is effective to stably and specifically bind to the target sequence, such that a biological activity of the nucleic acid target, e.g., expression of the progerin protein(s), is modulated.

The stability of the duplex formed between an oligomer and a target sequence is a function of the binding Tm and the susceptibility of the duplex to cellular enzymatic cleavage. The Tm of an antisense compound with respect to complementary-sequence RNA may be measured by conventional methods, such as those described by Hames et al., Nucleic Acid Hybridization, IRL Press, 1985, pp. 107-108 or as described in Miyada C. G. and Wallace R. B., 1987, Oligonucleotide hybridization techniques, Methods Enzymol. Vol. 154 pp. 94-107. In certain embodiments, antisense oligomer may have a binding Tm, with respect to a complementary-sequence RNA, of greater than body temperature and preferably greater than 50° C. Tm's in the range 60-80° C. or greater are preferred. According to well known principles, the Tm of an oligomer compound, with respect to a complementary-based RNA hybrid, can be increased by increasing the ratio of C:G paired bases in the duplex, and/or by increasing the length (in base pairs) of the heteroduplex. At the same time, for purposes of optimizing cellular uptake, it may be advantageous to limit the size of the oligomer. For this reason, compounds that show high Tm (50° C. or greater) at a length of 25 bases or less are generally preferred over those requiring greater than 25 bases for high Tm values.

Figure 1B:
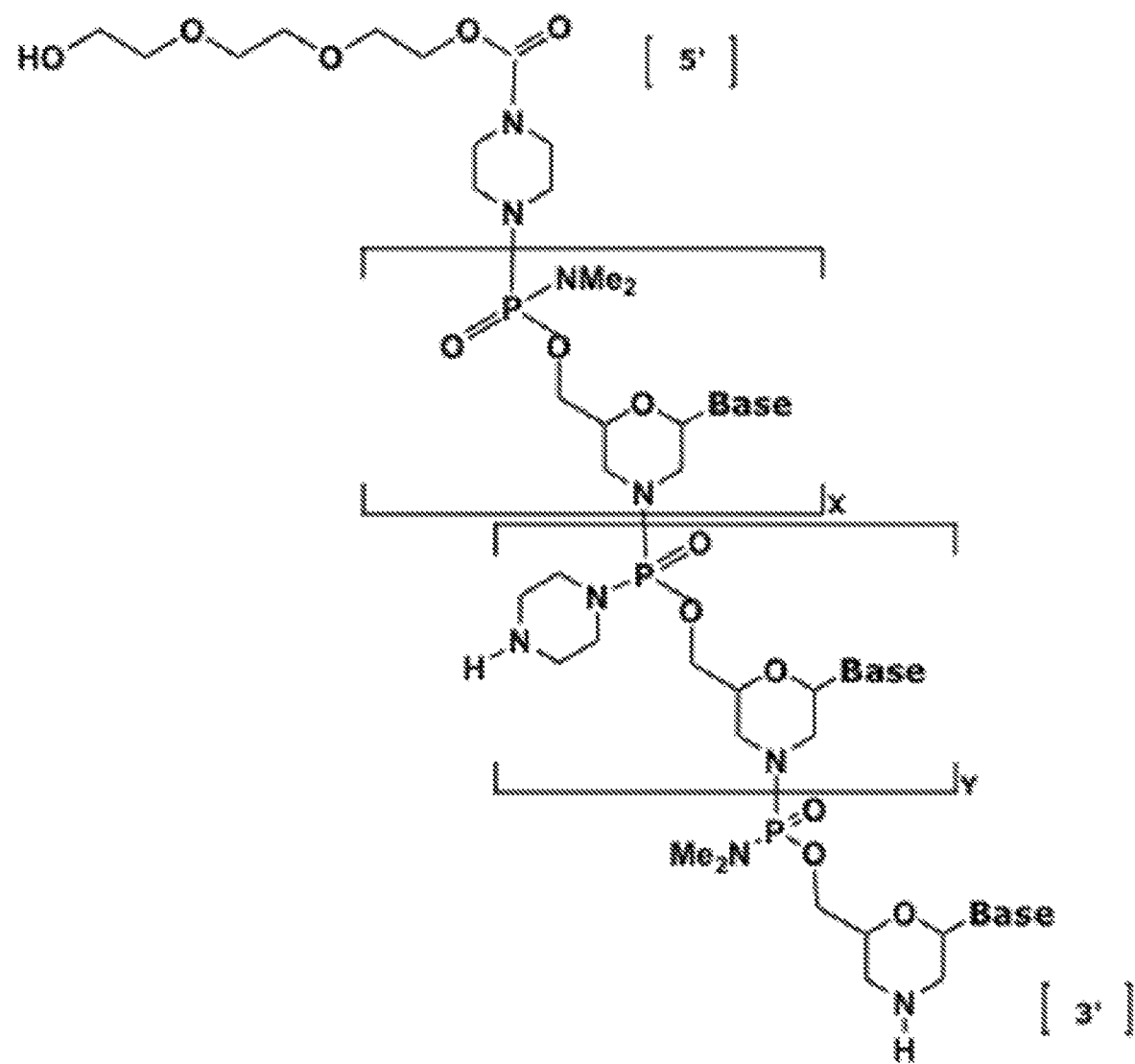
FIG. 1B shows a morpholino oligomer as in FIG. 1A, but where the backbone linkages contain one positively charged group in the form of a (piperazino) phosphorodiamidate linkage.
Figure 1C:
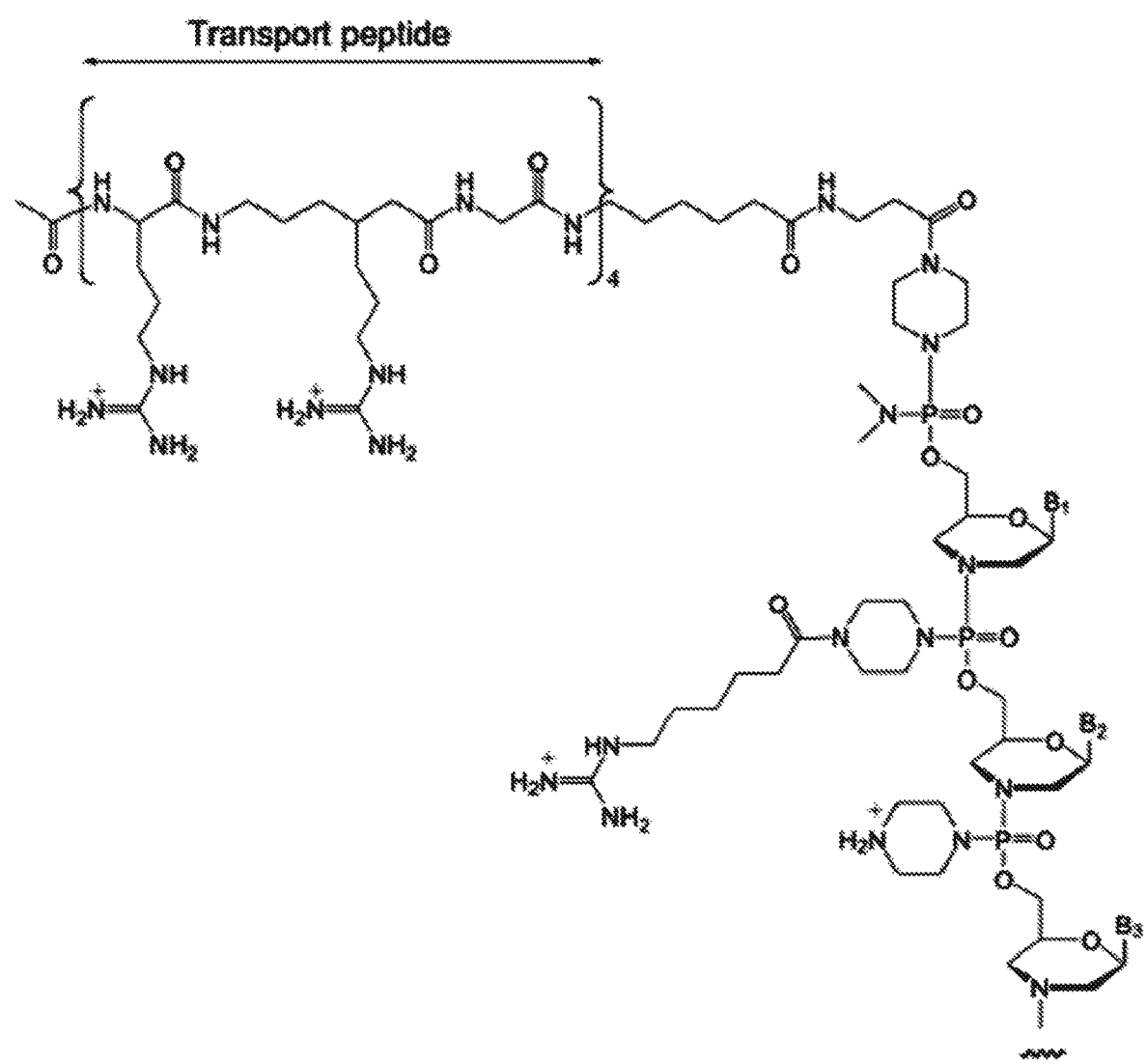
FIG. 1C shows a conjugate of an arginine-rich peptide and an antisense oligomer, in accordance with one embodiment of the invention.

In certain embodiments, such as PMO oligomers, the antisense activity of an oligomer may be enhanced by using a mixture of uncharged and cationic phosphorodiamidate linkages, as exemplified in FIG. 1C. The total number of cationic linkages in the oligomer can vary from 1 to 10 (including all integers in between), and be interspersed throughout the oligomer. Preferably the number of charged linkages is at least 2 and no more than half the total backbone linkages, e.g., between 2, 3, 4, 5, 6, 7, or 8 positively charged linkages, and preferably each charged linkage is separated along the backbone by at least 1, 2, 3, 4, or 5 uncharged linkages. A preferred cationic linkage of the invention includes the apn linkage B10 as shown in Table 3.

Exemplary antisense sequences for targeting the human LMNA pre-mRNA are shown in Table 1 below. Antisense oligonucleotides can comprise all or a portion of these targeting sequences.

TABLE 2

Exemplary HGPS Targeting Sequences*

| PMO name | Targeting Sequence 5'-3' | SEQ ID NO: |
|---|---|---|
| Exo11.25.133 | CCGCTGGCAGATGCCTTGTCGGCAG | 3 |
| Exo11.25.138 | CTGAGCCGCTGGCAGATGCCTTGTC | 4 |
| Exo11.25.142 | GCTCCTGAGCCGCTGGCAGATGCCT | 5 |
| Exo11.25.145 | TGGGCTCCTGAGCCGCTGGCAGATG | 6 |
| Exo11.25.149 | CACCTGGGCTCCTGAGCCGCTGGCA | 7 |
| Exo11.25.154 | CCACCCACCTGGGCTCCTGAGCCGC | 8 |
| Exo11.25.158 | GGGTCCACCCACCTGGGCTCCTGAG | 9 |
| Exo11.25.162 | AGATGGGTCCACCCACCTGGGCTCC | 10 |
| Exo11.25.166 | GAGGAGATGGGTCCACCCACCTGGG | 11 |
| Exo11.25.170 | GCCAGAGGAGATGGGTCCACCCACC | 12 |
| Exo11.25.174 | AAGAGCCAGAGGAGATGGGTCCACC | 13 |
| Exo11.25.177 | CAGAAGAGCCAGAGGAGATGGGTCC | 14 |
| Exo11.25.181 | GAGGCAGAAGAGCCAGAGGAGATGG | 15 |
| Exo11.25.185 | ACTGGAGGCAGAAGAGCCAGAGGAG | 16 |
| Exo10SD.25.69 | ACGTGGTGGTGATGGAGCAGGTCAT | 17 |
| Exo10SD.25.73 | ACTCACGTGGTGGTGATGGAGCAGG | 18 |
| Exo10SD.25.79 | GCTACCACTCACGTGGTGGTGATGG | 19 |

TABLE 2-continued

Exemplary HGPS Targeting Sequences*

| PMO name | Targeting Sequence 5'-3' | SEQ ID NO: |
|---|---|---|
| Exo10SD.25.84 | CGGCGGCTACCACTCACGTGGTGGT | 20 |
| Exo10SD.25.87 | CAGCGGCGGCTACCACTCACGTGGT | 21 |
| Exo10SD.25.90 | CCTCAGCGGCGGCTACCACTCACGT | 22 |
| Exo10SD.25.92 | GGCCTCAGCGGCGGCTACCACTCAC | 23 |
| Exo10SD.25.96 | GCTCGGCCTCAGCGGCGGCTACCAC | 24 |
| Exo11SA.25.779 | CGAGTCTGGGACTGACCACTCAGGC | 25 |
| Exo11SA.25.796 | AGGCTCAGGCGGGACGGCGAGTCTG | 26 |
| Exo11SA.25.801 | AGACAAGGCTCAGGCGGGACGGCGA | 27 |
| Exo11SA.25.805 | AGGGAGACAAGGCTCAGGCGGGACG | 28 |
| Exo11SA.25.809 | GGGAAGGGAGACAAGGCTCAGGCGG | 29 |
| Exo11SA.25.814 | GCCCTGGGAAGGGAGACAAGGCTCA | 30 |
| Exo11SA.25.820 | GTGGGAGCCCTGGGAAGGGAGACAA | 31 |
| Exo11SA.25.828 | CTGCTGCAGTGGGAGCCCTGGGAAG | 32 |
| Exo11SA.25.830 | AGCTGCTGCAGTGGGAGCCCTGGGA | 33 |
| Exo11SA.25.836 | CCCCCGAGCTGCTGCAGTGGGAGCC | 34 |
| HsEx10 | GCTACCACTCACGTGGTGGTGATGG-AcR$_6$G | 35 |
| HsEx11 | GGGTCCACCCACCTGGGCTCCTGAG-AcR$_6$G | 36 |
| HsEx10-apn | GC$^{apn}$TACCAC$^{apn}$TCACG$^{apn}$TGGTGG$^{apn}$TGATGG | 37 |
| HsEx11-apn | GGG$^{apn}$TCCACCCACC$^{apn}$TGGGC$^{apn}$TCC$^{apn}$TGAG | 38 |

*AcR$_6$G denotes a preferred cell-penetrating peptide transporter (acylated R$_6$; SEQ ID NO 45) conjugated with a glycine linker to the 3' end of an exemplary targeting sequence.
The $^{apn}$T in SEQ ID NOs 19 and 20 refer to an apn intersubunit linkage as further described below in Table 3, linkage B10.

Antisense Oligonucleotide Compounds

The antisense oligonucleotides of the present invention typically (a) have the ability to be actively taken up by mammalian cells, and (b) once taken up, form a duplex with the target RNA with a Tm greater than about 45° C. In certain embodiments, the oligomer backbone may be substantially uncharged, and, preferably, may be recognized as a substrate for active or facilitated transport across the cell membrane. The ability of the oligomer to form a stable duplex with the target RNA may also relate to other features of the oligomer backbone, including the length and degree of complementarity of the antisense oligomer with respect to the target, the ratio of G:C to A:T base matches, and the positions of any mismatched bases. The ability of the antisense oligomer to resist cellular nucleases may promote survival and ultimate delivery of the agent to the cell cytoplasm. Included are antisense oligomers composed of PMO, PMO+(PMOplus), PMO-X, LNA, PNAs, and/or 2'O-Me-based chemistries, described herein. In general, PNA and LNA chemistries utilize shorter targeting oligomers due to their relatively high target binding strength compared to PMO and 2'O-Me oligomers.

Peptide nucleic acids (PNAs) are analogs of DNA in which the backbone is structurally homomorphous with a deoxyribose backbone, consisting of N-(2-aminoethyl) glycine units to which pyrimidine or purine bases are attached. PNAs containing natural pyrimidine and purine bases hybridize to complementary oligonucleotides obeying Watson-Crick base-pairing rules, and mimic DNA in terms of base pair recognition (Egholm, Buchardt et al. 1993). The backbone of PNAs is formed by peptide bonds rather than phosphodiester bonds, making them well-suited for antisense applications (see structure below). The backbone is uncharged, resulting in PNA/DNA or PNA/RNA duplexes that exhibit greater than normal thermal stability. PNAs are not recognized by nucleases or proteases.

PNAs are produced synthetically using any technique known in the art. PNA is a DNA analog in which a polyamide backbone replaces the traditional phosphate ribose ring of DNA as shown below.

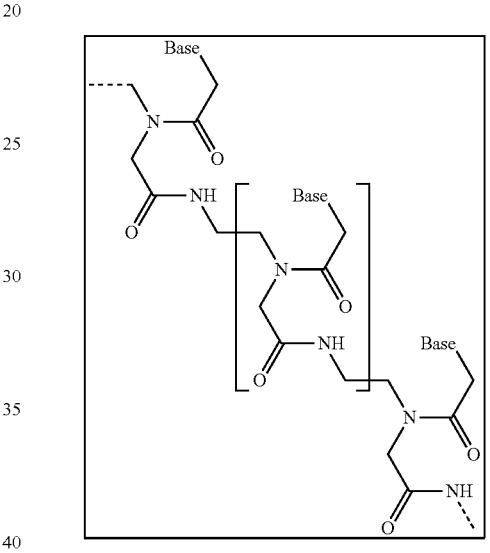

Despite a radical structural change to the natural RNA or DNA structure, PNA is capable of sequence-specific binding in a helix form to DNA or RNA. Characteristics of PNA include a high binding affinity to complementary DNA or RNA, a destabilizing effect caused by single-base mismatch, resistance to nucleases and proteases, hybridization with DNA or RNA independent of salt concentration and triplex formation with homopurine DNA. Panagene™ has developed its proprietary Bts PNA monomers (Bts; benzothiazole-2-sulfonyl group) and proprietary oligomerisation process. The PNA oligomerisation using Bts PNA monomers is composed of repetitive cycles of deprotection, coupling and capping. Panagene's patents to this technology include U.S. Pat. Nos. 6,969,766, 7,211,668, 7,022,851, 7,125,994, 7,145,006 and 7,179,896. Representative United States patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al., Science, 1991, 254, 1497.

Oligonucleotide compounds may also contain "locked nucleic acid" subunits (LNAs). The structures of LNAs are known in the art: for example, Wengel, et al., Chemical Communications (1998) 455; Tetrahedron (1998) 54, 3607, and Accounts of Chem. Research (1999) 32, 301); Obika, et al., Tetrahedron Letters (1997) 38, 8735; (1998) 39, 5401, and Bioorganic Medicinal Chemistry (2008)16, 9230. Exemplary, non-limiting LNA structures are illustrated below:

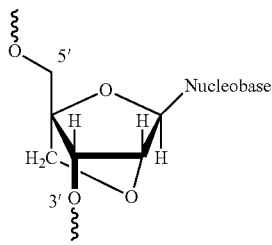

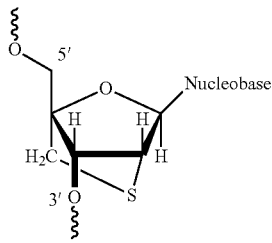

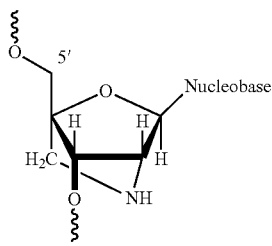

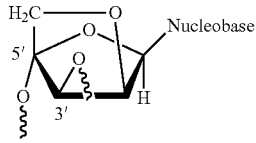

Compounds of the invention may incorporate one or more LNAs; in some cases, the compounds may be entirely composed of LNAs. Methods for the synthesis of individual LNA nucleoside subunits and their incorporation into oligonucleotides are known in the art: U.S. Pat. Nos. 7,572,582; 7,569,575; 7,084,125; 7,060,809; 7,053,207; 7,034,133; 6,794,499; and 6,670,461. Typical intersubunit linkers include phosphodiester and phosphorothioate moieties; alternatively, non-phosphorous containing linkers may be employed. A preferred embodiment is an LNA containing compound where each LNA subunit is separated by a DNA subunit (i.e., a deoxyribose nucleotide). Further preferred compounds are composed of alternating LNA and DNA subunits where the intersubunit linker is phosphorothioate.

A preferred oligomer structure employs morpholino-based subunits bearing base-pairing moieties, joined by uncharged linkages, as described above. Especially preferred is a substantially uncharged phosphorodiamidate-linked morpholino oligomer (PMO). Morpholino oligonucleotides, including antisense oligomers, are detailed, for example, in co-owned U.S. Pat. Nos. 5,698,685, 5,217,866, 5,142,047, 5,034,506, 5,166,315, 5,185,444, 5,521,063, and 5,506,337, and in PCT application No. U.S. Ser. No. 08/088,339, all of which are incorporated by reference.

Certain properties of the morpholino-based subunits include: the ability to be linked in a oligomeric form by stable, uncharged backbone linkages; the ability to support a nucleotide base (e.g., adenine, cytosine, guanine or uracil) such that the polymer formed can hybridize with a complementary-base target nucleic acid, including target RNA, with high Tm, even with oligomers as short as 10-14 bases; the ability of the oligomer to be actively transported into mammalian cells; and the ability of the oligomer:RNA heteroduplex to resist RNase degradation.

Properties of the morpholino-based subunits include: 1) the ability to be linked in a oligomeric form by stable, uncharged or positively charged backbone linkages; 2) the ability to support a nucleotide base (e.g., adenine, cytosine, guanine, thymidine, uracil and hypoxanthine) such that the polymer formed can hybridize with a complementary-base target nucleic acid, including target RNA, Tm values above about 45° C. in relatively short oligonucleotides (e.g., 10-15 bases); 3) the ability of the oligonucleotide to be actively or passively transported into mammalian cells; and 4) the ability of the antisense oligonucleotide:RNA heteroduplex to resist RNase and RNaseH degradation, respectively.

Figure 1D:
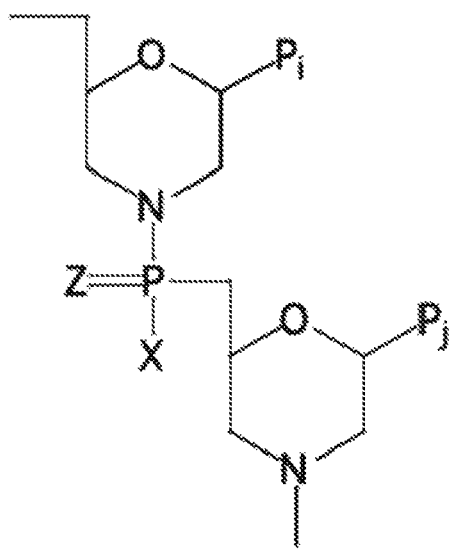
FIGS. 1D-G show the repeating subunit segment of exemplary morpholino oligonucleotides, designated D through G.
Figure 1E:
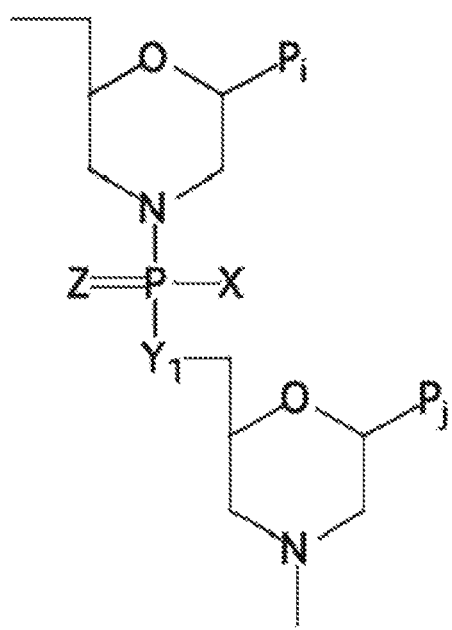

Examples of morpholino oligonucleotides having phosphorus-containing backbone linkages are illustrated in FIGS. 1A-1C. A preferred phosphorodiamidate-linked morpholino oligonucleotide is shown in FIG. 1C, which is modified, in accordance with one aspect of the present invention, to contain positively charged groups at preferably 10%-50% of its backbone linkages. Exemplary backbone structures for antisense oligonucleotides of the claimed subject matter include the morpholino subunit types shown in FIGS. 1A-1C, each linked by an uncharged or positively charged, phosphorus-containing subunit linkage. FIG. 1D shows a phosphorus-containing linkage which forms the five atom repeating-unit backbone, where the morpholino rings are linked by a 1-atom phosphoamide linkage. FIG. 1E shows a linkage which produces a 6-atom repeating-unit backbone. In this structure, the atom Y linking the 5' morpholino carbon to the phosphorus group may be sulfur, nitrogen, carbon or, preferably, oxygen. The X moiety pendant from the phosphorus may be fluorine, an alkyl or substituted alkyl, an alkoxy or substituted alkoxy, a thioalkoxy or substituted thioalkoxy, or unsubstituted, mono-substituted, or disubstituted nitrogen, including cyclic structures, such as morpholines or piperidines. Alkyl, alkoxy and thioalkoxy preferably include 1-6 carbon atoms. The Z moieties are sulfur or oxygen, and are preferably oxygen.

Figure 1F:
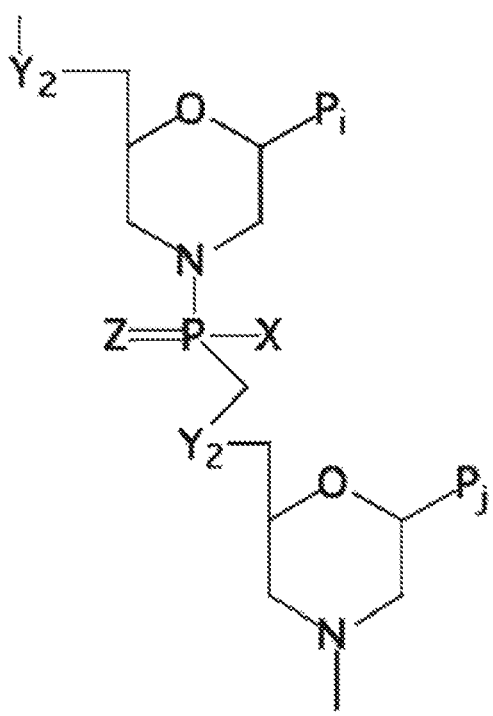
Figure 1G:
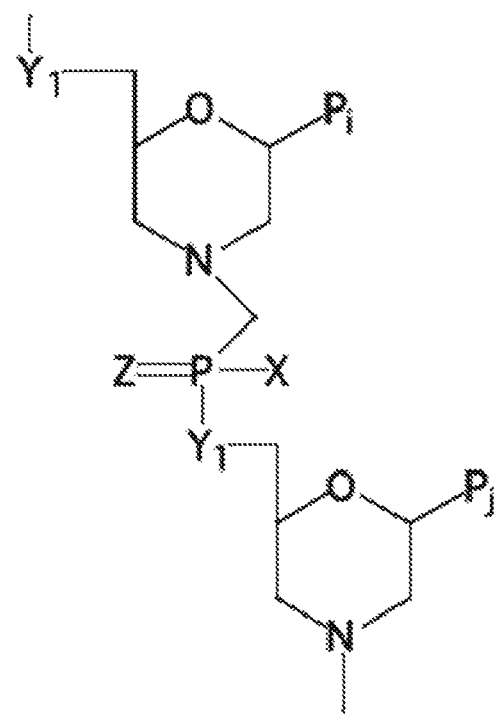

The linkages shown in FIGS. 1F and 1G are designed for 7-atom unit-length backbones. In FIG. 1F, the X moiety is as in FIG. 1E, and the Y moiety may be methylene, sulfur, or, preferably, oxygen. In FIG. 1G, the X and Y moieties are as FIG. 1E. Particularly preferred morpholino oligonucleotides include those composed of morpholino subunit structures of the form shown in FIG. 1E, where X=NH$_2$, N(CH$_3$)$_2$, or 1-piperazine or other charged group, Y=O, and Z=O.

As noted above, the substantially uncharged oligonucleotide may be modified, in accordance with an aspect of the invention, to include charged linkages, e.g., up to about 1 per every 2-5 uncharged linkages, such as about 4-5 per every 10 uncharged linkages. In certain embodiments, optimal improvement in antisense activity may be seen when about 25% of the backbone linkages are cationic. In certain embodiments, enhancement may be seen with a small number e.g., 10-20% cationic linkages, or where the number of cationic linkages are in the range 50-80%, such as about 60%. The enhancement seen with added cationic backbone charges may, in some cases, be further enhanced by distributing the bulk of the charges close of the "center-region" backbone linkages of the antisense oligonucleotide, e.g., in a 20-mer oligonucleotide with 8 cationic backbone linkages, having at least 70% of these charged linkages localized in the 10 centermost linkages.

In certain embodiments, the antisense compounds can be prepared by stepwise solid-phase synthesis, employing methods detailed in the references cited above, and below with respect to the synthesis of oligonucleotides having a mixture or uncharged and cationic backbone linkages. In some cases, it may be desirable to add additional chemical moieties to the antisense compound, e.g., to enhance pharmacokinetics or to facilitate capture or detection of the compound. Such a moiety may be covalently attached, typically to a terminus of the oligomer, according to standard synthetic methods. For example, addition of a polyethyleneglycol moiety or other hydrophilic polymer, e.g., one having 10-100 monomeric subunits, may be useful in enhancing solubility. One or more charged groups, e.g., anionic charged groups such as an organic acid, may enhance cell uptake.

A reporter moiety, such as fluorescein or a radiolabeled group, may be attached for purposes of detection. Alternatively, the reporter label attached to the oligomer may be a ligand, such as an antigen or biotin, capable of binding a labeled antibody or streptavidin. In selecting a moiety for attachment or modification of an antisense compound, it is generally of course desirable to select chemical compounds of groups that are biocompatible and likely to be tolerated by a subject without undesirable side effects.

As noted above, certain of the antisense compounds can be constructed to contain a selected number of cationic linkages interspersed with uncharged linkages of the type described above. The intersubunit linkages, both uncharged and cationic, preferably are phosphorus-containing linkages, having the structure:

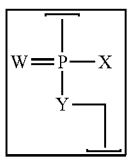

where
W is S or O, and is preferably O,
$X=NR^1R^2$ or $OR^6$,
$Y=O$ or $NR^7$,
and each said linkage in the oligomer is selected from:
(a) uncharged linkage (a), where each of $R^1$, $R^2$, $R^6$ and $R^7$ is independently selected from hydrogen and lower alkyl;
(b1) cationic linkage (b1), where $X=NR^1R^2$ and $Y=O$, and $NR^1R^2$ represents an optionally substituted piperazino group, such that $R^1R^2=-CHRCHRN(R^3)(R^4)CHRCHR-$, where
each R is independently H or $CH_3$,
$R^4$ is H, $CH_3$, or an electron pair, and
$R^3$ is selected from H, lower alkyl, e.g., $CH_3$, $C(=NH)NH_2$, Z-L-NHC($=NH)NH_2$, and $[C(O)CHR'NH]_mH$, where: Z is C(O) or a direct bond, L is an optional linker up to 18 atoms in length, preferably up to 12 atoms, and more preferably up to 8 atoms in length, having bonds selected from alkyl, alkoxy, and alkylamino, R' is a side chain of a naturally occurring amino acid or a one- or two-carbon homolog thereof, and m is 1 to 6, preferably 1 to 4;

(b2) cationic linkage (b2), where $X=NR^1R^2$ and $Y=O$, $R^1=H$ or $CH_3$, and $R^2=LNR^3R^4R^5$, where L, $R^3$, and $R^4$ are as defined above, and $R^5$ is H, lower alkyl, or lower (alkoxy)alkyl; and (b3) cationic linkage (b3), where $Y=NR^7$ and $X=OR^6$, and $R^7=LNR^3R^4R^5$, where L, $R^3$, $R^4$ and $R^5$ are as defined above, and $R^6$ is H or lower alkyl;

and at least one said linkage is selected from cationic linkages (b1), (b2), and (b3).

In certain embodiments, an oligomer may include at least two consecutive linkages of type (a) (i.e. uncharged linkages). In further embodiments, at least 5% of the linkages in the oligomer are cationic linkages (i.e. type (b1), (b2), or (b3)); for example, 10% to 60%, and preferably 20-50% linkages may be cationic linkages.

In one embodiment, at least one linkage is of type (b1), where, preferably, each R is H, $R^4$ is H, $CH_3$, or an electron pair, and $R^3$ is selected from H, lower alkyl, e.g., $CH_3$, $C(=NH)NH_2$, and $C(O)$-L-NHC($=NH)NH_2$. The latter two embodiments of $R^3$ provide a guanidino moiety, either attached directly to the piperazine ring, or pendant to a linker group L, respectively. For ease of synthesis, the variable Z in $R^3$ is preferably C(O) (carbonyl), as shown.

The linker group L, as noted above, contains bonds in its backbone selected from alkyl (e.g., $-CH_2-CH_2-$), alkoxy ($-C-O-$), and alkylamino (e.g., $-CH_2-NH-$), with the proviso that the terminal atoms in L (e.g., those adjacent to carbonyl or nitrogen) are carbon atoms. Although branched linkages (e.g., $-CH_2-CHCH_3-$) are possible, the linker is preferably unbranched. In one embodiment, the linker is a hydrocarbon linker. Such a linker may have the structure $-(CH_2)_n-$, where n is 1-12, preferably 2-8, and more preferably 2-6.

The morpholino subunits may have the structure:

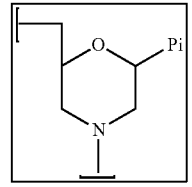

(i)

where Pi is a base-pairing moiety, and the linkages depicted above connect the nitrogen atom of (i) to the 5' carbon of an adjacent subunit. The base-pairing moieties Pi may be the same or different, and are generally designed to provide a sequence which binds to a target nucleic acid. The use of embodiments of linkage types (b1), (b2) and (b3) above to link morpholino subunits may be illustrated graphically as follows:

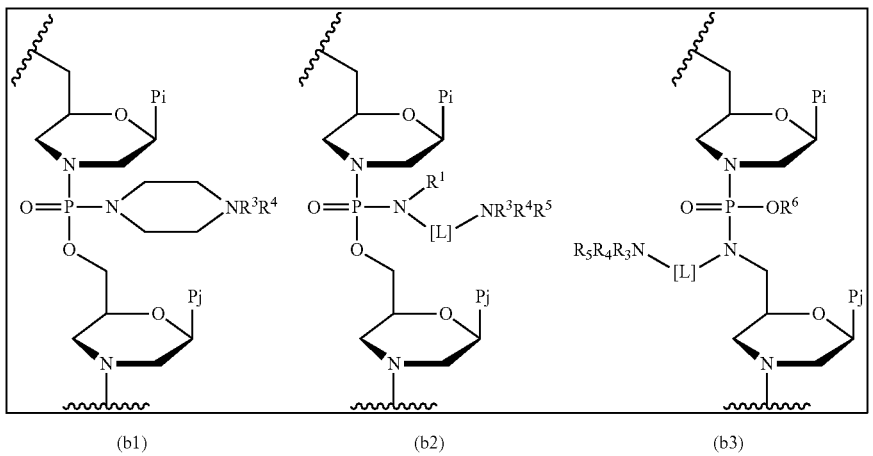

(b1)    (b2)    (b3)

Preferably, all cationic linkages in the oligomer are of the same type; i.e. all of type (b1), all of type (b2), or all of type (b3).

In further embodiments, the cationic linkages are selected from linkages (b1') and (b1″) as shown below, where (b1″) is referred to herein as a "Pip" linkage and (b1″) is referred to herein as a "GuX" linkage:

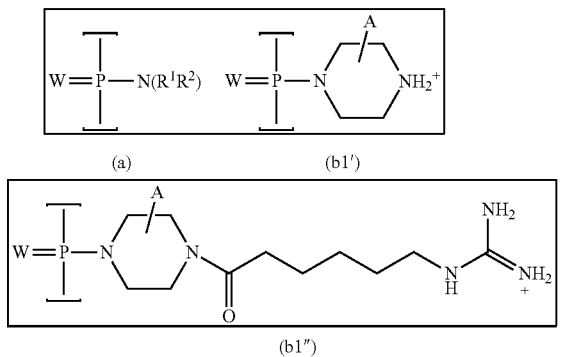

(a)    (b1')

(b1″)

In the structures above, W is S or O, and is preferably O; each of $R^1$ and $R^2$ is independently selected from hydrogen and lower alkyl, and is preferably methyl; and A represents hydrogen or a non-interfering substituent on one or more carbon atoms in (b1') and (b1″). Preferably, the ring carbons in the piperazine ring are unsubstituted; however, they may include non-interfering substituents, such as methyl or fluorine. Preferably, at most one or two carbon atoms is so substituted. In further embodiments, at least 10% of the linkages are of type (b1') or (b1″); for example, 10%-60% and preferably 20% to 50%, of the linkages may be of type (b1') or (b1″).

In certain embodiments, the oligomer contains no linkages of the type (b1') above. Alternatively, the oligomer contains no linkages of type (b 1) where each R is H, $R^3$ is H or $CH_3$, and $R^4$ is H, $CH_3$, or an electron pair.

The morpholino subunits may also be linked by non-phosphorus-based intersubunit linkages, as described further below, where at least one linkage is modified with a pendant cationic group as described above.

Other oligonucleotide analog linkages which are uncharged in their unmodified state but which could also bear a pendant amine substituent could be used. For example, a 5'nitrogen atom on a morpholino ring could be employed in a sulfamide linkage or a urea linkage (where phosphorus is replaced with carbon or sulfur, respectively) and modified in a manner analogous to the 5'-nitrogen atom in structure (b3) above.

Oligomers having any number of cationic linkages are provided, including fully cationic-linked oligomers. Preferably, however, the oligomers are partially charged, having, for example, 10%-80%. In preferred embodiments, about 10% to 60%, and preferably 20% to 50% of the linkages are cationic.

In one embodiment, the cationic linkages are interspersed along the backbone. The partially charged oligomers preferably contain at least two consecutive uncharged linkages; that is, the oligomer preferably does not have a strictly alternating pattern along its entire length.

Also considered are oligomers having blocks of cationic linkages and blocks of uncharged linkages; for example, a central block of uncharged linkages may be flanked by blocks of cationic linkages, or vice versa. In one embodiment, the oligomer has approximately equal-length 5', 3' and center regions, and the percentage of cationic linkages in the center region is greater than about 50%, preferably greater than about 70%.

Oligomers for use in antisense applications generally range in length from about 10 to about 40 subunits, more preferably about 10 to 30 subunits, and typically 15-25 bases. For example, an oligomer of the invention having 19-20 subunits, a useful length for an antisense compound, may ideally have two to ten, e.g., four to eight, cationic linkages, and the remainder uncharged linkages. An oligomer having 14-15 subunits may ideally have two to seven, e.g., 3, 4, or 5, cationic linkages and the remainder uncharged linkages.

Each morpholino ring structure supports a base pairing moiety, to form a sequence of base pairing moieties which is typically designed to hybridize to a selected antisense target in a cell or in a subject being treated. The base pairing moiety may be a purine or pyrimidine found in native DNA or RNA (e.g., A, G, C, T or U) or an analog, such as hypoxanthine (the base component of the nucleoside inosine) or 5-methyl cytosine.

As noted above, certain embodiments are directed to oligomers comprising novel intersubunit linkages, including PMO-X oligomers and those having modified terminal groups. In some embodiments, these oligomers have higher affinity for DNA and RNA than do the corresponding unmodified oligomers and demonstrate improved cell delivery, potency, and/or tissue distribution properties compared to oligomers having other intersubunit linkages. In one embodiment, the oligomers comprise at least one intersubunit linkage of type (B) as defined herein. The oligomers may also comprise one or more intersubunit linkages of type (A) as defined herein. The structural features and properties of the various linkage types and oligomers are described in more detail in the following discussion. The synthesis of these and related oligomers is described in co-owned U.S. application Ser. No. 13/118,298, which is incorporated by reference in its entirety.

Linkage (A)

Applicants have found that enhancement of antisense activity, biodistribution and/or other desirable properties can be optimized by preparing oligomers having various intersubunit linkages. For example, the oligomers may optionally comprise one or more intersubunit linkages of type (A), and in certain embodiments the oligomers comprise at least one linkage of type (A). In some other embodiments each linkage of type (A) has the same structure. Linkages of type (A) may include linkages disclosed in co-owned U.S. Pat. No. 7,943,762 which is hereby incorporated by reference in its entirety. Linkage (A) has the following structure (I), wherein 3' and 5' indicate the point of attachment to the 3' and 5' ends, respectively, of the morpholino ring (i.e., structure (i) discussed below):

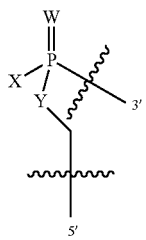

I or a salt or isomer thereof, wherein:

W is, at each occurrence, independently S or O;

X is, at each occurrence, independently —N(CH$_3$)$_2$, —NR$^1$R$^2$, —OR$^3$ or;

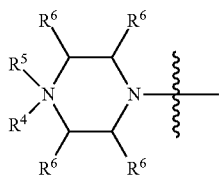

(II)

Y is, at each occurrence, independently O or —NR$^2$,

R$^1$ is, at each occurrence, independently hydrogen or methyl;

R$^2$ is, at each occurrence, independently hydrogen or -LNR$^4$R$^5$R$^7$;

R$^3$ is, at each occurrence, independently hydrogen or C$_1$-C$_6$ alkyl;

R$^4$ is, at each occurrence, independently hydrogen, C$_1$-C$_6$ alkyl, —C(=NH)NH$_2$, —Z-L-NHC(=NH)NH$_2$ or —[C(=O)CHR'NH]$_m$H, where Z is —C(=O)— or a direct bond, R' is a side chain of a naturally occurring amino acid or a one- or two-carbon homolog thereof, and m is 1 to 6;

R$^5$ is, at each occurrence, independently hydrogen, methyl or an electron pair;

R$^6$ is, at each occurrence, independently hydrogen or methyl;

R$^7$ is, at each occurrence, independently hydrogen C$_1$-C$_6$ alkyl or C$_1$-C$_6$ alkoxyalkyl; and L is an optional linker up to 18 atoms in length comprising alkyl, alkoxy or alkylamino groups, or combinations thereof.

In some examples, the oligomer comprises at least one linkage of type (A). In some other embodiments, the oligomer includes at least two consecutive linkages of type (A). In further embodiments, at least 5% of the linkages in the oligomer are type (A); for example in some embodiments, 5%-95%, 10% to 90%, 10% to 50%, or 10% to 35% of the linkages may be linkage type (A). In some specific embodiments, at least one type (A) linkage is —N(CH$_3$)$_2$. In other embodiments, each linkage of type (A) is —N(CH$_3$)$_2$. In other embodiments, at least one type (A) linkage is piperizin-1-yl, for example unsubstituted piperazin-1-yl (e.g., A2 or A3). In other embodiments, each linkage of type (A) is piperizin-1-yl, for example unsubstituted piperazin-1-yl.

In some embodiments, W is, at each occurrence, independently S or O, and in certain embodiments W is O.

In some embodiments, X is, at each occurrence, independently —N(CH$_3$)$_2$, —NR$^1$R$^2$, —OR$^3$. In some embodiments X is —N(CH$_3$)$_2$. In other aspects X is —NR$^1$R$^2$, and in other examples X is —OR$^3$.

In some embodiments, R$^1$ is, at each occurrence, independently hydrogen or methyl. In some embodiments, R$^1$ is hydrogen. In other embodiments X is methyl.

In some embodiments, R$^2$ is, at each occurrence, hydrogen. In other embodiments R$^2$ is, at each occurrence, -LNR$^4$R$^5$R$^7$. In some embodiments, R$^3$ is, at each occurrence, independently hydrogen or C$_1$-C$_6$ alkyl. In other embodiments, R$^3$ is methyl. In yet other embodiments, R$^3$ is ethyl. In some other embodiments, R$^3$ is n-propyl or isopropyl. In some other embodiments, R$^3$ is C$_4$ alkyl. In other embodiments, R$^3$ is C$_5$ alkyl. In some embodiments, R$^3$ is C$_6$ alkyl.

In certain embodiments, R$^4$ is, at each occurrence, independently hydrogen. In other embodiments, R$^4$ is methyl or ethyl. In yet other embodiments, R$^4$ is —C(=NH)NH$_2$, and in other embodiments, R$^4$ is —Z-L-NHC(=NH)NH$_2$. In still other embodiments, R$^4$ is —[C(=O)CHR'NH]$_m$H. Z is —C(=O)— in one embodiment and Z is a direct bond in another embodiment. R' is a side chain of a naturally occurring amino acid. In some embodiments R' is a one- or two-carbon homolog of a side chain of a naturally occurring amino acid.

m is and integer from 1 to 6. m may be 1. m may be 2 m may be 3 m may be 4 m may be 5 m may be 6

In some embodiments, R$^5$ is, at each occurrence, independently hydrogen, methyl or an electron pair. In some embodiments, R$^5$ is hydrogen. In other embodiments, R$^5$ is methyl. In yet other embodiments, R$^5$ is an electron pair.

In some embodiments, R$^6$ is, at each occurrence, independently hydrogen or methyl. In some embodiments, R$^6$ is hydrogen. In other embodiments, R$^6$ is methyl.

In other embodiments, R$^7$ is, at each occurrence, independently hydrogen C$_1$-C$_6$ alkyl or C$_2$-C$_6$ alkoxyalkyl. In some embodiments R7 is hydrogen. In other embodiments, R$^7$ is C$_1$-C$_6$ alkyl. In yet other embodiments, R$^7$ is C$_2$-C$_6$ alkoxyalkyl. In some embodiments, R$^7$ is methyl. In other embodiments, R$^7$ is ethyl. In yet other embodiments, R$^7$ is n-propyl or isopropyl. In some other embodiments, R$^7$ is C$_4$ alkyl. In some embodiments, $R^7$ is $C_5$ alkyl. In some embodiments, $R^7$ is $C_6$ alkyl. In yet other embodiments, $R^7$ is $C_2$ alkoxyalkyl. In some other embodiments, $R^7$ is $C_3$ alkoxyalkyl. In yet other embodiments, $R^7$ is $C_4$ alkoxyalkyl. In some embodiments, $R^7$ is $C_5$ alkoxyalkyl. In other embodiments, $R^7$ is $C_6$ alkoxyalkyl.

The linker group L, as noted above, contains bonds in its backbone selected from alkyl (e.g. —CH2-CH2-), alkoxy (e.g., —C—O—C—), and alkylamino (e.g. —CH2-NH—), with the proviso that the terminal atoms in L (e.g., those adjacent to carbonyl or nitrogen) are carbon atoms. Although branched linkages (e.g. —CH2-CHCH3-) are possible, the linker is generally unbranched. In one embodiment, the linker is a hydrocarbon linker. Such a linker may have the structure $(CH2)_n$-, where n is 1-12, preferably 2-8, and more preferably 2-6.

Oligomers having any number of linkage type (A) are provided. In some embodiments, the oligomer contains no linkages of type (A). In certain embodiments, 5, 10, 20, 30, 40, 50, 60, 70, 80 or 90 percent of the linkages are linkage (A). In selected embodiments, 10 to 80, 20 to 80, 20 to 60, 20 to 50, 20 to 40, or 20 to 35 percent of the linkages are linkage (A).

Linkage (B)

In some embodiments, the oligomers comprise at least one linkage of type (B).

For example the oligomers may comprise 1, 2, 3, 4, 5, 6 or more linkages of type (B). The type (B) linkages may be adjacent or may be interspersed throughout the oligomer. Linkage type (B) has the following structure (I):

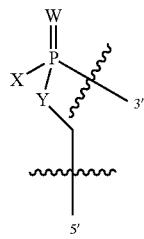

(I)

or a salt or isomer thereof, wherein:

W is, at each occurrence, independently S or O;

X is, at each occurrence, independently —NR⁸R⁹ or —OR³; and

Y is, at each occurrence, independently O or —NR¹⁰, $R^3$ is, at each occurrence, independently hydrogen or $C_1$-$C_6$ alkyl;

$R^8$ is, at each occurrence, independently hydrogen or $C_2$-$C_{12}$ alkyl;

$R^9$ is, at each occurrence, independently hydrogen, $C_1$-$C_{12}$ alkyl, $C_1$-$C_{12}$ aralkyl or aryl;

$R^{10}$ is, at each occurrence, independently hydrogen, $C_1$-$C_{12}$ alkyl or -LNR⁴R⁵R⁷;

wherein $R^8$ and $R^9$ may join to form a 5-18 membered mono or bicyclic heterocycle or $R^8$, $R^9$ or $R^3$ may join with $R^{10}$ to form a 5-7 membered heterocycle, and wherein when X is 4-piparazino, X has the following structure (III):

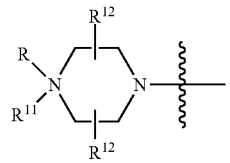

(III)

wherein:

$R^{11}$ is, at each occurrence, independently $C_2$-$C_{12}$ alkyl, $C_1$-$C_{12}$ aminoalkyl, $C_1$-$C_{12}$ alkylcarbonyl, aryl, heteroaryl or heterocyclyl;

R is, at each occurrence, independently an electron pair, hydrogen or $C_1$-$C_{12}$ alkyl; and $R^{12}$ is, at each occurrence, independently, hydrogen, $C_1$-$C_{12}$ alkyl, $C_1$-$C_{12}$ aminoalkyl, —NH₂, —NR¹³R¹⁴, —NR¹³R¹⁴R¹⁵, $C_1$-$C_{12}$ alkylcarbonyl, oxo, —CN, trifluoromethyl, amidyl, amidinyl, amidinylalkyl, amidinylalkylcarbonyl guanidinyl, guanidinylalkyl, guanidinylalkylcarbonyl, cholate, deoxycholate, aryl, heteroaryl, heterocycle, —SR¹³ or $C_1$-$C_{12}$ alkoxy, wherein $R^{13}$, $R^{14}$ and $R^{15}$ are, at each occurrence, independently $C_1$-$C_{12}$ alkyl.

In some examples, the oligomer comprises one linkage of type (B). In some other embodiments, the oligomer comprises two linkages of type (B). In some other embodiments, the oligomer comprises three linkages of type (B). In some other embodiments, the oligomer comprises four linkages of type (B). In still other embodiments, the linkages of type (B) are consecutive (i.e., the type (B) linkages are adjacent to each other). In further embodiments, at least 5% of the linkages in the oligomer are type (B); for example in some embodiments, 5%-95%, 10% to 90%, 10% to 50%, or 10% to 35% of the linkages may be linkage type (B).

In other embodiments, $R^3$ is, at each occurrence, independently hydrogen or $C_1$-$C_6$ alkyl. In yet other embodiments, $R^3$ may be methyl. In some embodiments, $R^3$ may be ethyl. In some other embodiments, $R^3$ may be n-propyl or isopropyl. In yet other embodiments, $R^3$ may be $C_4$ alkyl. In some embodiments, $R^3$ may be $C_5$ alkyl. In some embodiments, $R^3$ may be $C_6$ alkyl.

In some embodiments, $R^8$ is, at each occurrence, independently hydrogen or $C_2$-$C_{12}$ alkyl. In some embodiments, $R^8$ is hydrogen. In yet other embodiments, $R^8$ is ethyl. In some other embodiments, $R^8$ is n-propyl or isopropyl. In some embodiments, $R^8$ is $C_4$ alkyl. In yet other embodiments, $R^8$ is $C_5$ alkyl. In other embodiments, $R^8$ is $C_6$ alkyl. In some embodiments, $R^8$ is $C_7$ alkyl. In yet other embodiments, $R^8$ is $C_8$ alkyl. In other embodiments, $R^8$ is $C_9$ alkyl. In yet other embodiments, $R^8$ is $C_{10}$ alkyl. In some other embodiments, $R^8$ is $C_{11}$ alkyl. In yet other embodiments, $R^8$ is $C_{12}$ alkyl. In some other embodiments, $R^8$ is $C_2$-$C_{12}$ alkyl and the $C_2$-$C_{12}$ alkyl includes one or more double bonds (e.g., alkene), triple bonds (e.g., alkyne) or both. In some embodiments, $R^8$ is unsubstituted $C_2$-$C_{12}$ alkyl.

In some embodiments, $R^9$ is, at each occurrence, independently hydrogen, $C_1$-$C_{12}$ alkyl, $C_1$-$C_{12}$ aralkyl or aryl. In some embodiments, $R^9$ is hydrogen. In yet other embodiments, $R^9$ is $C_1$-$C_{12}$ alkyl. In other embodiments, $R^9$ is methyl. In yet other embodiments, $R^9$ is ethyl. In some other embodiments, $R^9$ is n-propyl or isopropyl. In some embodiments, $R^9$ is $C_4$ alkyl. In some embodiments, $R^9$ is $C_5$ alkyl. In yet other embodiments, $R^9$ is $C_6$ alkyl. In some other embodiments, $R^9$ is $C_7$ alkyl. In yet other embodiments, $R^9$ is $C_8$ alkyl. In some other embodiments, $R^9$ is $C_9$ alkyl. In some other embodiments, $R^9$ is $C_{10}$ alkyl. In some other embodiments, $R^9$ is $C_{11}$ alkyl. In yet other embodiments, $R^9$ is $C_{12}$ alkyl.

In some other embodiments, $R^9$ is $C_1$-$C_{12}$ aralkyl. For example, n some embodiments $R^9$ is benzyl and the benzyl may be optionally substituted on either the phenyl ring or the benzylic carbon. Substituents in this regards include alkyl and alkoxy groups, for example methyl or methoxy. In some embodiments, the benzyl group is substituted with methyl at the benzylic carbon. For example, in some embodiments, $R^9$ has the following structure (XIV):

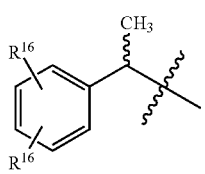

(XIV)

In other embodiments, $R^9$ is aryl. For example, in some embodiments $R^9$ is phenyl, and the phenyl may be optionally substituted. Substituents in this regard substituents include alkyl and alkoxy groups, for example methyl or methoxy. In other embodiments, $R^9$ is phenyl and the phenyl comprises a crown ether moiety, for example a 12-18 membered crown ether. In one embodiment the crown ether is 18 membered and may further comprise and additional phenyl moiety. For example, in one embodiment $R^9$ has one of the following structures (XV) or XVI):

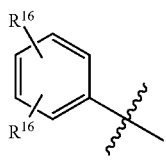

or

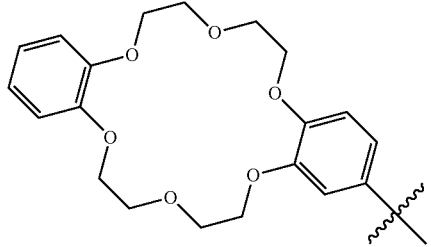

(XV)

(XVI)

In some embodiments, $R^{10}$ is, at each occurrence, independently hydrogen, $C_1$-$C_{12}$ alkyl or -$LNR^4R^5R^7$, wherein $R^4$, $R^5$ and $R^7$ are as defined above with respect to linkage (A). In other embodiments, $R^{10}$ is hydrogen. In other embodiments, $R^{10}$ is $C_1$-$C_{12}$ alkyl, and in other embodiments $R^{10}$ is -$LNR^4R^5R^7$. In some embodiments, $R^{10}$ is methyl. In yet other embodiments, $R^{10}$ is ethyl. In some embodiments, $R^{10}$ is $C_3$ alkyl. In some embodiments, $R^{10}$ is $C_4$ alkyl. In yet other embodiments, $R^{10}$ is $C_5$ alkyl. In some other embodiments, $R^{10}$ is $C_6$ alkyl. In other embodiments, $R^{10}$ is $C_7$ alkyl. In yet other embodiments, $R^{10}$ is $C_8$ alkyl. In some embodiments, $R^{10}$ is $C_9$ alkyl. In other embodiments, $R^{10}$ is $C_{10}$ alkyl. In yet other embodiments, $R^{10}$ is $C_{11}$ alkyl. In some other embodiments, $R^{10}$ is $C_{12}$ alkyl.

In some embodiments, $R^8$ and $R^9$ join to form a 5-18 membered mono or bicyclic heterocycle. In some embodiments the heterocycle is a 5 or 6 membered monocyclic heterocycle. For example, in some embodiments linkage (B) has the following structure (IV):

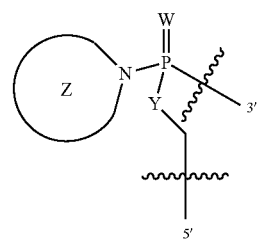

(IV)

In other embodiments, heterocycle is bicyclic, for example a 12-membered bicyclic heterocycle. The heterocycle may be piperizinyl. The heterocycle may be morpholino. The heterocycle may be piperidinyl. The heterocycle may be decahydroisoquinoline. Representative heterocycles include the following:

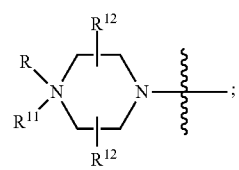

(III)

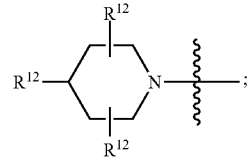

(V)

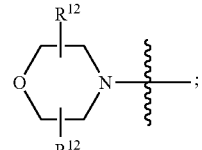

(VI)

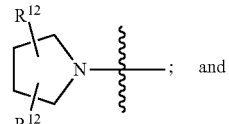

(VII)

and

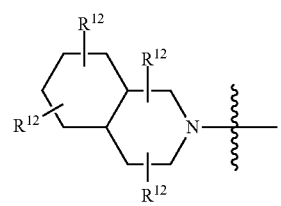

(VIII)

In some embodiments, $R^{11}$ is, at each occurrence, independently $C_2$-$C_{12}$ alkyl, $C_1$-$C_{12}$ aminoalkyl, aryl, heteroaryl or heterocyclyl.

In some embodiments, $R^{11}$ is $C_2$-$C_{12}$ alkyl. In some embodiments, $R^{11}$ is ethyl. In other embodiments, $R^{11}$ is $C_3$ alkyl. In yet other embodiments, $R^{11}$ is isopropyl. In some other embodiments, $R^{11}$ is $C_4$ alkyl. In other embodiments, $R^{11}$ is $C_5$ alkyl. In some embodiments, $R^{11}$ is $C_6$ alkyl. In other embodiments, $R^1$ is $C_7$ alkyl. In some embodiments, $R^{11}$ is $C_8$ alkyl. In other embodiments, $R^{11}$ is $C_9$ alkyl. In yet other embodiments, $R^{11}$ is $C_{10}$ alkyl. In some other embodiments, $R^{11}$ is $C_{11}$ alkyl. In some embodiments, $R^{11}$ is $C_{12}$ alkyl.

In other embodiments, $R^{11}$ is $C_1$-$C_{12}$ aminoalkyl. In some embodiments, $R^{11}$ is methylamino. In some embodiments, $R^{11}$ is ethylamino. In other embodiments, $R^{11}$ is $C_3$ aminoalkyl. In yet other embodiments, $R^{11}$ is $C_4$ aminoalkyl. In some other embodiments, $R^{11}$ is $C_5$ aminoalkyl. In other embodiments, $R^{11}$ is $C_6$ aminoalkyl. In yet other embodiments, $R^1$ is $C_7$ aminoalkyl. In some embodiments, $R^{11}$ is $C_8$ aminoalkyl. In other embodiments, $R^{11}$ is $C_9$ aminoalkyl. In yet other embodiments, $R^{11}$ is $C_{10}$ aminoalkyl. In some other embodiments, $R^{11}$ is $C_{11}$ aminoalkyl. In other embodiments, $R^{11}$ is $C_{12}$ aminoalkyl.

In other embodiments, $R^{11}$ is $C_1$-$C_{12}$ alkylcarbonyl. In yet other embodiments, $R^{11}$ is $C_1$ alkylcarbonyl. In other embodiments, $R^{11}$ is $C_2$ alkylcarbonyl. In some embodiments, $R^{11}$ is $C_3$ alkylcarbonyl. In yet other embodiments, $R^{11}$ is $C_4$ alkylcarbonyl. In some embodiments, $R^{11}$ is $C_5$ alkylcarbonyl. In some other embodiments, $R^{11}$ is $C_6$ alkylcarbonyl. In other embodiments, $R^{11}$ is $C_7$ alkylcarbonyl. In yet other embodiments, $R^{11}$ is $C_8$ alkylcarbonyl.

In some embodiments, $R^{11}$ is $C_9$ alkylcarbonyl. In yet other embodiments, $R^{11}$ is $C_{10}$ alkylcarbonyl. In some other embodiments, $R^{11}$ is $C_{11}$ alkylcarbonyl. In some embodiments, $R^{11}$ is $C_{12}$ alkylcarbonyl. In yet other embodiments, $R^{11}$ is $—C(=O)(CH_2)_nCO_2H$, where n is 1 to 6. For example, in some embodiments, n is 1. In other embodiments, n is 2. In yet other embodiments, n is 3. In some other embodiments, n is 4. In yet other embodiments, n is 5. In other embodiments, n is 6.

In other embodiments, $R^{11}$ is aryl. For example, in some embodiments, $R^{11}$ is phenyl. In some embodiments, the phenyl is substituted, for example with a nitro group.

In other embodiments, $R^{11}$ is heteroaryl. For example, in some embodiments, $R^{11}$ is pyridinyl. In other embodiments, $R^{11}$ is pyrimidinyl.

In other embodiments, $R^{11}$ is heterocyclyl. For example, in some embodiments, $R^{11}$ is piperidinyl, for example piperidin-4-yl.

In some embodiments, $R^{11}$ is ethyl, isopropyl, piperidinyl, pyrimidinyl, cholate, deoxycholate, or $—C(=O)(CH_2)_nCO_2H$, where n is 1 to 6.

In some embodiments, R is an electron pair. In other embodiments, R is hydrogen, and in other embodiments R is $C_1$-$C_{12}$ alkyl. In some embodiments, R is methyl. In some embodiments, R is ethyl. In other embodiments, R is $C_3$ alkyl. In yet other embodiments, R is isopropyl. In some other embodiments, R is $C_4$ alkyl. In yet other embodiments, R is $C_5$ alkyl. In some embodiments, R is $C_6$ alkyl. In other embodiments, R is $C_7$ alkyl. In yet other embodiments, R is $C_8$ alkyl. In other embodiments, R is $C_9$ alkyl. In some embodiments, R is $C_{10}$ alkyl. In yet other embodiments, R is $C_{11}$ alkyl. In some embodiments, R is $C_{12}$ alkyl.

In some embodiments, $R^{12}$ is, at each occurrence, independently, hydrogen, $C_1$-$C_{12}$ alkyl, $C_1$-$C_{12}$ aminoalkyl, $—NH_2$, $—NR^{13}R^{14}$, $—NR^{13}R^{14}R^{15}$, oxo, $—CN$, trifluoromethyl, amidyl, amidinyl, amidinylalkyl, amidinylalkylcarbonyl guanidinyl, guanidinylalkyl, guanidinylalkylcarbonyl, cholate, deoxycholate, aryl, heteroaryl, heterocycle, $—SR^{13}$ or $C_1$-$C_{12}$ alkoxy, wherein $R^{13}$, $R^{14}$ and $R^{15}$ are, at each occurrence, independently $C_1$-$C_{12}$ alkyl In some embodiments, $R^{12}$ is hydrogen. In some embodiments, $R^{12}$ is $C_1$-$C_{12}$ alkyl. In some embodiments, $R^{12}$ is $C_1$-$C_{12}$ aminoalkyl. In some embodiments, $R^{12}$ is $—NH_2$. In some embodiments, $R^{12}$ is $—NR^{13}R^{14}$. In some embodiments, $R^{12}$ is $—NR^{13}R^{14}R^{15}$. In some embodiments, $R^{12}$ is $C_1$-$C_{12}$ alkylcarbonyl. In some embodiments, $R^{12}$ is oxo. In some embodiments, $R^{12}$ is $—CN$. In some embodiments, $R^{12}$ is trifluoromethyl. In some embodiments, $R^{12}$ is amidyl. In some embodiments, $R^{12}$ is amidinyl. In some embodiments, $R^{12}$ is amidinylalkyl. In some embodiments, $R^{12}$ is amidinylalkylcarbonyl. In some embodiments, $R^{12}$ is guanidinyl, for example mono methylguanidynyl or dimethylguanidinyl. In some embodiments, $R^{12}$ is guanidinylalkyl. In some embodiments, $R^{12}$ is amidinylalkylcarbonyl. In some embodiments, $R^{12}$ is cholate. In some embodiments, $R^{12}$ is deoxycholate. In some embodiments, $R^{12}$ is aryl. In some embodiments, $R^{12}$ is heteroaryl. In some embodiments, $R^{12}$ is heterocycle. In some embodiments, $R^{12}$ is $—SR^{13}$. In some embodiments, $R^{12}$ is $C_1$-$C_{12}$ alkoxy. In some embodiments, $R^{12}$ is dimethyl amine.

In other embodiments, $R^{12}$ is methyl. In yet other embodiments, $R^{12}$ is ethyl. In some embodiments, $R^{12}$ is $C_3$ alkyl. In some embodiments, $R^{12}$ is isopropyl. In some embodiments, $R^{12}$ is $C_4$ alkyl. In other embodiments, $R^{12}$ is $C_5$ alkyl. In yet other embodiments, $R^{12}$ is $C_6$ alkyl. In some other embodiments, $R^{12}$ is $C_7$ alkyl. In some embodiments, $R^{12}$ is $C_8$ alkyl. In yet other embodiments, $R^{12}$ is $C_9$ alkyl. In some embodiments, $R^{12}$ is $C_{10}$ alkyl. In yet other embodiments, $R^{12}$ is $C_{11}$ alkyl. In other embodiments, $R^{12}$ is $C_{12}$ alkyl. In yet other embodiments, the alkyl moiety is substituted with one or more oxygen atom to form an ether moiety, for example a methoxymethyl moiety.

In some embodiments, $R^{12}$ is methylamino. In other embodiments, $R^{12}$ is ethylamino. In yet other embodiments, $R^{12}$ is $C_3$ aminoalkyl. In some embodiments, $R^{12}$ is $C_4$ aminoalkyl. In yet other embodiments, $R^{12}$ is $C_5$ aminoalkyl. In some other embodiments, $R^{12}$ is $C_6$ aminoalkyl. In some embodiments, $R^{12}$ is $C_7$ aminoalkyl. In some embodiments, $R^{12}$ is $C_8$ aminoalkyl. In yet other embodiments, $R^{12}$ is $C_9$ aminoalkyl. In some other embodiments, $R^{12}$ is $C_{10}$ aminoalkyl. In yet other embodiments, $R^{12}$ is $C_{11}$ aminoalkyl. In other embodiments, $R^{12}$ is $C_{12}$ aminoalkyl. In some embodiments, the amino alkyl is a dimethylamino alkyl.

In yet other embodiments, $R^{12}$ is acetyl. In some other embodiments, $R^{12}$ is $C_2$ alkylcarbonyl. In some embodiments, $R^{12}$ is $C_3$ alkylcarbonyl. In yet other embodiments, $R^{12}$ is $C_4$ alkylcarbonyl. In some embodiments, $R^{12}$ is $C_5$ alkylcarbonyl. In yet other embodiments, $R^{12}$ is $C_6$ alkylcarbonyl. In some other embodiments, $R^{12}$ is $C_7$ alkylcarbonyl. In some embodiments, $R^{12}$ is $C_8$ alkylcarbonyl. In yet other embodiments, $R^{12}$ is $C_9$ alkylcarbonyl. In some other embodiments, $R^{12}$ is $C_{10}$ alkylcarbonyl. In some embodiments, $R^{12}$ is $C_{11}$ alkylcarbonyl. In other embodiments, $R^{12}$ is $C_{12}$ alkylcarbonyl. The alkylcarbonyl is substituted with a carboxy moiety, for example the alkylcarbonyl is substituted to form a succinic acid moiety (i.e., a 3-carboxyalkylcarbonyl). In other embodiments, the alkylcarbonyl is substituted with a terminal $—SH$ group.

In some embodiments, $R^{12}$ is amidyl. In some embodiments, the amidyl comprises an alkyl moiety which is further substituted, for example with $—SH$, carbamate, or combinations thereof. In other embodiments, the amidyl is substituted with an aryl moiety, for example phenyl. In certain embodiments, $R^{12}$ may have the following structure (IX):

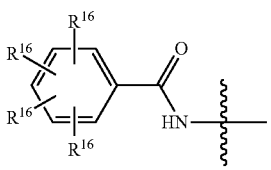

(IX)

wherein $R^{16}$ is, at each occurrence, independently hydrogen, $C_1$-$C_{12}$ alkyl, $C_1$-$C_{12}$ alkoxy, —CN, aryl or heteroaryl.

In some embodiments, $R^{12}$ is methoxy. In other embodiments, $R^{12}$ is ethoxy. In yet other embodiments, $R^{12}$ is $C_3$ alkoxy. In some embodiments, $R^{12}$ is $C_4$ alkoxy. In some embodiments, $R^{12}$ is $C_5$ alkoxy. In some other embodiments, $R^{12}$ is $C_6$ alkoxy. In other embodiments, $R^{12}$ is $C_7$ alkoxy. In some other embodiments, $R^{12}$ is $C_8$ alkoxy. In some embodiments, $R^{12}$ is $C_9$ alkoxy. In other embodiments, $R^{12}$ is $C_{10}$ alkoxy. In some embodiments, $R^{12}$ is $C_{11}$ alkoxy. In yet other embodiments, $R^{12}$ is $C_{12}$ alkoxy.

In certain embodiments, $R^{12}$ is pyrrolidinyl, for example pyrrolidin-1-yl. In other embodiments, $R^{12}$ is piperidinyl, for example piperidin-1-yl or piperidin-4-yl. In other embodiment, $R^{12}$ is morpholino, for example morpholin-4-yl. In other embodiments, $R^{12}$ is phenyl, and in even further embodiments, the phenyl is substituted, for example with a nitro group. In still other embodiments, $R^{12}$ is pyrimidinyl, for example pyrimidin-2-yl.

In other embodiments, $R^{13}$, $R^{14}$ and $R^{15}$ are, at each occurrence, independently $C_1$-$C_{12}$ alkyl. In some embodiments, $R^{13}$, $R^{14}$ or $R^{15}$ is methyl. In yet other embodiments, $R^{13}$, $R^{14}$ or $R^{15}$ is ethyl. In other embodiments, $R^{13}$, $R^{14}$ or $R^{15}$ is $C_3$ alkyl. In yet other embodiments, $R^{13}$, $R^{14}$ or $R^{15}$ is isopropyl. In other embodiments, $R^{13}$, $R^{14}$ or $R^{15}$ is $C_4$ alkyl. In some embodiments, $R^{13}$, $R^{14}$ or $R^{15}$ is $C_5$ alkyl. In some other embodiments, $R^{13}$, $R^{14}$ or $R^{15}$ is $C_6$ alkyl. In other embodiments, $R^{13}$, $R^{14}$ or $R^{15}$ is $C_7$ alkyl. In yet other embodiments, $R^{13}$, $R^{14}$ or $R^{15}$ is $C_8$ alkyl. In other embodiments, $R^{13}$, $R^{14}$ or $R^{15}$ is $C_9$ alkyl. In some embodiments, $R^{13}$, $R^{14}$ or $R^{15}$ is $C_{10}$ alkyl. In some embodiments, $R^{13}$, $R^{14}$ or $R^{15}$ is $C_{11}$ alkyl. In yet other embodiments, $R^{13}$, $R^{14}$ or $R^{15}$ is $C_{12}$ alkyl.

As noted above, in some embodiments, $R^{12}$ is amidyl substituted with an aryl moiety. In this regard, each occurrence of $R^{16}$ may be the same or different. In certain of these embodiments, $R^{16}$ is hydrogen. In other embodiments, $R^{16}$ is —CN. In other embodiments, $R^{16}$ is heteroaryl, for example tretrazolyl. In certain other embodiments, $R^{16}$ is methoxy. In other embodiments, $R^{16}$ is aryl, and the aryl is optionally substituted. Optional substituents in this regard include: $C_1$-$C_{12}$ alkyl, $C_1$-$C_{12}$ alkoxy, for example methoxy; trifluoromethoxy; halo, for example chloro; and trifluoromethyl.

In other embodiments, $R^{16}$ is methyl. In yet other embodiments, $R^{16}$ is ethyl. In some embodiments, $R^{16}$ is $C_3$ alkyl. In some other embodiments, $R^{16}$ is isopropyl. In yet other embodiments, $R^{16}$ is $C_4$ alkyl. In other embodiments, $R^{16}$ is $C_5$ alkyl. In yet other embodiments, $R^{16}$ is $C_6$ alkyl. In some other embodiments, $R^{16}$ is $C_7$ alkyl. In some embodiments, $R^{16}$ is $C_8$ alkyl. In yet other embodiments, $R^{16}$ is $C_9$ alkyl. In some other embodiments, $R^{16}$ is $C_{10}$ alkyl. In other embodiments, $R^{16}$ is $C_{11}$ alkyl. In some other embodiments, $R^{16}$ is $C_{12}$ alkyl.

In some embodiments, $R^{16}$ is methoxy. In some embodiments, $R^{16}$ is ethoxy. In yet other embodiments, $R^{16}$ is $C_3$ alkoxy. In some other embodiments, $R^{16}$ is $C_4$ alkoxy. In other embodiments, $R^{16}$ is $C_5$ alkoxy. In some other embodiments, $R^{16}$ is $C_6$ alkoxy. In yet other embodiments, $R^{16}$ is $C_7$ alkoxy. In some other embodiments, $R^{16}$ is $C_8$ alkoxy. In yet other embodiments, $R^{16}$ is $C_9$ alkoxy. In some other embodiments, $R^{16}$ is $C_{10}$ alkoxy. In some embodiments, $R^{16}$ is $C_{11}$ alkoxy. In some other embodiments, $R^{16}$ is $C_{12}$ alkoxy.

In some other embodiments, $R^8$ and $R^9$ join to form a 12-18 membered crown ether. For example, in some embodiments, the crown ether s 18 membered, and in other embodiments the crown ether is 15 membered. In certain embodiments, $R^8$ and $R^9$ join to form a heterocycle having one of the following structures (X) or (XI):

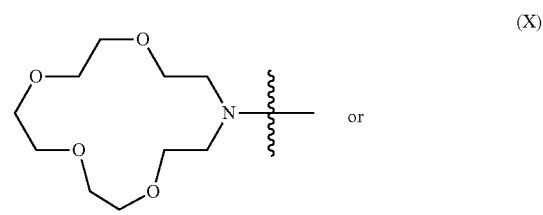

(X)

or

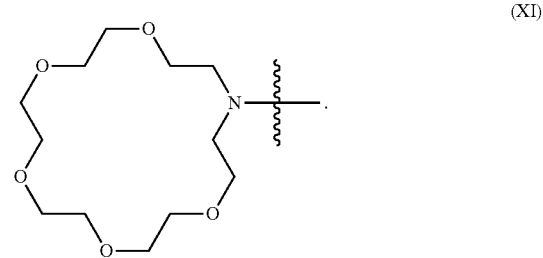

(XI)

In some embodiments, $R^8$, $R^9$ or $R^3$ join with $R^{10}$ to form a 5-7 membered heterocycle. For example, in some embodiments, $R^3$ joins with $R^{10}$ to form a 5-7 membered heterocycle. In some embodiments, the heterocycle is 5-membered. In other embodiments, the heterocycle is 6-membered. In other embodiments, the heterocycle is 7-membered. In some embodiments, the heterocycle is represented by the following structure (XII):

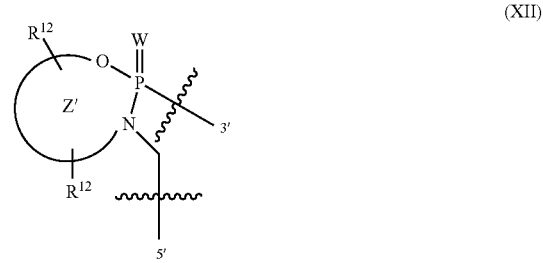

(XII)

wherein Z' represents a 5-7 membered heterocycle. In certain embodiments of structure (XI), $R^{12}$ is hydrogen at each occurrence. For example, linkage (B) may have one of the following structures (B1), (B2) or (B3):

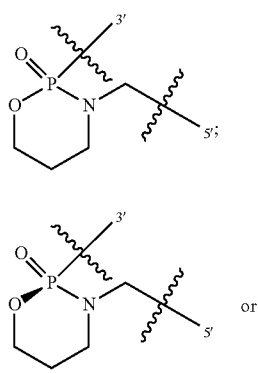

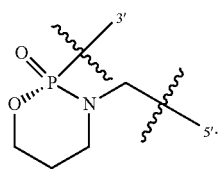

-continued (B3)

In certain other embodiments, $R^{12}$ is $C_1$-$C_{12}$ alkylcarbonyl or amidyl which is further substituted with an arylphosphoryl moiety, for example a triphenyl phosporyl moiety. Examples of linkages having this structure include B56 and B55.

In certain embodiment, linkage (B) does not have any of the structures A1-A5. Table 3 shows representative linkages of type (A) and (B).

TABLE 3

| | Representative Intersubunit Linkages | |
|---|---|---|
| No. | Name | Structure |
| A1 | PMO | |
| A2 | PMO⁺(unprotonated form depicted) | |
| A3 | PMO⁺ (+) | |
| A4 | PMO$^{mepip}$ (m+) | |

TABLE 3-continued

Representative Intersubunit Linkages

| No. | Name | Structure |
|---|---|---|
| A5 | PMO$^{GUX}$ | 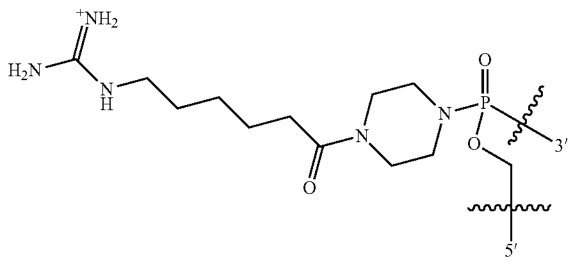 |
| B1 | PMO$^{cp}$ | 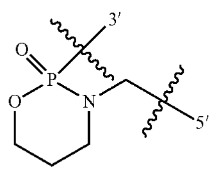 |
| B2 | PMO$^{cps}$ | 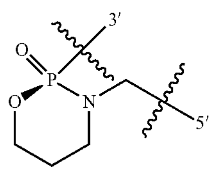 |
| B3 | PMO$^{cpr}$ | 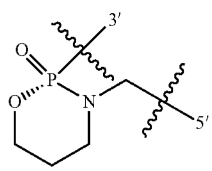 |
| B4 | PMO$^{Shc}$ | 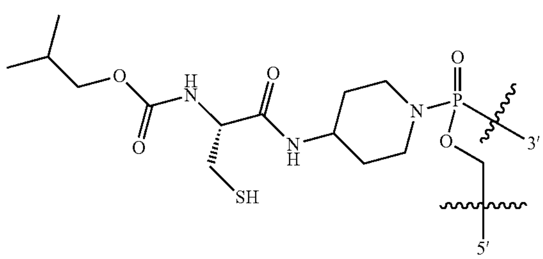 |
| B5 | PMO$^{morpholino}$ (m) | 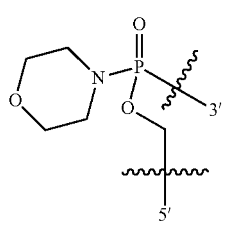 |
| B6 | PMO$^{pri}$ (t) | 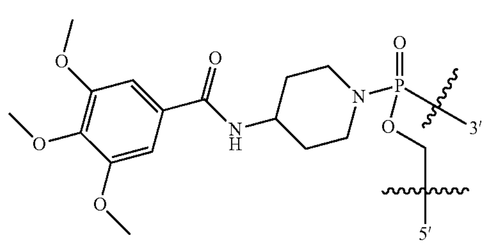 |

TABLE 3-continued

Representative Intersubunit Linkages

| No. | Name | Structure |
|---|---|---|
| B7 | PMO$^{hex}$ (h) | 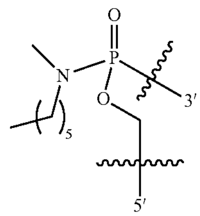 |
| B8 | PMO$^{dodec}$ | 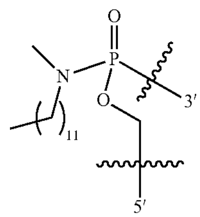 |
| B9 | PMO$^{dihex}$ | 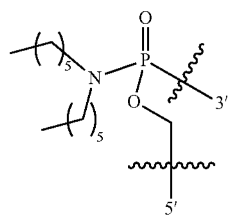 |
| B10 | PMO$^{apn}$ (a) | 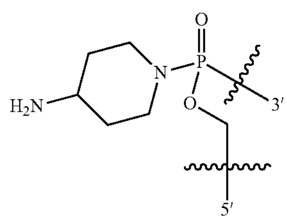 |
| B11 | PMO$^{pyr}$ (p) | 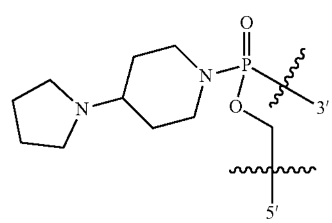 |
| B12 | PMO$^{pyr}$ (HCl Salt) | 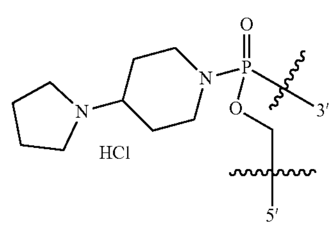 |
| B13 | PMO$^{rba}$ | 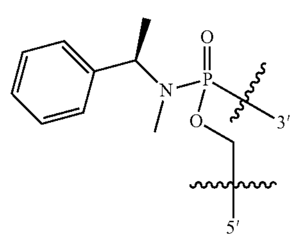 |

TABLE 3-continued
Representative Intersubunit Linkages
| No. | Name | Structure |
|---|---|---|
| B14 | PMO$^{sba}$ | 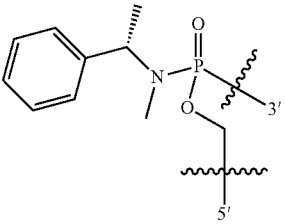 |
| B15 | PMO$^{dimethylapn}$ | 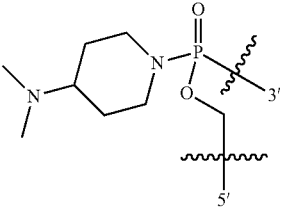 |
| B16 | PMO$^{etpip}$ | 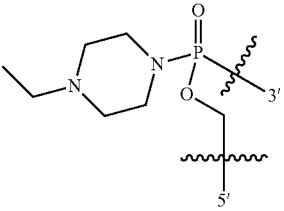 |
| B17 | PMO$^{iprpip}$ | 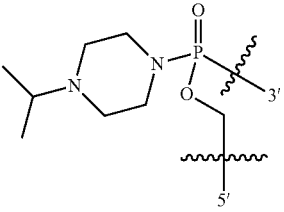 |
| B18 | PMO$^{pyrQMe}$ | 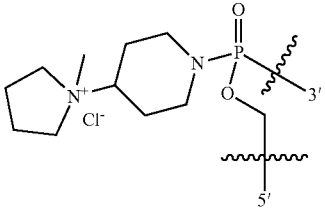 |
| B19 | PMO$^{cb}$ | 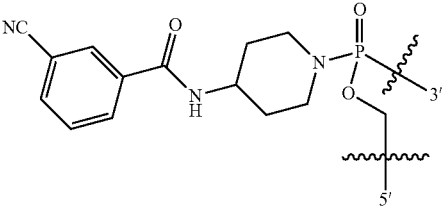 |

TABLE 3-continued
Representative Intersubunit Linkages
| No. | Name | Structure |
|---|---|---|
| B20 | PMO$^{ma}$ | 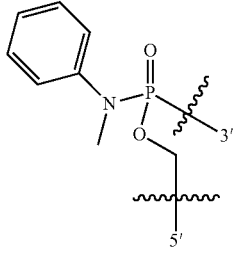 |
| B21 | PMO$^{bu}$ | 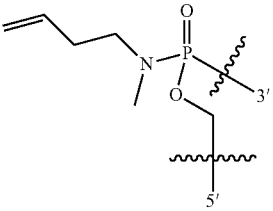 |
| B22 | PMO$^{bi}$ | 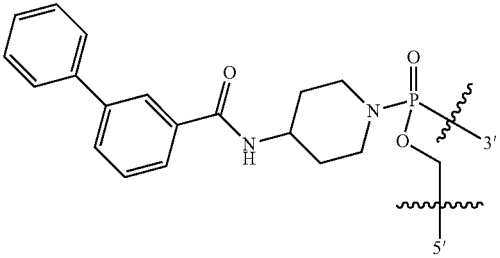 |
| B23 | PMO$^{pip}$ | 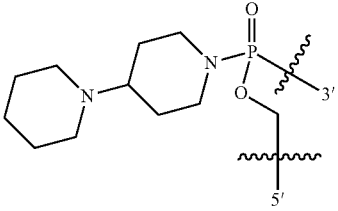 |
| B24 | PMO$^{odmb}$ | 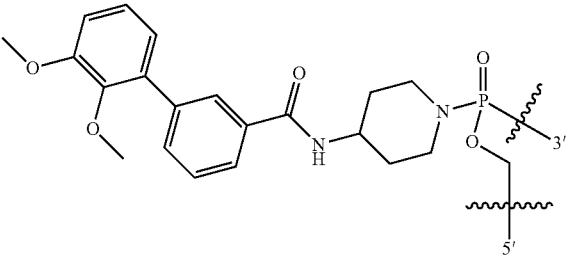 |
| B25 | PMO$^{tfb}$ | 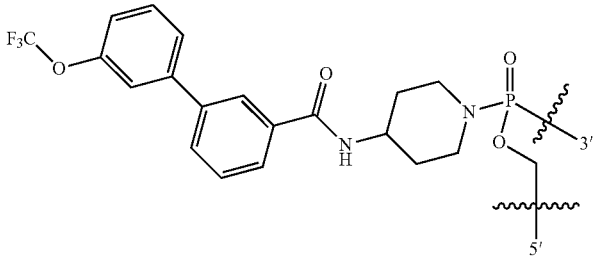 |

TABLE 3-continued
Representative Intersubunit Linkages
| No. | Name | Structure |
|---|---|---|
| B26 | PMO$^{ctfb}$ | 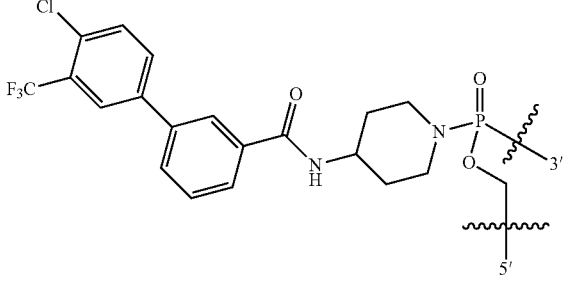 |
| B27 | PMO$^{ptfb}$ | 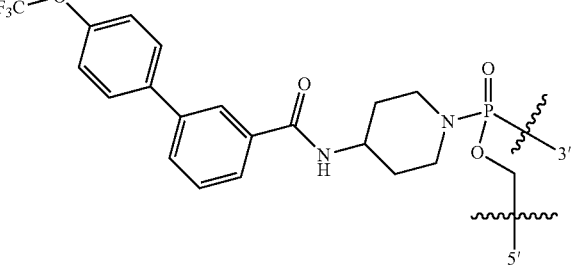 |
| B28 | PMO$^{dcb}$ | 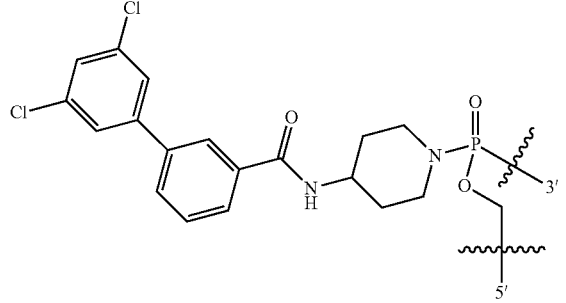 |
| B29 | PMO$^{dmb}$ | 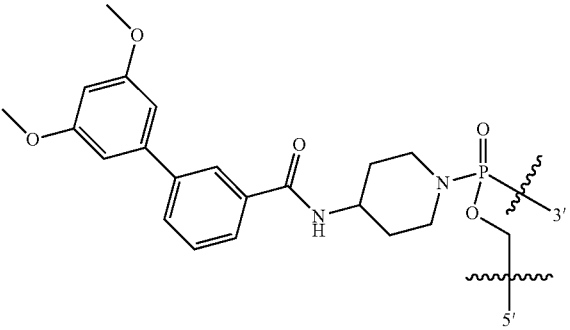 |
| B30 | PMO$^{hy}$ | 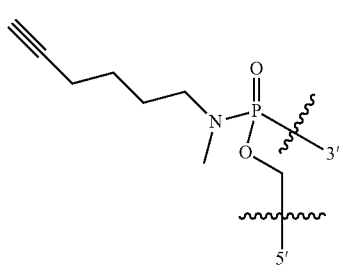 |

TABLE 3-continued

Representative Intersubunit Linkages

| No. | Name | Structure |
|---|---|---|
| B31 | PMO$^{6ce}$ | 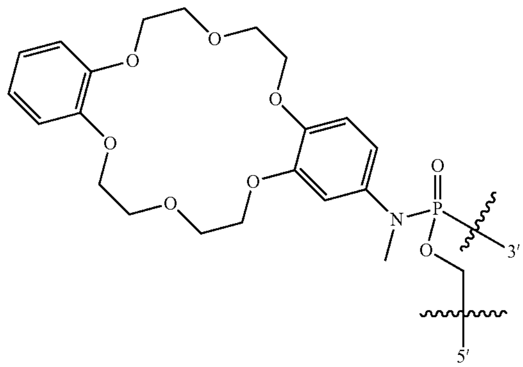 |
| B32 | PMO$^b$ | 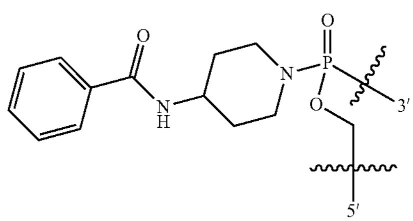 |
| B33 | PMO$^q$ | 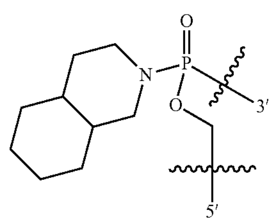 |
| B34 | PMO$^{npp}$ | 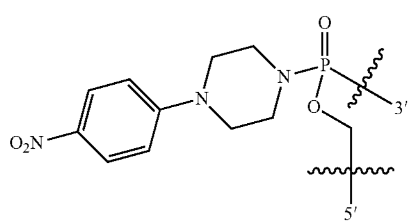 |
| B35 | PMO$^o$ | 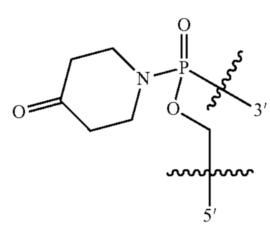 |
| B36 | PMO$^{4ce}$ | 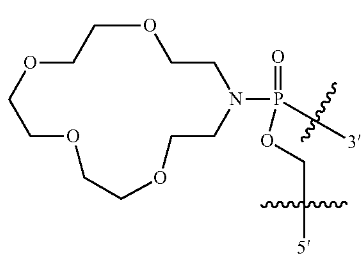 |

TABLE 3-continued

Representative Intersubunit Linkages

| No. | Name | Structure |
|---|---|---|
| B37 | PMO$^{5ce}$ | 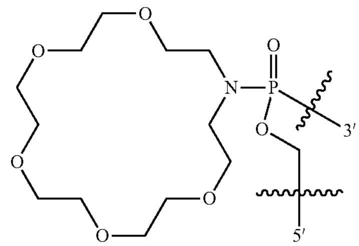 |
| B38 | PMO$^{f3p}$ | 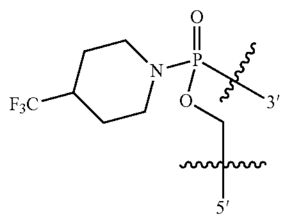 |
| B39 | PMO$^{cyp}$ | 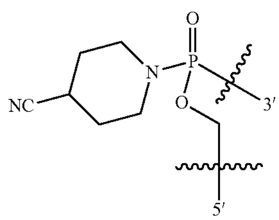 |
| B40 | PMO$^{mop}$ | 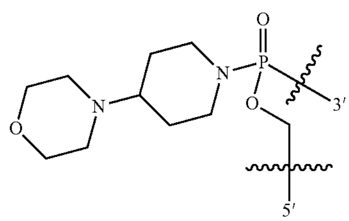 |
| B41 | PMO$^{pp}$ | 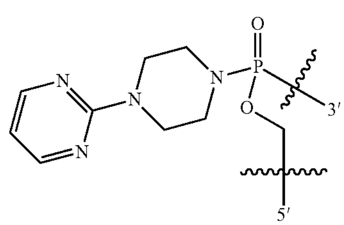 |
| B42 | PMO$^{dmepip}$ | 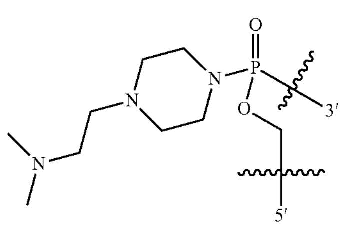 |

TABLE 3-continued

Representative Intersubunit Linkages

| No. | Name | Structure |
|-----|------|-----------|
| B43 | PMO$^{NPpip}$ | 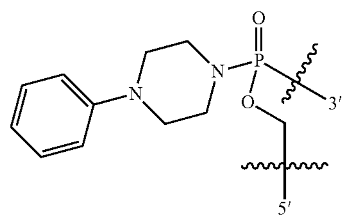 |
| B44 | PMO$^{bipip}$ | 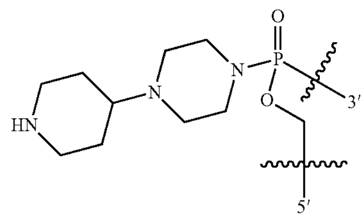 |
| B45 | PMO$^{suc}$ | 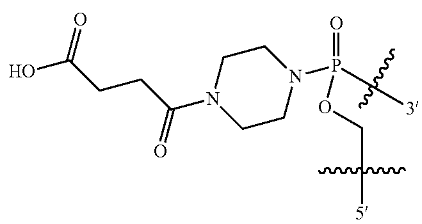 |
| 46 | PMO$^{glutaric}$ | 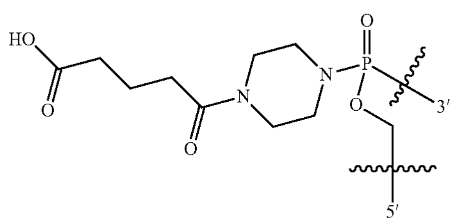 |
| B47 | PMO$^{tet}$ | 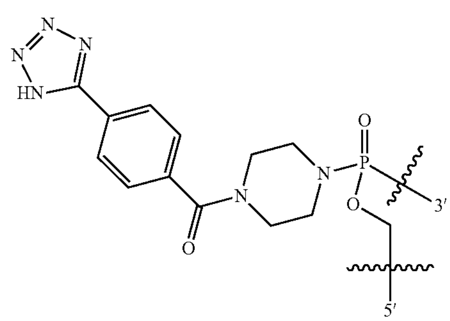 |
| B48 | PMO$^{thiol}$ (SH) | 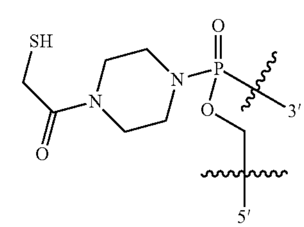 |

TABLE 3-continued

Representative Intersubunit Linkages

| No. | Name | Structure |
|---|---|---|
| B49 | PMO$^{pros}$ | 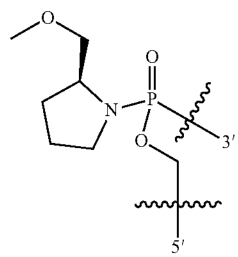 |
| B50 | PMO$^{pror}$ | 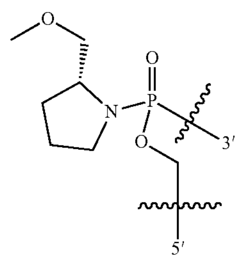 |
| B51 | PMO$^{tme}$ | 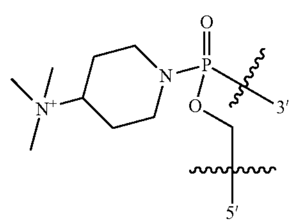 |
| B52 | PMO$^{ca}$ | 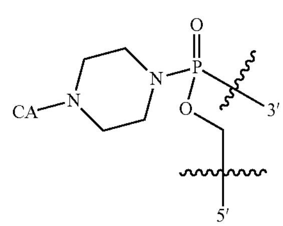 |

CA = Cholate

| | | |
|---|---|---|
| B53 | PMO$^{dca}$ | | dCA = Cholate

| | | |
|---|---|---|
| B54 | PMO$^{guan}$ (g) | |

TABLE 3-continued

Representative Intersubunit Linkages

| No. | Name | Structure |
|---|---|---|
| B55 | PMO$^{+phos}$ | 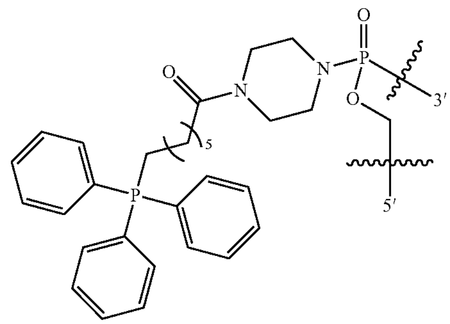 |
| B56 | PMO$^{apnphos}$ | 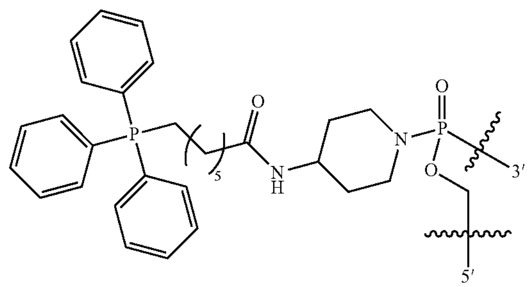 |

In the sequences and discussion that follows, the above names for the linkages are often used. For example, a base comprising a PMO$^{apn}$ linkage is illustrated as $^{apn}$B, where B is a base. Other linkages are designated similarly. In addition, abbreviated designations may be used, for example, the abbreviated designations in parentheses above may be used (e.g., $^a$B, refers to $^{apn}$B). Other readily identifiable abbreviations may also be used.

As noted above, the present disclosure also provides an oligomer comprising modified terminal groups. Applicants have found that modification of the 3' and/or 5' end of the oligomer with various chemical moieties provides beneficial therapeutic properties (e.g., enhanced cell delivery, potency, and/or tissue distribution, etc.) to the oligomers. In various embodiments, the modified terminal groups comprise a hydrophobic moiety, while in other embodiments the modified terminal groups comprise a hydrophilic moiety. The modified terminal groups may be present with or without the linkages described above. For example, in some embodiments, the oligomers comprise one or more modified terminal group and linkages of type (A), for example linkages wherein X is —N(CH$_3$)$_2$. In other embodiments, the oligomers comprise one or more modified terminal group and linkages of type (B), for example linkages wherein X is 4-aminopiperidin-1-yl (i.e., APN). In yet other embodiments, the oligomers comprise one or more modified terminal group and a mixture of linkages (A) and (B). For example, the oligomers may comprise one or more modified terminal group (e.g., trityl or triphenyl acetyl) and linkages wherein X is —N(CH$_3$)$_2$ and linkages wherein X is 4-aminopiperidin-1-yl. Other combinations of modified terminal groups and modified linkages also provide favorable therapeutic properties to the oligomers.

In one embodiment, the oligomers comprising terminal modifications have the following structure (XVII):

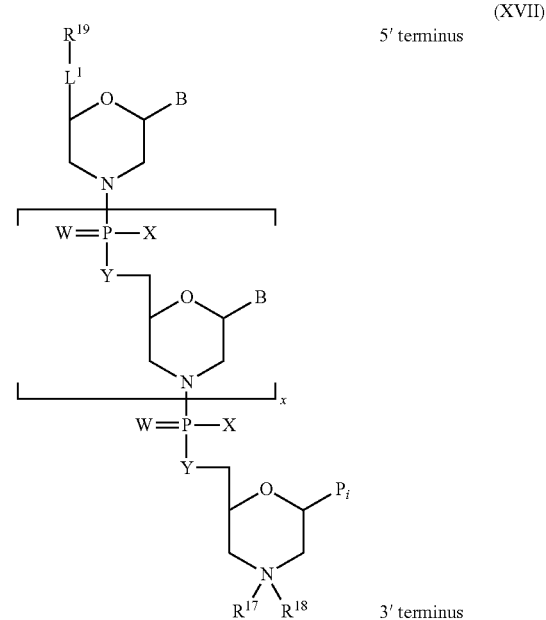

or a salt or isomer thereof, wherein X, W and Y are as defined above for any of linkages (A) and (B) and:

R$^{17}$ is, at each occurrence, independently absent, hydrogen or C$_1$-C$_6$ alkyl;

R$^{18}$ and R$^{19}$ are, at each occurrence, independently absent, hydrogen, a cell-penetrating peptide, a natural or non-natural amino acid, C$_2$-C$_{30}$ alkylcarbonyl, —C(═O)OR$^{21}$ or R$^{20}$;

R$^{20}$ is, at each occurrence, independently guanidinyl, heterocyclyl, C$_1$-C$_{30}$ alkyl, C$_3$-C$_8$ cycloalkyl; C$_6$-C$_{30}$ aryl, C$_7$-C$_{30}$ aralkyl, C$_3$-C$_{30}$ alkylcarbonyl, C$_3$-C$_8$ cycloalkylcarbonyl, $C_3$-$C_8$ cycloalkylalkylcarbonyl, $C_7$-$C_{30}$ arylcarbonyl, $C_7$-$C_{30}$ aralkylcarbonyl, $C_2$-$C_{30}$ alkyloxycarbonyl, $C_3$-$C_8$ cycloalkyloxycarbonyl, $C_7$-$C_{30}$ aryloxycarbonyl, $C_8$-$C_{30}$ aralkyloxycarbonyl, or —P(=O)($R^{22}$)$_2$;

B is a base-pairing moiety;

$L^1$ is an optional linker up to 18 atoms in length comprising bonds selected from alkyl, hydroxyl, alkoxy, alkylamino, amide, ester, carbonyl, carbamate, phosphorodiamidate, phosphoroamidate, phosphorothioate, piperazine and phosphodiester; and x is an integer of 0 or greater; and wherein at least one of $R^{18}$ or $R^{19}$ is $R^{20}$; and wherein at least one of $R^{18}$ or $R^{19}$ is $R^{20}$ and provided that both of $R^{17}$ and $R^{18}$ are not absent.

The oligomers with modified terminal groups may comprise any number of linkages of types (A) and (B). For example, the oligomers may comprise only linkage type (A). For example, X in each linkage may be —N(CH$_3$)$_2$. Alternatively, the oligomers may only comprise linkage (B). In certain embodiments, the oligomers comprise a mixture of linkages (A) and (B), for example from 1 to 4 linkages of type (B) and the remainder of the linkages being of type (A). Linkages in this regard include, but are not limited to, linkages wherein X is aminopiperidinyl for type (B) and dimethyl amino for type (A).

In some embodiments, $R^{17}$ is absent. In some embodiments, $R^{17}$ is hydrogen. In some embodiments, $R^{17}$ is $C_1$-$C_6$ alkyl. In some embodiments, $R^{17}$ is methyl. In yet other embodiments, $R^{17}$ is ethyl. In some embodiments, $R^{17}$ is $C_3$ alkyl. In some other embodiments, $R^{17}$ is isopropyl. In other embodiments, $R^{17}$ is $C_4$ alkyl. In yet other embodiments, $R^{17}$ is $C_5$ alkyl. In some other embodiments, $R^{17}$ is $C_6$ alkyl.

In other embodiments, $R^{18}$ is absent. In some embodiments, $R^8$ is hydrogen. In some embodiments, $R^{18}$ is a cell-penetrating peptide as described in more detail below. In some embodiments, $R^{18}$ is a natural or non-natural amino acid, for example trimethylglycine. In some embodiments, $R^{18}$ is $R^{20}$.

In other embodiments, $R^{19}$ is absent. In some embodiments, $R^{19}$ is hydrogen. In some embodiments, $R^{19}$ is a cell-penetrating peptide as described in more detail below. In some embodiments, $R^{19}$ is a natural or non-natural amino acid, for example trimethylglycine. In some embodiments, $R^{19}$ is-C(=O)O$R^{17}$, for example $R^{19}$ may have the following structure:

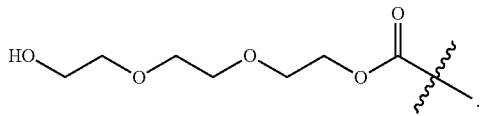 [SMILES: *C(=O)OCCOCCOCCO]

In other embodiments $R^{18}$ or $R^{19}$ is $C_2$-$C_{30}$ alkylcarbonyl, for example —C(=O)(CH$_2$)$_n$CO$_2$H, where n is 1 to 6, for example 2. In other examples, $R^{18}$ or $R^{19}$ is acetyl.

In some embodiments, $R^{20}$ is, at each occurrence, independently guanidinyl, heterocyclyl, $C_1$-$C_{30}$ alkyl, $C_3$-$C_8$ cycloalkyl; $C_6$-$C_{30}$ aryl, $C_7$-$C_{30}$ aralkyl, $C_3$-$C_{30}$ alkylcarbonyl, $C_3$-$C_8$ cycloalkylcarbonyl, $C_3$-$C_8$ cycloalkylalkylcarbonyl, $C_6$-$C_{30}$ arylcarbonyl, $C_7$-$C_{30}$ aralkylcarbonyl, $C_2$-$C_{30}$ alkyloxycarbonyl, $C_3$-$C_8$ cycloalkyloxycarbonyl, $C_7$-$C_{30}$ aryloxycarbonyl, $C_8$-$C_{30}$ aralkyloxycarbonyl, —C(=O)O$R^{21}$, or —P(=O)($R^{22}$)$_2$, wherein $R^{21}$ is $C_1$-$C_{30}$ alkyl comprising one or more oxygen or hydroxyl moieties or combinations thereof and each $R^{22}$ is $C^6$-$C^{12}$ aryloxy.

In certain other embodiments, $R^{19}$ is —C(=O)O$R^{21}$ and $R^{18}$ is hydrogen, guanidinyl, heterocyclyl, $C_1$-$C_{30}$ alkyl, $C_3$-$C_8$ cycloalkyl; $C_6$-$C_{30}$ aryl, $C_3$-$C_{30}$ alkylcarbonyl, $C_3$-$C_8$ cycloalkylcarbonyl, $C_3$-$C_8$ cycloalkylalkylcarbonyl, $C_7$-$C_{30}$ arylcarbonyl, $C_7$-$C_{30}$ aralkylcarbonyl, $C_2$-$C_{30}$ alkyloxycarbonyl, $C_3$-$C_8$ cycloalkyloxycarbonyl, $C_7$-$C_{30}$ aryloxycarbonyl, $C_8$-$C_{30}$ aralkyloxycarbonyl, or —P(=O)($R^{22}$)$_2$, wherein each $R^{22}$ is $C^6$-$C^{12}$ aryloxy.

In other embodiments, $R^{20}$ is, at each occurrence, independently guanidinyl, heterocyclyl, $C_1$-$C_{30}$ alkyl, $C_3$-$C_8$ cycloalkyl; $C_6$-$C_{30}$ aryl, $C_3$-$C_{30}$ alkylcarbonyl, $C_3$-$C_8$ cycloalkylcarbonyl, $C_3$-$C_8$ cycloalkylalkylcarbonyl, $C_7$-$C_{30}$ arylcarbonyl, $C_7$-$C_{30}$ aralkylcarbonyl, $C_2$-$C_{30}$ alkyloxycarbonyl, $C_3$-$C_8$ cycloalkyloxycarbonyl, $C_7$-$C_{30}$ aryloxycarbonyl, $C_8$-$C_{30}$ aralkyloxycarbonyl, or —P(=O)($R^{22}$)$_2$. While in other examples, $R^{20}$ is, at each occurrence, independently guanidinyl, heterocyclyl, $C_1$-$C_{30}$ alkyl, $C_3$-$C_8$ cycloalkyl; $C_6$-$C_{30}$ aryl, $C_7$-$C_{30}$ aralkyl, $C_3$-$C_8$ cycloalkylcarbonyl, $C_3$-$C_8$ cycloalkylalkylcarbonyl, $C_7$-$C_{30}$ arylcarbonyl, $C_7$-$C_{30}$ aralkylcarbonyl, $C_2$-$C_{30}$ alkyloxycarbonyl, $C_3$-$C_8$ cycloalkyloxycarbonyl, $C_7$-$C_{30}$ aryloxycarbonyl, $C_8$-$C_{30}$ aralkyloxycarbonyl, or —P(=O)($R^{22}$)$_2$.

In some embodiments $R^{20}$ is guanidinyl, for example mono methylguanidynyl or dimethylguanidinyl. In other embodiments, $R^{20}$ is heterocyclyl. For example, in some embodiments, $R^{20}$ is piperidin-4-yl. In some embodiments, the piperidin-4-yl is substituted with trityl or Boc groups. In other embodiments, $R^{20}$ is $C_3$-$C_8$ cycloalkyl. In other embodiments, $R^{20}$ is $C_6$-$C_{30}$ aryl.

In some embodiments, $R^{20}$ is $C_7$-$C_{30}$ arylcarbonyl. For example, In some embodiments, $R^{20}$ has the following structure (XVIII):

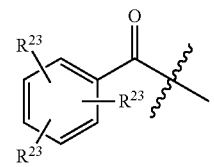

(XVIII)

wherein $R^{23}$ is, at each occurrence, independently hydrogen, halo, $C_1$-$C_{30}$ alkyl, $C_1$-$C_{30}$ alkoxy, $C_1$-$C_{30}$ alkyloxycarbonyl, $C_7$-$C_{30}$ aralkyl, aryl, heteroaryl, heterocyclyl or heterocyclalkyl, and wherein one $R^{23}$ may join with another $R^{23}$ to form a heterocyclyl ring. In some embodiments, at least one $R^{23}$ is hydrogen, for example, in some embodiments, each $R^{23}$ is hydrogen. In other embodiments, at least one $R^{23}$ is $C_1$-$C_{30}$ alkoxy, for example in some embodiments, each $R^{23}$ is methoxy. In other embodiments, at least one $R^{23}$ is heteroaryl, for example in some embodiments, at least one $R^{23}$ has one of the following structures (XVIIIa) of (XVIIIb):

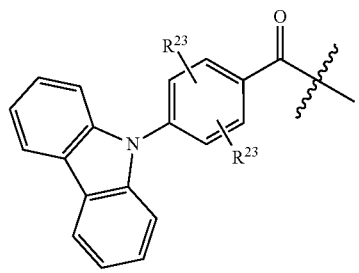

(XVIIIa)

or

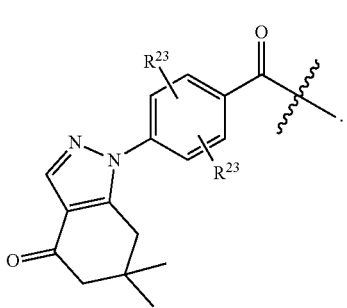

(XVIIIb)

In still other embodiments, one $R^{23}$ joins with another $R^{23}$ to form a heterocyclyl ring. For example, in one embodiment, $R^{20}$ is 5-carboxyfluorescein.

In other embodiments, $R^{20}$ is $C_7$-$C_{30}$ aralkylcarbonyl. For example, in various embodiments, $R^{20}$ has one of the following structures (XIX), (XX) or (XXI):

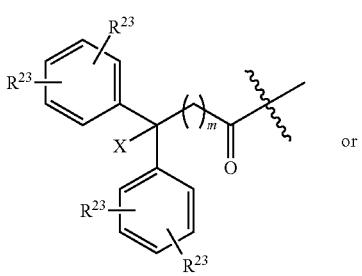

(XIX)

(XX)

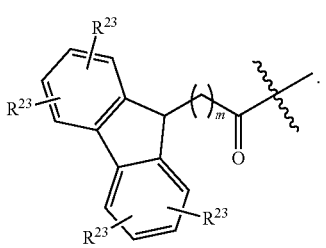

(XXI)

wherein $R^{23}$ is, at each occurrence, independently hydrogen, halo, $C_1$-$C_{30}$ alkyl, $C_1$-$C_{30}$ alkoxy, $C_1$-$C_{30}$ alkyloxycarbonyl, $C_7$-$C_{30}$ aralkyl, aryl, heteroaryl, heterocyclyl or heterocyclalkyl, wherein one $R^{23}$ may join with another $R^{23}$ to form a heterocyclyl ring, X is —OH or halo and m is an integer from 0 to 6. In some specific embodiments, m is 0. In other embodiments, m is 1, while in other embodiments, m is 2. In other embodiments, at least one $R^{23}$ is hydrogen, for example in some embodiments each $R^{23}$ is hydrogen. In some embodiments, X is hydrogen. In other embodiments, X is —OH. In other embodiments, X is $C_1$. In other embodiments, at least one $R^{23}$ is $C_1$-$C_{30}$ alkoxy, for example methoxy.

In still other embodiments, $R^{20}$ is $C_7$-$C_{30}$ aralkyl, for example trityl. In other embodiments, $R^{20}$ is methoxy trityl. In some embodiments, $R^{20}$ has the following structure (XXII):

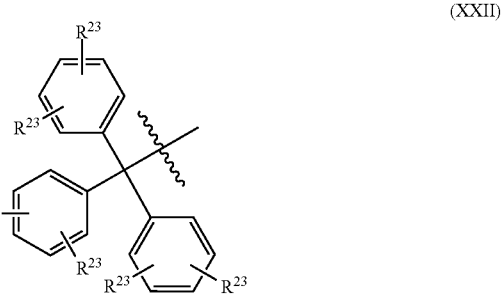

(XXII)

wherein $R^{23}$ is, at each occurrence, independently hydrogen, halo, $C_1$-$C_{30}$ alkyl, $C_1$-$C_{30}$ alkoxy, $C_1$-$C_{30}$ alkyloxycarbonyl, $C_7$-$C_{30}$ aralkyl, aryl, heteroaryl, heterocyclyl or heterocyclalkyl, and wherein one $R^{23}$ may join with another $R^{23}$ to form a heterocyclyl ring. For example, in some embodiments each $R^{23}$ is hydrogen. In other embodiments, at least one $R^{23}$ is $C_1$-$C_{30}$ alkoxy, for example methoxy.

In yet other embodiments, $R^{20}$ is $C_7$-$C_{30}$ aralkyl and $R^{20}$ has the following structure (XXIII):

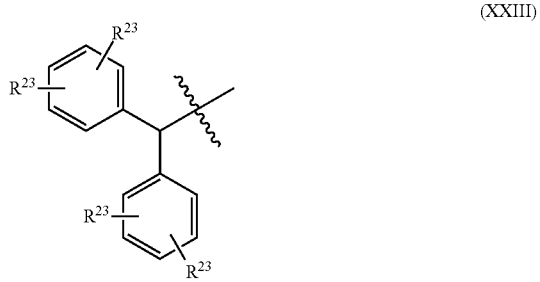

(XXIII)

In some embodiments, at least one $R^{23}$ is halo, for example chloro. In some other embodiments, one $R^{23}$ is chloro in the para position.

In other embodiments, $R^{20}$ is $C_1$-$C_{30}$ alkyl. For example, In some embodiments, $R^{20}$ is a $C_4$-$C_{20}$ alkyl and optionally comprises one or more double bonds. For example, In some embodiments, $R^{20}$ is a $C_{4-10}$ alkyl comprising a triple bond, for example a terminal triple bond. In some embodiments, $R^{20}$ is hexyn-6-yl. In some embodiments, $R^{20}$ has one of the following structures (XXIV), (XXV), (XXVI) or (XXVII):

(XXIV)

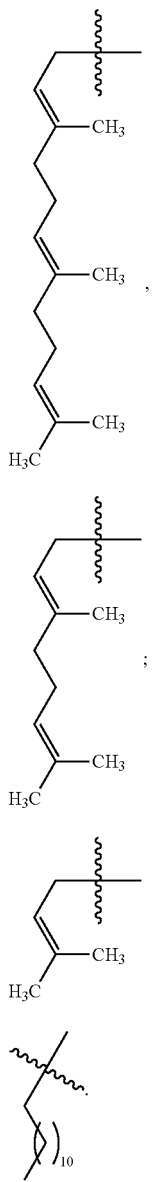

(XXV)

(XXVI)

(XXVII)

In still other embodiments, $R^{20}$ is a $C_3$-$C_{30}$ alkylcarbonyl, for example a $C_3$-$C_{10}$ alkyl carbonyl. In some embodiments, $R^{20}$ is —C(=O)(CH$_2$)$_p$SH or —C(=O)(CH$_2$)$_p$SSHet, wherein p is an integer from 1 to 6 and Het is a heteroaryl. For example, p may be 1 or p may be 2. In other example Het is pyridinyl, for example pyridin-2-yl. In other embodiments, the $C_3$-$C_{30}$ alkylcarbonyl is substituted with a further oligomer, for example in some embodiments the oligomer comprises a $C_3$-$C_{30}$ alkyl carbonyl at the 3' position which links the oligomer to the 3' position of another oligomer. Such terminal modifications are included within the scope of the present disclosure.

In other embodiments, $R^{20}$ is a $C_3$-$C_{30}$ alkyl carbonyl which is further substituted with an arylphosphoryl moiety, for example triphenyl phosphoryl. Examples of such $R^{20}$ groups include structure 33 in Table 2.

In other examples, $R_{20}$ is $C_3$-$C_8$ cycloalkylcarbonyl, for example $C_5$-$C_7$ alkyl carbonyl. In these embodiments, $R_{20}$ has the following structure (XXVIII):

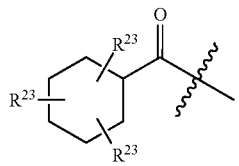

(XXVIII)

wherein $R^{23}$ is, at each occurrence, independently hydrogen, halo, $C_1$-$C_{30}$ alkyl, $C_1$-$C_{30}$ alkoxy, $C_1$-$C_{30}$ alkyloxycarbonyl, $C_7$-$C_{30}$ aralkyl, aryl, heteroaryl, heterocyclyl or heterocyclalkyl, and wherein one $R^{23}$ may join with another $R^{23}$ to form a heterocyclyl ring. In some embodiments, $R^{23}$ is heterocyclylalkyl, for example in some embodiments $R^{23}$ has the following structure:

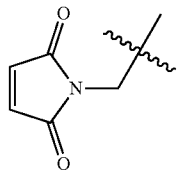 [SMILES: *CN1C(=O)C=CC1=O]

In some other embodiments, $R^{20}$ is $C_3$-$C_8$ cycloalkylalkylcarbonyl. In other embodiments, $R^{20}$ is $C_2$-$C_{30}$ alkyloxycarbonyl. In other embodiments, $R^{20}$ is $C_3$-$C_8$ cycloalkyloxycarbonyl. In other embodiments, $R^{20}$ is $C_7$-$C_{30}$ aryloxycarbonyl. In other embodiments, $R^{20}$ is $C_8$-$C_{30}$ aralkyloxycarbonyl. In other embodiments, $R^{20}$ is —P(=O)($R^{22}$)$_2$, wherein each $R^{22}$ is $C^6$-$C^{12}$ aryloxy, for example in some embodiments $R^{20}$ has the following structure (C24):

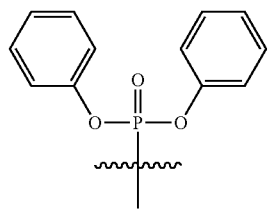

(C24)

In other embodiments, $R^{20}$ comprises one or more halo atoms. For example, in some embodiments $R^{20}$ comprises a perfluoro analogue of any of the above $R^{20}$ moieties. In other embodiments, $R^{20}$ is p-trifluoromethylphenyl, trifluoromethyltrityl, perfluoropentyl or pentafluorophenyl.

In some embodiments the 3' terminus comprises a modification and in other embodiments the 5' terminus comprises a modification. In other embodiments both the 3' and 5' termini comprise modifications. Accordingly, in some embodiments, $R^{18}$ is absent and $R^{19}$ is $R^{20}$. In other embodiments, $R^{19}$ is absent and $R^{18}$ is $R^{20}$. In yet other embodiments, $R^{18}$ and $R^{19}$ are each $R^{20}$.

In some embodiments, the oligomer comprises a cell-penetrating peptide in addition to a 3' or 5' modification. Accordingly, in some embodiments $R^{19}$ is a cell-penetrating peptide and $R^{18}$ is $R^{20}$. In other embodiments, $R^8$ is a cell-penetrating peptide and $R^{19}$ is $R^{20}$. In further embodiments of the foregoing, the cell-penetrating peptide is an arginine-rich peptide.

In some embodiments, the linker $L^1$ that links the 5' terminal group (i.e., $R^{19}$) to the oligomer may be present or absent. The linker comprises any number of functional groups and lengths provided the linker retains its ability to link the 5' terminal group to the oligomer and provided that the linker does not interfere with the oligomer's ability to bind to a target sequence in a sequence specific manner. In one embodiment, L comprises phosphorodiamidate and piperazine bonds. For example, in some embodiments L has the following structure (XXIX):

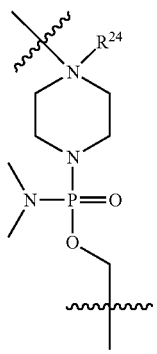

(XXIX)

wherein $R^{24}$ is absent, hydrogen or $C_1$-$C_6$ alkyl. In some embodiments, $R^{24}$ is absent. In some embodiments, $R^{24}$ is hydrogen. In some embodiments, $R^{24}$ is $C_1$-$C_6$ alkyl. In some embodiments, $R^{24}$ is methyl. In other embodiments, $R^{24}$ is ethyl. In yet other embodiments, $R^{24}$ is $C_3$ alkyl. In some other embodiments, $R^{24}$ is isopropyl. In yet other embodiments, $R^{24}$ is $C_4$ alkyl. In some embodiments, $R^{24}$ is $C_5$ alkyl. In yet other embodiments, $R^{24}$ is $C_6$ alkyl.

In yet other embodiments, $R^{20}$ is $C_3$-$C_{30}$ alkylcarbonyl, and $R^{20}$ has the following structure (XXX):

(XXX)

wherein $R^{25}$ is hydrogen or —$SR^{26}$, wherein $R^{26}$ is hydrogen, $C_1$-$C_{30}$ alkyl, heterocyclyl, aryl or heteroaryl, and q is an integer from 0 to 6.

In further embodiments of any of the above, $R^{23}$ is, at each occurrence, independently hydrogen, halo, $C_1$-$C_{30}$ alkyl, $C_1$-$C_{30}$ alkoxy, aryl, heteroaryl, heterocyclyl or heterocyclalkyl.

In some other embodiments, only the 3' terminus of the oligomer is conjugated to one of the groups noted above. In some other embodiments, only the 5' terminus of the oligomer is conjugated to one of the groups noted above. In other embodiments, both the 3' and 5' termini comprise one of the groups noted above. The terminal group may be selected from any one of the groups noted above or any of the specific groups illustrated in Table 4.

TABLE 4

Representative Terminal Groups

| No. | Name | Structure |
|---|---|---|
| C1 | Trimethoxybenzoyl | 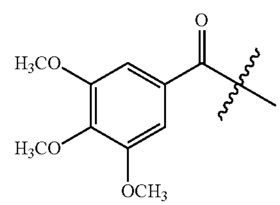 [SMILES: *C(=O)c1cc(OC)c(OC)c(OC)c1] |
| C2 | 9-fluorene-carboxyl | 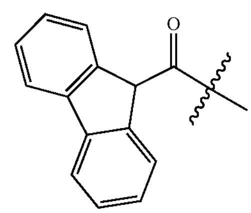 [SMILES: *C(=O)C1c2ccccc2-c2ccccc21] |
| C3 | 4-carbazolylbenzoyl | 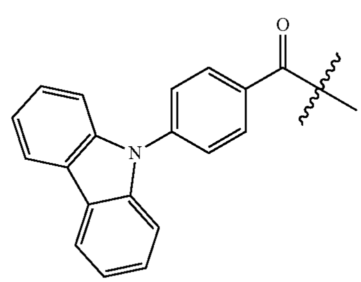 [SMILES: *C(=O)c1ccc(-n2c3ccccc3c3ccccc32)cc1] |

TABLE 4-continued
| | Representative Terminal Groups | |
|---|---|---|
| No. | Name | Structure |
| C4 | 4-indazolylonebenzoyl | 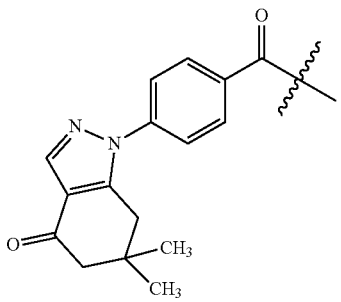 [SMILES: *C(=O)c1ccc(-n2ncc3c2CC(C)(C)CC3=O)cc1] |
| C5 | Farnesyl | 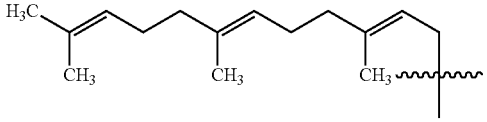 [SMILES: *C/C=C(\C)CC/C=C(\C)CCC=C(C)C] |
| C6 | Geranyl | 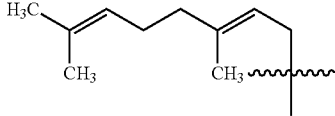 [SMILES: *C/C=C(\C)CCC=C(C)C] |
| C7 | Prenyl | 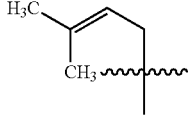 |
| C8 | Diphenylacetyl | 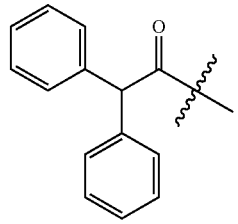 [SMILES: *C(=O)C(c1ccccc1)c1ccccc1] |
| C9 | Chlorodiphenylacetyl | 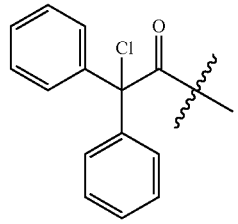 [SMILES: *C(=O)C(Cl)(c1ccccc1)c1ccccc1] |
| C10 | Hydroxydiphenylacetyl | 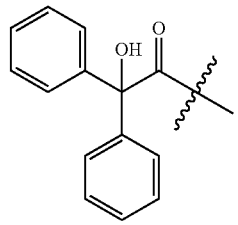 [SMILES: *C(=O)C(O)(c1ccccc1)c1ccccc1] |

TABLE 4-continued
Representative Terminal Groups
| No. | Name | Structure |
|---|---|---|
| C11 | Triphenylpropionyl | 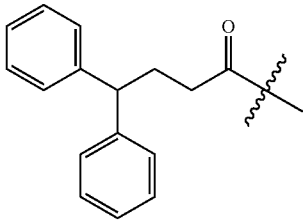 [SMILES: *C(=O)CCC(c1ccccc1)c1ccccc1] |
| C12 | Triphenylpropyl | 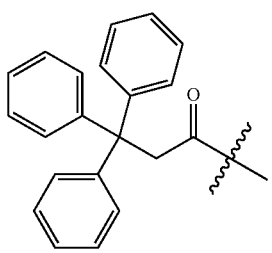 [SMILES: *C(=O)CC(c1ccccc1)(c1ccccc1)c1ccccc1] |
| C13 | Triphenylacetyl | 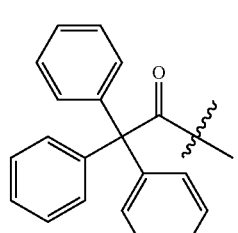 |
| C14 | Trityl (Tr) | 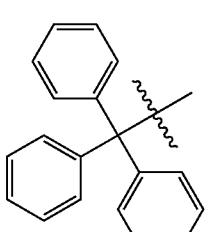 |
| C15 | Methoxytrityl (MeOTr) | 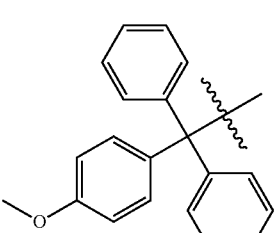 |
| C16 | Methylsuccinimidyl-cyclohexoyl | 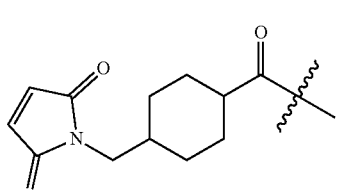 |
| C17 | Thioacetyl | 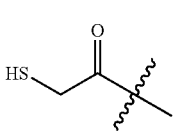 [SMILES: *C(=O)CS] |

TABLE 4-continued

| | Representative Terminal Groups | |
|---|---|---|
| No. | Name | Structure |
| C18 | COCH$_2$CH$_2$SSPy | |
| C19 | Guanidinyl | |
| C20 | Trimethylglycine | |
| C21 | Lauroyl | |
| C22 | Triethyleneglycoloyl (EG3) | |
| C23 | Succinicacetyl | |
| C24 | Diphenylphosphoryl | |
| C25 | Piperidin-4-yl | |
| C26 | Tritylpiperidin-4-yl | |

TABLE 4-continued
Representative Terminal Groups
| No. | Name | Structure |
|---|---|---|
| C27 | Boc-Piperidin-4-yl | 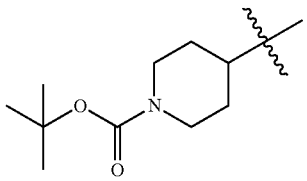 [SMILES: *C1CCN(C(=O)OC(C)(C)C)CC1] |
| C28 | Hexyn-6-yl | 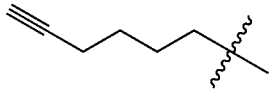 [SMILES: *CCCCC#C] |
| C29 | 5-carboxyfluorescein | 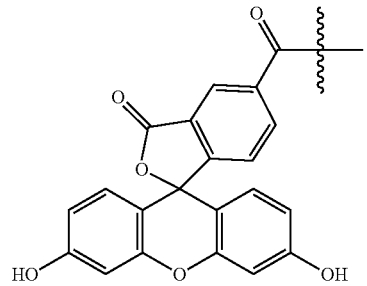 [SMILES: *C(=O)c1ccc2c(c1)C(=O)OC21c2ccc(O)cc2Oc2cc(O)ccc21] |
| C30 | Benzhydryl | 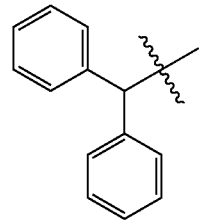 [SMILES: *C(c1ccccc1)c1ccccc1] |
| C31 | p-Chlorobenzhydryl | 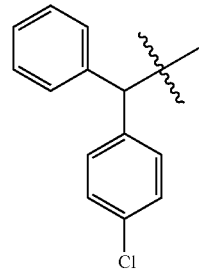 [SMILES: *C(c1ccccc1)c1ccc(Cl)cc1] |
| C32 | Piperazinyl (pip) | 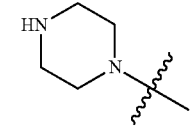 [SMILES: *N1CCNCC1] |
| C33 | Triphenylphos | 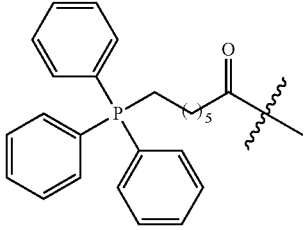 |

TABLE 4-continued

Representative Terminal Groups

| No. | Name | Structure |
|-----|------|-----------|
| C34 | Dimerized | 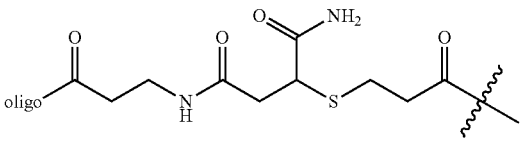 |

Oligo = a further oligomer

Peptide Transporters

In some embodiments, the subject oligomer is conjugated to a peptide transporter moiety, for example a cell-penetrating peptide transport moiety, which is effective to enhance transport of the oligomer into cells. For example, in some embodiments the peptide transporter moiety is an arginine-rich peptide. In further embodiments, the transport moiety is attached to either the 5' or 3' terminus of the oligomer. When such peptide is conjugated to either termini, the opposite termini is then available for further conjugation to a modified terminal group as described herein.

In some embodiments of the foregoing, the peptide transport moiety comprises 6 to 16 subunits selected from X' subunits, Y' subunits, and Z' subunits, where (a) each X' subunit independently represents lysine, arginine or an arginine analog, said analog being a cationic α-amino acid comprising a side chain of the structure $R^{33}N{=}C(NH_2)R^{34}$, where $R^{33}$ is H or R; $R^{34}$ is $R^{35}$, $NH_2$, NHR, or $NR_{34}$, where $R^{35}$ is lower alkyl or lower alkenyl and may further include oxygen or nitrogen; $R^{33}$ and $R^{34}$ may together form a ring; and the side chain is linked to said amino acid via $R^{33}$ or $R^{34}$;

(b) each Y' subunit independently represents a neutral amino acid —C(O)—(CHR)$_n$—NH—, where n is 2 to 7 and each R is independently H or methyl; and (c) each Z' subunit independently represents an α-amino acid having a neutral aralkyl side chain;

wherein the peptide comprises a sequence represented by one of $(X'Y'X')_p$, $(X'Y')_m$, and $(X'Z'Z')_p$, where p is 2 to 5 and m is 2 to 8.

In selected embodiments, for each X', the side chain moiety is guanidyl, as in the amino acid subunit arginine (Arg). In further embodiments, each Y' is —CO—(CH$_2$)$_n$—CHR—NH—, where n is 2 to 7 and R is H. For example, when n is 5 and R is H, Y' is a 6-aminohexanoic acid subunit, abbreviated herein as Ahx; when n is 2 and R is H, Y' is a 3-alanine subunit.

In certain embodiments, peptides of this type include those comprising arginine dimers alternating with single Y' subunits, where Y' is Ahx. Examples include peptides having the formula (RY'R)$_p$ or the formula (RRY')$_p$, where Y' is Ahx. In one embodiment, Y' is a 6-aminohexanoic acid subunit, R is arginine and p is 4.

In a further embodiment, each Z' is phenylalanine, and m is 3 or 4.

In some embodiments, the conjugated peptide is linked to a terminus of the oligomer via a linker Ahx-B, where Ahx is a 6-aminohexanoic acid subunit and B is a 3-alanine subunit.

In selected embodiments, for each X', the side chain moiety is independently selected from the group consisting of guanidyl (HN=C(NH$_2$)NH—), amidinyl (HN=C(NH$_2$)C—), 2-aminodihydropyrimidyl, 2-aminotetrahydropyrimidyl, 2-aminopyridinyl, and 2-aminopyrimidonyl, and it is preferably selected from guanidyl and amidinyl. In one embodiment, the side chain moiety is guanidyl, as in the amino acid subunit arginine (Arg).

In some embodiments, the Y' subunits are either contiguous, in that no X' subunits intervene between Y' subunits, or interspersed singly between X' subunits. However, in some embodiments the linking subunit may be between Y' subunits. In one embodiment, the Y' subunits are at a terminus of the peptide transporter; in other embodiments, they are flanked by X' subunits. In further embodiments, each Y' is —CO—(CH$_2$)$_n$—CHR—NH—, where n is 2 to 7 and R is H. For example, when n is 5 and R is H, Y' is a 6-aminohexanoic acid subunit, abbreviated herein as Ahx. In selected embodiments of this group, each X' comprises a guanidyl side chain moiety, as in an arginine subunit. Exemplary peptides of this type include those comprising arginine dimers alternating with single Y' subunits, where Y' is preferably Ahx. Examples include peptides having the formula (RY'R)$_4$ or the formula (RRY')$_4$, where Y' is preferably Ahx. In some embodiments, the nucleic acid analog is linked to a terminal Y' subunit, preferably at the C-terminus. In other embodiments, the linker is of the structure AhxB, where Ahx is a 6-aminohexanoic acid subunit and B is a β-alanine subunit.

The peptide transport moieties as described above have been shown to greatly enhance cell entry of attached oligomers, relative to uptake of the oligomer in the absence of the attached transport moiety, and relative to uptake by an attached transport moiety lacking the hydrophobic subunits Y'. Such enhanced uptake may be evidenced by at least a two-fold increase, or in other embodiments a four-fold increase, in the uptake of the compound into mammalian cells relative to uptake of the agent by an attached transport moiety lacking the hydrophobic subunits Y'. In some embodiments, uptake is enhanced at least twenty fold or at least forty fold, relative to the unconjugated compound.

A further benefit of the peptide transport moiety is its expected ability to stabilize a duplex between an antisense oligomer and its target nucleic acid sequence. While not wishing to be bound by theory, this ability to stabilize a duplex may result from the electrostatic interaction between the positively charged transport moiety and the negatively charged nucleic acid. In some embodiments, the number of charged subunits in the transporter is less than 14, as noted above, or in other embodiments between 8 and 11, since too high a number of charged subunits may lead to a reduction in sequence specificity.

The present disclosure also incorporates conjugates of peptide transport moieties and nucleic acid analogues. As noted above, the peptide transport moieties are generally effective to enhance cell penetration of the nucleic acid analogues. The applicants have also discovered that including a glycine (G) or proline (P) amino acid subunit between the nucleic acid analogue and the remainder of the peptide transport moiety (e.g., at the carboxy or amino terminus of the carrier peptide) reduces the toxicity of the conjugate, while the efficacy remains the same or is improved relative to conjugates with different linkages between the peptide transport moiety and nucleic acid analogue. Thus the presently disclosed conjugates have a better therapeutic window and are more promising drug candidates than other peptide-oligomer conjugates.

In addition to reduced toxicity, the presence of a glycine or proline amino acid subunit between the nucleic acid analogue and the carrier peptide is believed to provide additional advantages. For example, glycine is inexpensive and is easily coupled to the nucleic acid analogue (or optional linker) without any possibility of racemization. Similarly, proline is easily coupled without racemization and also provides carrier peptides which are not helix formers. The hydrophobicity of proline may also confer certain advantages with respect to interaction of the carrier peptide with the lipid bilayer of cells, and carrier peptides comprising multiple prolines (for example in certain embodiments) may resist G-tetraplex formation. Finally, in certain embodiments, when the proline moiety is adjacent to an arginine amino acid subunit, the proline moiety confers metabolic stability to the conjugates since the argine-proline amide bond is not cleavable by common endopeptidases.

In some embodiments, conjugation of peptides to antisense oligonucleotides is as described in PCT publication WO2012/1150960 which is incorporated by reference in its entirety. In a particular embodiment, for example, a peptide conjugated oligonucleotide utilizes glycine as the linker between the CPP and the antisense oligonucleotide. For example, antisense oligonucleotides of the invention can be coupled to an arginine-rich peptide, such as (Arg)6Gly (6 arginine and 1 glycine linked to an oligonucleotide). As an example, this peptide can be conjugated to a PMO and is known as "R6-G-PMO".

Further exemplary arginine-rich cell-penetrating peptide transporters comprising various linkers (C, G, P, Ahx, B) are given below in Table 5. As disclosed in Table 2 above, a preferred cell-penetrating peptide transporter is SEQ ID NO: 45 conjugated to a PMO at the 3' terminus through a glycine linker ($R_6G$). Linkage of $R_6G$ to the 5' terminus is also a preferred embodiment.

TABLE 5

Arginine-Rich Cell-Penetrating Peptide Transporters

| NAME (DESIGNATION) | SEQUENCE | SEQ ID NO.[A] |
|---|---|---|
| rTAT | RRRQRRKKR | 39 |
| Tat | RKKRRQRRR | 40 |
| $R_9F_2$ | RRRRRRRRRFF | 41 |
| $R_5F_2R_4$ | RRRRRFFRRRR | 42 |
| $R_4$ | RRRR | 43 |
| $R_5$ | RRRRR | 44 |
| $R_6$ | RRRRRR | 45 |
| $R_7$ | RRRRRRR | 46 |
| $R_8$ | RRRRRRRR | 47 |
| $R_9$ | RRRRRRRRR | 48 |
| $(RX)_8$ | RXRXRXRXRXRXRXRX | 49 |
| $(RAhxR)_4$; (P007) | RAhxRRAhxRRAhxRRAhxR | 50 |

TABLE 5-continued

Arginine-Rich Cell-Penetrating Peptide Transporters

| NAME (DESIGNATION) | SEQUENCE | SEQ ID NO.[A] |
|---|---|---|
| $(RAhxR)_5$; (CP04057) | RAhxRRAhxRRAhxRRAhxRRAhxR | 51 |
| $(RAhxRRBR)_2$; (CP06062) | RAhxRRBRRAhxRRBR | 52 |
| $(RAR)_4F_2$ | RARRARRARRARFFC | 53 |
| $(RGR)_4F_2$ | RGRRGRRGRRGRFFC | 54 |

[A]Sequences assigned to SEQ ID NOs do not include the linkage portion (e.g., C, G, P, Ahx, B, AhxB where Ahx and B refer to 6-aminohexanoic acid and beta-alanine, respectively).

Methods of In Vitro Use

In another aspect, the present invention relates to methods of using the LMNA and/or HGPS-targeted antisense oligonucleotides described herein for treating a cell or tissue in vitro to reduce expression of one or more mRNA isoforms and/or mutant proteins in a beneficial manner. The cells or tissue that may be modulated by the present invention are preferably mammalian cells, or more preferably human cells. Such cells can be of a healthy state or of a diseased state, such as cells expressing progerin. In certain aspects, the cell is a cell expressing progerin resulting in a progeroid laminopathy.

Certain embodiments therefore relate generally to methods for reducing expression of abnormally spliced LMNA mRNA in vitro comprising contacting a cell with one or more antisense oligonucleotides described herein, or a composition containing the same, thereby reducing expression of progerin. These and related methods can be used to reduce expression of any one or more of the mutant LMNA mRNA isoforms described herein and known in the art.

The in vitro methods may employ compositions comprising oligonucleotides in combination with pharmaceutically acceptable carriers. The phrase "pharmaceutically acceptable" is employed herein to refer to those compounds, materials, compositions, and/or dosage forms which are, within the scope of sound medical judgment, suitable for use in contact with cells and/or tissues without excessive toxicity, irritation, allergic response, or other problem or complication, commensurate with a reasonable benefit/risk ratio.

The phrase "pharmaceutically acceptable carrier" as used herein means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material. Each carrier must be "acceptable" in the sense of being compatible with the other ingredients of the formulation and not injurious to the cell or tissue being contacted.

Some examples of materials that can serve as pharmaceutically-acceptable carriers include, without limitation: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims. The following examples are provided by way of illustration only and not by way of limitation. Those of skill in the art will readily recognize a variety of noncritical parameters that could be changed or modified to yield essentially similar results.

SEQUENCE LISTING TABLE

| NAME | SEQUENCE | SEQ ID NO: |
|---|---|---|
| LMNA exon 11 | GGCTCCCACTGCAGCAGCTCGGGGG ACCCCGCTGAGTACAACCTGCGCTC GCGCACCGTGCTGTGCGGGACCTGC GGGCAGCCTGCCGACAAGGCATCTG CCAGCGGCTCAGGAGCCCAGGTGGG CGGACCCATCTCCTCTGGCTCTTCT GCCTCCAGTGTCACGGTCACTCGCA GCTACCGCAGTGTGGGGGGCAGTGG GGGTGGCAGCTTCGGGGACAATCTG GTCACCCGCTCCTACCTCCTGGGCA ACTCCAGCCCCCGAACCCAG | 1 |
| HGPS exon 11 | GGCTCCCACTGCAGCAGCTCGGGGG ACCCCGCTGAGTACAACCTGCGCTC GCGCACCGTGCTGTGCGGGACCTGC GGGCAGCCTGCCGACAAGGCATCTG CCAGCGGCTCAGGAGCCCAGGTGGG TGGACCCATCTCCTCTGGCTCTTCT GCCTCCAGTGTCACGGTCACTCGCA GCTACCGCAGTGTGGGGGGCAGTGG GGGTGGCAGCTTCGGGGACAATCTG GTCACCCGCTCCTACCTCCTGGGCA ACTCCAGCCCCCGAACCCAG | 2 |
| Exo11.25.133 | CCGCTGGCAGATGCCTTGTCGGCAG | 3 |
| Exo11.25.138 | CTGAGCCGCTGGCAGATGCCTTGT | 4 |
| Exo11.25.142 | GCTCCTGAGCCGCTGGCAGATGCCT | 5 |
| Exo11.25.145 | TGGGCTCCTGAGCCGCTGGCAGATG | 6 |
| Exo11.25.149 | CACCTGGGCTCCTGAGCCGCTGGCA | 7 |
| Exo11.25.154 | CCACCCACCTGGGCTCCTGAGCCGC | 8 |
| Exo11.25.158 | GGGTCCACCCACCTGGGCTCCTGAG | 9 |
| Exo11.25.162 | AGATGGGTCCACCCACCTGGGCTCC | 10 |
| Exo11.25.166 | GAGGAGATGGGTCCACCCACCTGGG | 11 |
| Exo11.25.170 | GCCAGAGGAGATGGGTCCACCCACC | 12 |
| Exo11.25.174 | AAGAGCCAGAGGAGATGGGTCCACC | 13 |
| Exo11.25.177 | CAGAAGAGCCAGAGGAGATGGGTCC | 14 |
| Exo11.25.181 | GAGGCAGAAGAGCCAGAGGAGATGG | 15 |

SEQUENCE LISTING TABLE

| NAME | SEQUENCE | SEQ ID NO: |
|---|---|---|
| Exo11.25.185 | ACTGGAGGCAGAAGAGCCAGAGGAG | 16 |
| Exo10SD.25.69 | ACGTGGTGGTGATGGAGCAGGTCAT | 17 |
| Exo10SD.25.73 | ACTCACGTGGTGGTGATGGAGCAGG | 18 |
| Exo10SD.25.79 | GCTACCACTCACGTGGTGGTGATGG | 19 |
| Exo10SD.25.84 | CGGCGGCTACCACTCACGTGGTGGT | 20 |
| Exo10SD.25.87 | CAGCGGCGGCTACCACTCACGTGGT | 21 |
| Exo10SD.25.90 | CCTCAGCGGCGGCTACCACTCACGT | 22 |
| Exo10SD.25.92 | GGCCTCAGCGGCGGCTACCACTCAC | 23 |
| Exo10SD.25.96 | GCTCGGCCTCAGCGGCGGCTACCAC | 24 |
| Exo11SA.25.779 | CGAGTCTGGGACTGACCACTCAGGC | 25 |
| Exo11SA.25.796 | AGGCTCAGGCGGGACGGCGAGTCTG | 26 |
| Exo11SA.25.801 | AGACAAGGCTCAGGCGGGACGGCGA | 27 |
| Exo11SA.25.805 | AGGGAGACAAGGCTCAGGCGGGACG | 28 |
| Exo11SA.25.809 | GGGAAGGGAGACAAGGCTCAGGCGG | 29 |
| Exo11SA.25.814 | GCCCTGGGAAGGGAGACAAGGCTCA | 30 |
| Exo11SA.25.820 | GTGGGAGCCCTGGGAAGGGAGACAA | 31 |
| Exo11SA.25.828 | CTGCTGCAGTGGGAGCCCTGGGAAG | 32 |
| Exo11SA.25.830 | AGCTGCTGCAGTGGGAGCCCTGGGA | 33 |
| Exo11SA.25.836 | CCCCCGAGCTGCTGCAGTGGGAGCC | 34 |
| HsEx10 | GCTACCACTCACGTGGTGGTGATGG-AcR$_6$G | 35 |
| HsEx11 | GGGTCCACCCACCTGGGCTCCTGAG-AcR$_6$G | 36 |
| HsEx10-apn | GC$^{apn}$TACCAC$^{apn}$TCACG$^{apn}$TGGTGG$^{apn}$TGATGG | 37 |
| HsEx11-apn | GGG$^{apn}$TCCACCCACC$^{apn}$TGGGC$^{apn}$TCC$^{apn}$TGAG | 38 |
| rTAT | RRRQRRKKR | 39 |
| Tat | RKKRRQRRR | 40 |
| R$_9$F$_2$ | RRRRRRRRRFF | 41 |
| R$_5$F$_2$R$_4$ | RRRRRFFRRRR | 42 |
| R$_4$ | RRRR | 43 |
| R$_5$ | RRRRR | 44 |
| R$_6$ | RRRRRR | 45 |
| R$_7$ | RRRRRRR | 46 |

-continued

SEQUENCE LISTING TABLE

| NAME | SEQUENCE | SEQ ID NO: |
|---|---|---|
| $R_8$ | RRRRRRRR | 47 |
| $R_9$ | RRRRRRRRR | 48 |
| $(RX)_8$ | RXRXRXRXRXRXRXRX | 49 |
| $(RAhxR)_4$; (P007) | RAhxRRAhxRRAhxRRAhxR | 50 |
| $(RAhxR)_5$; (CP04057) | RAhxRRAhxRRAhxRRAhxRRAhxR | 51 |
| $(RAhxRRBR)_2$; (CP06062) | RAhxRRBRRAhxRRBR | 52 |
| $(RAR)_4F_2$ | RARRARRARRARFFC | 53 |
| $(RGR)_4F_2$ | RGRRGRRGRRGRFFC | 54 |

EXAMPLES

Example 1

Treatment of HGPS Cells Using Antisense Oligonucleotides Targeting LMNA

Two primary fibroblasts lines were used, HGPS fibroblasts (HGADFN167) and control fibroblasts (HGFDFN168). HGPS and control cells were seeded into a 24-well dish at the density of about 10,000 cells/well. Morpholino oligonucleotides targeted to exons 11 and/or 10 of Lamin-A pre-mRNA were individually introduced into cultured HGPS cells either by free uptake or by nucleofection (Amaxa, for example). For free uptake, cells were cultured for 1-2 weeks in a medium containing either 25 µM or 50 µM or 80 uM of PMO oligonucleotides. Those cells were then screened by immunofluorescence with anti-progerin or anti-lamin A/C antibodies. The fluorescence intensities of progerin staining were quantified using Zeiss fluorescence microscope and a SPOT program. The experiments were performed in triplicate, and the PMOs that showed effects in down-regulating progerin were selected for further analysis. Analysis included quantitative RT-PCR with progerin-specific primer and Western blotting analysis with anti-progerin antibodies.

Example 2

Immunofluorescence Staining of HGPS Cells Following Treatment with Antisense Oligonucleotides Targeting LMNA Immunofluorescence Staining:
For immunofluorescence, cells were seeded onto 4-well chamber slides. After fixation in 4% paraformaldehyde/PBS at room temperature for 15 min, cells were permeabilized with 0.5% Triton X-100/PBS at room temperature for 5 min, followed by an overnight incubation in the blocking solution at 4° C. (Blocking solution: 4% BSA/TBS). Cells were stained with mouse monoclonal anti-lamin A/C (MAB3211, Chemicon) and rabbit polyclonal anti-progerin (custom peptide antibody, Yenzm) for 3 hours at room temperature on the following day. Primary antibodies were detected with Alexa Fluor-labeled secondary antibodies (Invitrogen). Slides mounted with Vectashield mounting medium containing DAPI were observed with a Zeiss fluorescence microscope. Exposure times and acquisition settings were established at the beginning of each set of experiments and kept constant for all treatments. The results of the experiments are set forth in FIG. 2. Several of the oligonucleotides significantly down-regulated progerin.

Example 3

Figure 3:
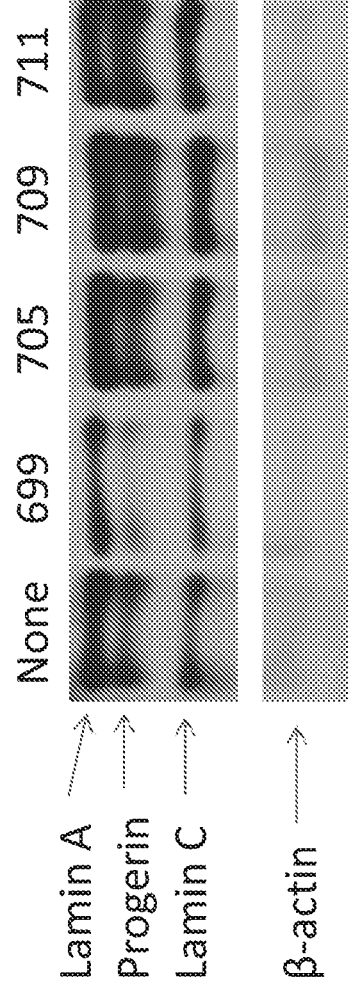
FIG. 3 shows results for Western analysis of lamin A and progerin.
Figure 3:

SDS-Page and Western Blotting Analysis of HGPS Cells Following Treatment with Antisense Oligonucleotides Targeting LMNA SDS-PAGE and Western Blotting Analysis:
Treated cells were collected, rinsed twice in PBS, and then lysed in Laemmli SDS-PAGE loading buffer. Samples were heated for 15 minutes at 95° C. and then loaded onto 10% SDS-PAGE gels. As for western blot analysis, proteins were transferred onto the nitrocellulose membranes. Membranes were blocked with 5% milk/TBST at 4° C. for overnight and incubated with primary antibodies diluted in 4% BSA/TBST at room temperature for 1-3 hours. After washes with TBST, the membranes were incubated in secondary antibodies diluted at 1:5000 in 1% milk/TBST for 1 hour at room temperature. The chemiluminescence was detected with an ECL western blotting detection kit (Pierce). Primary antibodies used include mouse monoclonal anti-lamin A/C (MAB3211, Chemicon), rabbit polyclonal anti-progerin (custom peptide antibody, Yenzm) and rabbit polyclonal anti-actin (Pan-actin, Cell Signaling). The results of the experiments are set forth in FIG. 3. The oligonucleotide corresponding to 699 (SEQ ID NO: 4) showed significant down-regulation of progerin in the experiment, despite it being removed from, and not overlapping with, the exon 11 cryptic splice site of LMNA.

Example 4

Figure 4:
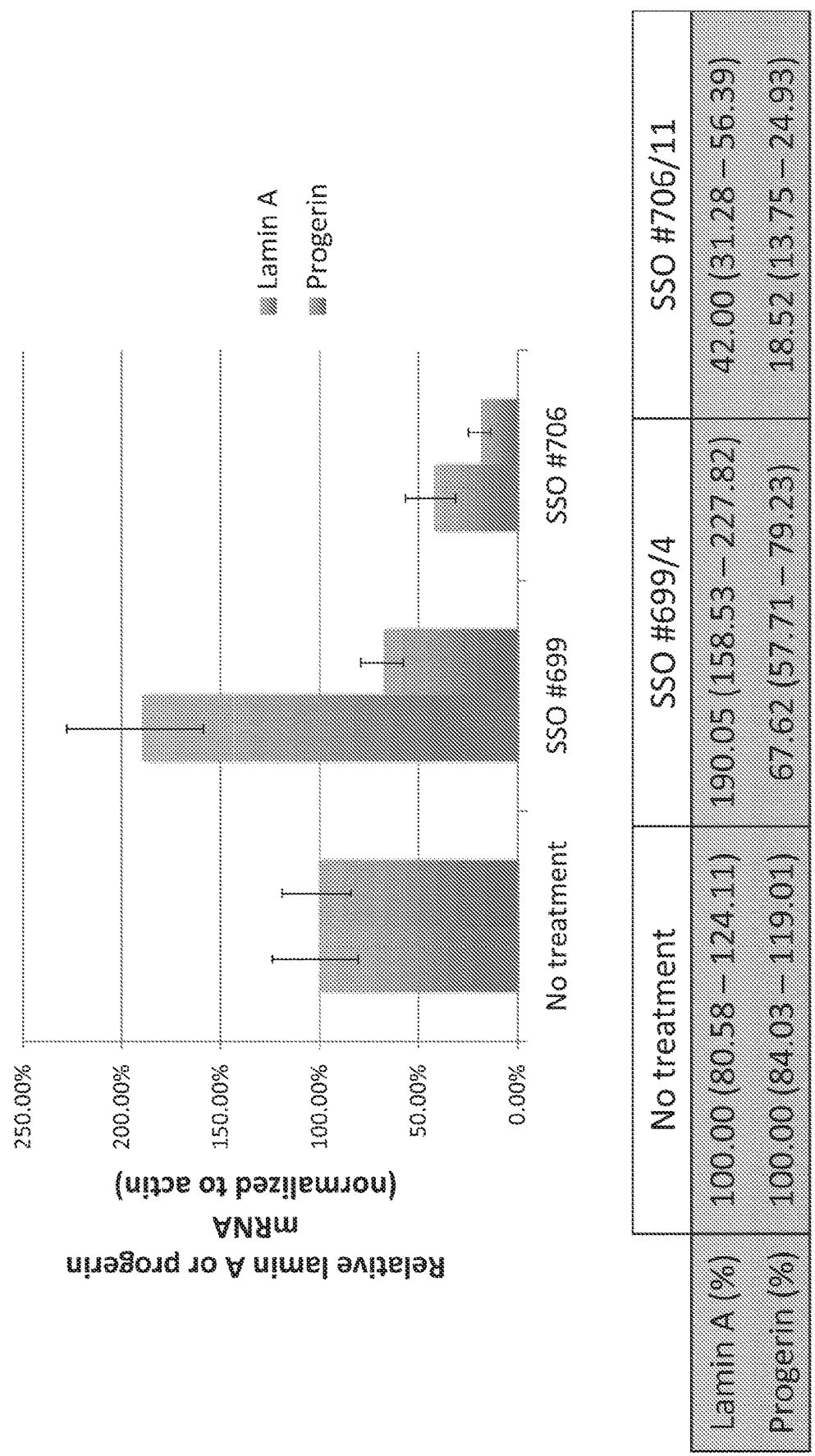
FIG. 4 shows results for RT-qPCR analysis of lamin A and progerin.

Quantitative RT-PCR Analysis of HGPS Cells Following Treatment with Antisense Oligonucleotides Targeting LMNA Quantitative RT-PCR:
Quantitative RT-PCR (qRT-PCR) experiments were performed to measure the expression levels of progerin, lamin A and β-actin in 164 fibroblasts (p13, classical HGPS) following treatment with oligonucleotide 699 (SEQ ID NO: 4) and 706 (SEQ ID NO: 11). All reactions were carried out in triplicate on an Applied Biosystems 7900HT Fast Real-Time PCR System using SYBR Green mix (Qiagen) according to the manufacturer's instructions. Reaction conditions were as follows: 1 cycles of 2 min at 50° C.; 1 cycle of 15 min at 95° C.; and 40 cycles of 15 s at 95° C., 1 min at 57° C., and 45 s at 72° C. The sequence for the 13-actin forward primer is TCTTTGCAGCCACATTCCCG and reverse primer is GGCTTGCGGGTGTTAAAAGC. The sequence of the forward primer for amplifying progerin/lamin A is GCAACAAGTCCAATGAGGACCA. The progerin- and lamin A-specific reverse primers were designed according to amplification-refractory mutation system strategy, by introducing a mutation at the penultimate base to increase specificity. The progerin-specific primer sequence is CATGATGCTGCAGTTCTGGGGGCTCTGGAC, and that for lamin A is CATGATGCTGCAGTTCTGGGGGCTCTG-GAT. The results of the experiments are set forth in FIG. 4.

Example 5

Figure 5:
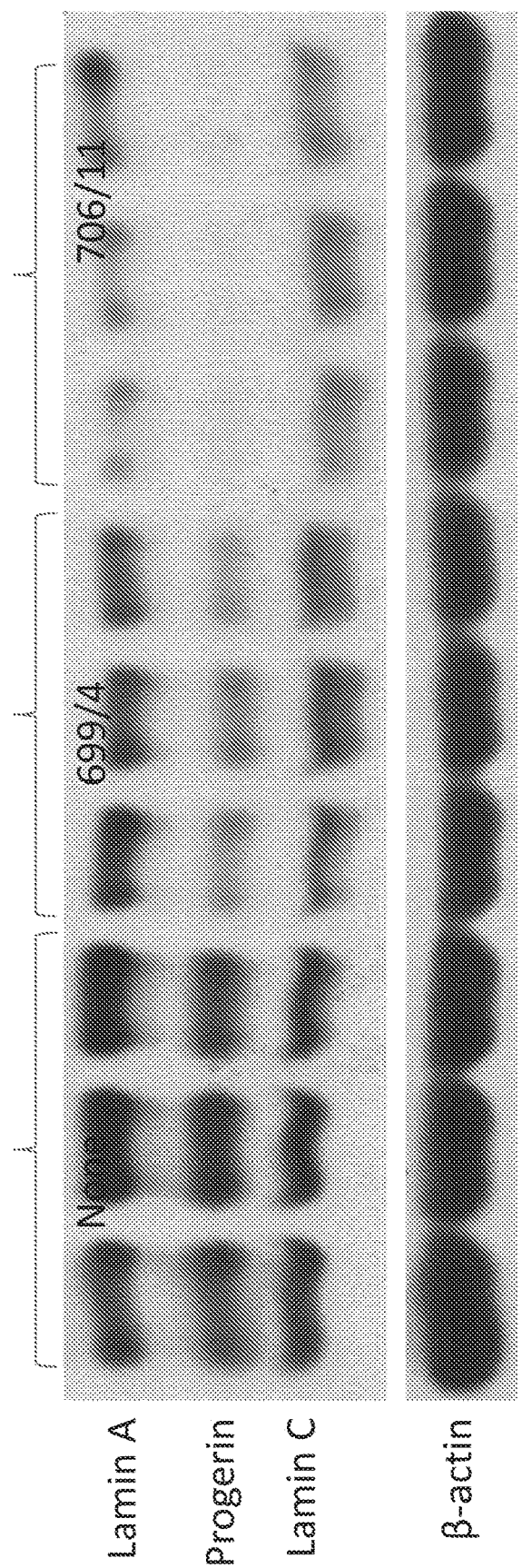
FIG. 5 shows results for Western analysis of lamin A, lamin C and progerin.

SDS-Page and Western Blotting Analysis of HGPS Cells Following Treatment with Antisense Oligonucleotides Targeting LMNA SDS-PAGE and Western Blotting Analysis:

Treated cells were collected, rinsed twice in PBS, and then lysed in Laemmli SDS-PAGE loading buffer. Samples were heated for 15 minutes at 95° C. and then loaded onto 10% SDS-PAGE gels. As for western blot analysis, proteins were transferred onto the nitrocellulose membranes. Membranes were blocked with 5% milk/TBST at 4° C. for overnight and incubated with primary antibodies diluted in 4% BSA/TBST at room temperature for 1-3 hours. After washes with TBST, the membranes were incubated in secondary antibodies diluted at 1:5000 in 1% milk/TBST for 1 hour at room temperature. The chemiluminescence was detected with an ECL western blotting detection kit (Pierce). Primary antibodies used include mouse monoclonal anti-lamin A/C (MAB3211, Chemicon), rabbit polyclonal anti-progerin (custom peptide antibody, Yenzm) and horseradish peroxidase (HRP)-conjugated anti-actin (Sigma). The results of the experiments are set forth in FIG. 5. Oligo-nucleotide 699 (SEQ ID NO: 4) gave rise to a down-regulation of progerin and an up-regulation of lamin A, despite it being removed from, and not overlapping with, the exon 11 cryptic splice site of LMNA.

REFERENCES

Cao, K., C. D. Blair, et al. (2011). "Progerin and telomere dysfunction collaborate to trigger cellular senescence in normal human fibroblasts." *J Clin Invest*.

Egholm, M., O. Buchardt, et al. (1993). "PNA hybridizes to complementary oligonucleotides obeying the Watson-Crick hydrogen-bonding rules." *Nature* 365(6446): 566-8.

Kinali, M., V. Arechavala-Gomeza, et al. (2009). "Local restoration of dystrophin expression with the morpholino oligomer AVI-4658 in Duchenne muscular dystrophy: a single-blind, placebo-controlled, dose-escalation, proof-of-concept study." *Lancet Neurol* 8(10): 918-28.

Osorio, F. G., C. L. Navarro, et al. (2011). "Splicing-directed therapy in a new mouse model of human accelerated aging." *Sci Transl Med* 3(106): 106ra107.

Scaffidi, P. and T. Misteli (2005). "Reversal of the cellular phenotype in the premature aging disease Hutchinson-Gilford progeria syndrome." *Nat Med* 11(4): 440-5.

Svasti, S., T. Suwanmanee, et al. (2009). "RNA repair restores hemoglobin expression in IVS2-654 thalassemic mice." *Proc Natl Acad Sci USA* 106(4): 1205-10.

The invention claimed is:

1. An antisense oligonucleotide for use in modulating aberrant splicing of a human LMNA pre-mRNA, the oligonucleotide being composed of morpholino subunits and phosphorus-containing intersubunit linkages joining a morpholino nitrogen of one subunit to a 5'-exocyclic carbon of an adjacent subunit, and:
   (i) having a substantially uncharged, nuclease resistant backbone;
   (ii) capable of uptake by mammalian host cells;
   (iii) containing between about 12-40 nucleotide bases; and
   (iv) having a targeting sequence of at least about 12 contiguous subunits complementary to exon 10, intron 10, exon 11, or combinations thereof, of a human LMNA pre-mRNA; and
   wherein the targeting sequence comprises any one of SEQ ID NOs: 3-7, 11, or 14-16.

2. The oligonucleotide of claim 1, where the targeting sequence consists essentially of SEQ ID NO: 4.

3. The oligonucleotide of claim 1, where the targeting sequence consists essentially of SEQ ID NO: 11.

4. The oligonucleotide of claim 1, where the morpholino subunits in the oligonucleotide are joined by phosphorodiamidate linkages, in accordance with the following structure:

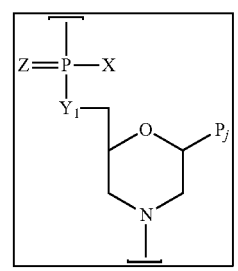

wherein Z is S or O,
X=NR$^1$R$^2$ or OR$^6$,
Y=O or NR$^7$,
and each said linkage is selected from:
(a) uncharged linkage (a), wherein each of R$^1$, R$^2$, R$^6$, and R$^7$ is independently selected from hydrogen and lower alkyl;

(b1) cationic linkage (b1), wherein $X=NR^1R^2$ and $Y=O$, and $NR^1R^2$ represents an optional substituted piperazino group, such that $R^1R^2=$ —CHRCHRN($R^3$)($R^4$)CHRCHR—, wherein
each $R^4$ is H, $CH_3$ or null, and
R3 is selected from H, lower alkyl, $C(=NH)NH_2$, Z—L—$NHC(=NH)NH_2$, and $[C(O)CHR'NH]_mH$, wherein where Z is carbonyl (C(O)) or a direct bond, L is an optional linker up to 18 atoms in length having bonds selected from alkyl, alkoxy, and alkylamino, R' is a side chain of a naturally occurring amino acid or a one- or two-carbon homolog thereof, and m is 1 to 6;
(b2) cationic linkage (b2), wherein $X=NR^1R^2$ and $Y=O$, $R^1=H$ or $CH_3$, and $R^2=LNR^3R^4R^5$, wherein L, $R^3$, and $R^4$ are defined as above, and $R^5$ is H, lower alkyl, or lower (alkoxy)alkyl; and
(b3) cationic linkage (b3), wherein $Y=NR^7$ and $X=OR^6$, and $R7=LNR^3R^4R^5$. wherein L, $R^3$, and $R^4$ and $R^5$ are defined as above, and $R^6$ is H or lower alkyl; and at least one said linkage is selected from cationic linkages (b1), (b2), and (b3).

5. The oligonucleotide of claim 4, where each of $R^1$ and $R^2$, in linkages of type (a), is methyl.

6. The oligonucleotide of claim 4, where at least one linkage is of type (b1), where each R is H, $R^4$ is H, $CH_3$, or an electron pair, and $R^3$ is selected from H, $CH_3$, $C(=NH)NH_2$, and $C(O)$—L—$NHC(=NH)NH_2$.

7. The oligonucleotide of claim 1, where the antisense oligonucleotide is covalently attached to a cell-penetrating peptide.

8. The oligonucleotide of claim 7, where the cell-penetrating peptide is an arginine-rich peptide.

9. The oligonucleotide of claim 8, where the peptide is attached at its C-terminus to the 3' end of the oligonucleotide through a one- or two-amino acid linker.

10. An antisense oligonucleotide, or a pharmaceutical composition comprising the same, wherein the oligonucleotide modulates aberrant splicing of a human LMNA pre-mRNA, the oligonucleotide comprising a backbone, the backbone comprising a sequence of morpholino ring structures joined by intersubunit linkages, the intersubunit linkages joining a 3'-end of one morpholino ring structure to a 5'-end of an adjacent morpholino ring structure, wherein each morpholino ring structure is bound to a base-pairing moiety, such that the oligonucleotide can bind in a sequence-specific manner to a target nucleic acid, comprising a targeting sequence that is complementary to at least 12 bases of a sequence set forth in any one of SEQ ID NO:1-34, or which comprises any one or more of SEQ ID NOS: 3-34, wherein the intersubunit linkages have the following general structure (I):

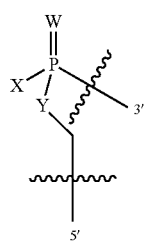

(I)

or a salt or isomer thereof, and wherein each of the intersubunit linkages (I) are independently linkage (A) or linkage (B):
wherein for linkage (A):
W is, at each occurrence, independently S or O;
X is, at each occurrence, independently —$N(CH_3)_2$, —$NR^1R^2$, —$OR^3$ or ;

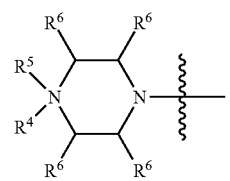

(II)

Y is, at each occurrence, independently O or —$NR^2$,
$R^1$ is, at each occurrence, independently hydrogen or methyl;
$R^2$ is, at each occurrence, independently hydrogen or —$LNR^4R^5R^7$;
$R^3$ is, at each occurrence, independently hydrogen or $C_1$-$C_6$ alkyl;
$R^4$ is, at each occurrence, independently hydrogen, methyl, —$C(=NH)NH_2$, —Z—L—$NHC(=NH)NH_2$ or —$[C(O)CHR'NH]_mH$, where Z is carbonyl (C(O)) or a direct bond, R' is a side chain of a naturally occurring amino acid or a one- or two-carbon homolog thereof, and m is 1 to 6;
$R^5$ is, at each occurrence, independently hydrogen, methyl or an electron pair;
$R^6$ is, at each occurrence, independently hydrogen or methyl;
$R^7$ is, at each occurrence, independently hydrogen $C_1$-$C_6$ alkyl or $C_1$-$C_6$ alkoxyalkyl;
L is an optional linker up to 18 atoms in length comprising alkyl, alkoxy or alkylamino groups, or combinations thereof; and
wherein for linkage (B):
W is, at each occurrence, independently S or O;
X is, at each occurrence, independently —$NR^8R^9$ or —$OR^3$; and
Y is, at each occurrence, independently O or —$NR^{10}$,
$R^8$ is, at each occurrence, independently hydrogen or $C_2$-$C_{12}$ alkyl;
$R^9$ is, at each occurrence, independently hydrogen, $C_1$-$C_{12}$ alkyl, $C_1$-$C_{12}$ aralkyl or aryl;
$R_{10}$ is, at each occurrence, independently hydrogen, $C_1$-$C_{12}$ alkyl or —$LNR^4R^5R^7$;
wherein $R^8$ and $R^9$ may join to form a 5-18 membered mono or bicyclic heterocycle or $R^8$, $R^9$ or $R^3$ may join with $R^{10}$ to form a 5-7 membered heterocycle, and wherein when X is 4-piparazino, X has the following structure (III):

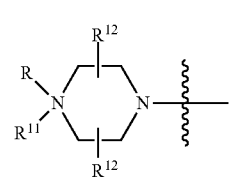

(III)

wherein:

$R^{11}$ is, at each occurrence, independently $C_2$-$C_{12}$ alkyl, $C_1$-$C_{12}$ aminoalkyl, $C_1$-$C_{12}$ alkylcarbonyl, aryl, heteroaryl or heterocyclyl; and R is, at each occurrence, independently an electron pair, hydrogen or $C_1$-$C_{12}$ alkyl; and $R^{12}$ is, at each occurrence, independently, hydrogen, $C_1$-$C_{12}$ alkyl, $C_1$-$C_{12}$ aminoalkyl, —$NH_2$, —$NR^{13}R^{14}$, —$NR^{13}R^{14}R^{15}$, $C_1$-$C_{12}$ alkylcarbonyl, oxo, —CN, trifluoromethyl, amidyl, amidinyl, amidinylalkyl, amidinylalkylcarbonyl guanidinyl, guanidinylalkyl, guanidinylalkylcarbonyl, cholate, deoxycholate, aryl, heteroaryl, heterocycle, —$SR^{13}$ or $C_1$-$C_{12}$ alkoxy, wherein $R^{13}$, $R^{14}$ and $R^{15}$ are, at each occurrence, independently $C_1$-$C_{12}$ alkyl;

wherein at least one of the intersubunit linkages is linkage (B); and wherein the targeting sequence comprises any one of SEQ ID NOs: 3-7, 11, or 14-16.

11. The oligonucleotide of claim 10, where the targeting sequence consists essentially of SEQ ID NO: 4.

12. The oligonucleotide of claim 10, where the targeting sequence consists essentially of SEQ ID NO: 11.

* * * * *

SEQUENCE LISTING

```
<160> NUMBER OF SEQ ID NOS: 59

<210> SEQ ID NO 1
<211> LENGTH: 270
<212> TYPE: DNA
<213> ORGANISM: Artificial Sequence
<220> FEATURE:
<223> OTHER INFORMATION: Exemplary LMNA Target Sequence

<400> SEQUENCE: 1
ggctcccact gcagcagctc gggggacccc gctgagtaca acctgcgctc gcgcaccgtg      60
ctgtgcggga cctgcgggca gcctgccgac aaggcatctg ccagcggctc aggagcccag     120
gtgggcggac ccatctcctc tggctcttct gcctccagtg tcacggtcac tcgcagctac     180
cgcagtgtgg ggggcagtgg gggtggcagc ttcggggaca atctggtcac ccgctcctac     240
ctcctgggca actccagccc ccgaacccag                                      270

<210> SEQ ID NO 2
<211> LENGTH: 270
<212> TYPE: DNA
<213> ORGANISM: Artificial Sequence
<220> FEATURE:
<223> OTHER INFORMATION: Exemplary LMNA Target Sequence

<400> SEQUENCE: 2
ggctcccact gcagcagctc gggggacccc gctgagtaca acctgcgctc gcgcaccgtg      60
ctgtgcggga cctgcgggca gcctgccgac aaggcatctg ccagcggctc aggagcccag     120
gtgggtggac ccatctcctc tggctcttct gcctccagtg tcacggtcac tcgcagctac     180
cgcagtgtgg ggggcagtgg gggtggcagc ttcggggaca atctggtcac ccgctcctac     240
ctcctgggca actccagccc ccgaacccag                                      270

<210> SEQ ID NO 3
```

```
<211> LENGTH: 25
<212> TYPE: DNA
<213> ORGANISM: Artificial Sequence
<220> FEATURE:
<223> OTHER INFORMATION: Exemplary HGPS Targeting Sequence

<400> SEQUENCE: 3
ccgctggcag atgccttgtc ggcag                                              25

<210> SEQ ID NO 4
<211> LENGTH: 25
<212> TYPE: DNA
<213> ORGANISM: Artificial Sequence
<220> FEATURE:
<223> OTHER INFORMATION: Exemplary HGPS Targeting Sequence

<400> SEQUENCE: 4
ctgagccgct ggcagatgcc ttgtc                                              25

<210> SEQ ID NO 5
<211> LENGTH: 25
<212> TYPE: DNA
<213> ORGANISM: Artificial Sequence
<220> FEATURE:
<223> OTHER INFORMATION: Exemplary HGPS Targeting Sequence

<400> SEQUENCE: 5
gctcctgagc cgctggcaga tgcct                                              25

<210> SEQ ID NO 6
<211> LENGTH: 25
<212> TYPE: DNA
<213> ORGANISM: Artificial Sequence
<220> FEATURE:
<223> OTHER INFORMATION: Exemplary HGPS Targeting Sequence

<400> SEQUENCE: 6
tgggctcctg agccgctggc agatg                                              25

<210> SEQ ID NO 7
<211> LENGTH: 25
<212> TYPE: DNA
<213> ORGANISM: Artificial Sequence
<220> FEATURE:
<223> OTHER INFORMATION: Exemplary HGPS Targeting Sequences

<400> SEQUENCE: 7
cacctgggct cctgagccgc tggca                                              25

<210> SEQ ID NO 8
<211> LENGTH: 25
<212> TYPE: DNA
<213> ORGANISM: Artificial Sequence
<220> FEATURE:
<223> OTHER INFORMATION: Exemplary HGPS Targeting Sequence

<400> SEQUENCE: 8
ccacccacct gggctcctga gccgc                                              25

<210> SEQ ID NO 9
<211> LENGTH: 25
<212> TYPE: DNA
<213> ORGANISM: Artificial Sequence
<220> FEATURE:
<223> OTHER INFORMATION: Exemplary HGPS Targeting Sequence

<400> SEQUENCE: 9
```
gggtccaccc acctgggctc ctgag                                              25

<210> SEQ ID NO 10
<211> LENGTH: 25
<212> TYPE: DNA
<213> ORGANISM: Artificial Sequence
<220> FEATURE:
<223> OTHER INFORMATION: Exemplary HGPS Targeting Sequence

<400> SEQUENCE: 10
agatgggtcc acccacctgg gctcc                                              25

<210> SEQ ID NO 11
<211> LENGTH: 25
<212> TYPE: DNA
<213> ORGANISM: Artificial Sequence
<220> FEATURE:
<223> OTHER INFORMATION: Exemplary HGPS Targeting Sequence

<400> SEQUENCE: 11
gaggagatgg gtccacccac ctggg                                              25

<210> SEQ ID NO 12
<211> LENGTH: 25
<212> TYPE: DNA
<213> ORGANISM: Artificial Sequence
<220> FEATURE:
<223> OTHER INFORMATION: Exemplary HGPS Targeting Sequence

<400> SEQUENCE: 12
gccagaggag atgggtccac ccacc                                              25

<210> SEQ ID NO 13
<211> LENGTH: 25
<212> TYPE: DNA
<213> ORGANISM: Artificial Sequence
<220> FEATURE:
<223> OTHER INFORMATION: Exemplary HGPS Targeting Sequence

<400> SEQUENCE: 13
aagagccaga ggagatgggt ccacc                                              25

<210> SEQ ID NO 14
<211> LENGTH: 25
<212> TYPE: DNA
<213> ORGANISM: Artificial Sequence
<220> FEATURE:
<223> OTHER INFORMATION: Exemplary HGPS Targeting Sequence

<400> SEQUENCE: 14
cagaagagcc agaggagatg ggtcc                                              25

<210> SEQ ID NO 15
<211> LENGTH: 25
<212> TYPE: DNA
<213> ORGANISM: Artificial Sequence
<220> FEATURE:
<223> OTHER INFORMATION: Exemplary HGPS Targeting Sequence

<400> SEQUENCE: 15
gaggcagaag agccagagga gatgg                                              25

<210> SEQ ID NO 16
<211> LENGTH: 25
<212> TYPE: DNA

```
<213> ORGANISM: Artificial Sequence
<220> FEATURE:
<223> OTHER INFORMATION: Exemplary HGPS Targeting Sequence

<400> SEQUENCE: 16
actggaggca gaagagccag aggag                                              25

<210> SEQ ID NO 17
<211> LENGTH: 25
<212> TYPE: DNA
<213> ORGANISM: Artificial Sequence
<220> FEATURE:
<223> OTHER INFORMATION: Exemplary HGPS Targeting Sequence

<400> SEQUENCE: 17
acgtggtggt gatggagcag gtcat                                              25

<210> SEQ ID NO 18
<211> LENGTH: 25
<212> TYPE: DNA
<213> ORGANISM: Artificial Sequence
<220> FEATURE:
<223> OTHER INFORMATION: Exemplary HGPS Targeting Sequence

<400> SEQUENCE: 18
actcacgtgg tggtgatgga gcagg                                              25

<210> SEQ ID NO 19
<211> LENGTH: 25
<212> TYPE: DNA
<213> ORGANISM: Artificial Sequence
<220> FEATURE:
<223> OTHER INFORMATION: Exemplary HGPS Targeting Sequence

<400> SEQUENCE: 19
gctaccactc acgtggtggt gatgg                                              25

<210> SEQ ID NO 20
<211> LENGTH: 25
<212> TYPE: DNA
<213> ORGANISM: Artificial Sequence
<220> FEATURE:
<223> OTHER INFORMATION: Exemplary HGPS Targeting Sequence

<400> SEQUENCE: 20
cggcggctac cactcacgtg gtggt                                              25

<210> SEQ ID NO 21
<211> LENGTH: 25
<212> TYPE: DNA
<213> ORGANISM: Artificial Sequence
<220> FEATURE:
<223> OTHER INFORMATION: Exemplary HGPS Targeting Sequence

<400> SEQUENCE: 21
cagcggcggc taccactcac gtggt                                              25

<210> SEQ ID NO 22
<211> LENGTH: 25
<212> TYPE: DNA
<213> ORGANISM: Artificial Sequence
<220> FEATURE:
<223> OTHER INFORMATION: Exemplary HGPS Targeting Sequence

<400> SEQUENCE: 22
cctcagcggc ggctaccact cacgt                                              25
```

<210> SEQ ID NO 23
<211> LENGTH: 25
<212> TYPE: DNA
<213> ORGANISM: Artificial Sequence
<220> FEATURE:
<223> OTHER INFORMATION: Exemplary HGPS Targeting Sequence

<400> SEQUENCE: 23
ggcctcagcg gcggctacca ctcac                               25

<210> SEQ ID NO 24
<211> LENGTH: 25
<212> TYPE: DNA
<213> ORGANISM: Artificial Sequence
<220> FEATURE:
<223> OTHER INFORMATION: Exemplary HGPS Targeting Sequence

<400> SEQUENCE: 24
gctcggcctc agcggcggct accac                               25

<210> SEQ ID NO 25
<211> LENGTH: 25
<212> TYPE: DNA
<213> ORGANISM: Artificial Sequence
<220> FEATURE:
<223> OTHER INFORMATION: Exemplary HGPS Targeting Sequence

<400> SEQUENCE: 25
cgagtctggg actgaccact caggc                               25

<210> SEQ ID NO 26
<211> LENGTH: 25
<212> TYPE: DNA
<213> ORGANISM: Artificial Sequence
<220> FEATURE:
<223> OTHER INFORMATION: Exemplary HGPS Targeting Sequence

<400> SEQUENCE: 26
aggctcaggc gggacggcga gtctg                               25

<210> SEQ ID NO 27
<211> LENGTH: 25
<212> TYPE: DNA
<213> ORGANISM: Artificial Sequence
<220> FEATURE:
<223> OTHER INFORMATION: Exemplary HGPS Targeting Sequence

<400> SEQUENCE: 27
agacaaggct caggcgggac ggcga                               25

<210> SEQ ID NO 28
<211> LENGTH: 25
<212> TYPE: DNA
<213> ORGANISM: Artificial Sequence
<220> FEATURE:
<223> OTHER INFORMATION: Exemplary HGPS Targeting Sequence

<400> SEQUENCE: 28
agggagacaa ggctcaggcg ggacg                               25

<210> SEQ ID NO 29
<211> LENGTH: 25
<212> TYPE: DNA
<213> ORGANISM: Artificial Sequence
<220> FEATURE:

<223> OTHER INFORMATION: Exemplary HGPS Targeting Sequence

<400> SEQUENCE: 29
gggaagggag acaaggctca ggcgg                                              25

<210> SEQ ID NO 30
<211> LENGTH: 25
<212> TYPE: DNA
<213> ORGANISM: Artificial Sequence
<220> FEATURE:
<223> OTHER INFORMATION: Exemplary HGPS Targeting Sequence

<400> SEQUENCE: 30
gccctgggaa gggagacaag gctca                                              25

<210> SEQ ID NO 31
<211> LENGTH: 25
<212> TYPE: DNA
<213> ORGANISM: Artificial Sequence
<220> FEATURE:
<223> OTHER INFORMATION: Exemplary HGPS Targeting Sequence

<400> SEQUENCE: 31
gtgggagccc tgggaaggga gacaa                                              25

<210> SEQ ID NO 32
<211> LENGTH: 25
<212> TYPE: DNA
<213> ORGANISM: Artificial Sequence
<220> FEATURE:
<223> OTHER INFORMATION: Exemplary HGPS Targeting Sequence

<400> SEQUENCE: 32
ctgctgcagt gggagccctg ggaag                                              25

<210> SEQ ID NO 33
<211> LENGTH: 25
<212> TYPE: DNA
<213> ORGANISM: Artificial Sequence
<220> FEATURE:
<223> OTHER INFORMATION: Exemplary HGPS Targeting Sequence

<400> SEQUENCE: 33
agctgctgca gtgggagccc tggga                                              25

<210> SEQ ID NO 34
<211> LENGTH: 25
<212> TYPE: DNA
<213> ORGANISM: Artificial Sequence
<220> FEATURE:
<223> OTHER INFORMATION: Exemplary HGPS Targeting Sequence

<400> SEQUENCE: 34
cccccgagct gctgcagtgg gagcc                                              25

<210> SEQ ID NO 35
<211> LENGTH: 25
<212> TYPE: DNA
<213> ORGANISM: Artificial Sequence
<220> FEATURE:
<223> OTHER INFORMATION: Exemplary HGPS Targeting Sequence
<220> FEATURE:
<221> NAME/KEY: misc_feature
<222> LOCATION: (25)...(25)
<223> OTHER INFORMATION: conjugated with a glycine linker to a preferred
      cell-penetrating peptide transporter AcR6G

<400> SEQUENCE: 35
gctaccactc acgtggtggt gatgg                                          25

<210> SEQ ID NO 36
<211> LENGTH: 25
<212> TYPE: DNA
<213> ORGANISM: Artificial Sequence
<220> FEATURE:
<223> OTHER INFORMATION: Exemplary HGPS Targeting Sequence
<220> FEATURE:
<221> NAME/KEY: misc_feature
<222> LOCATION: (25)..(25)
<223> OTHER INFORMATION: conjugated with a glycine linker to a preferred
      cell-penetrating peptide transporter AcR6G

<400> SEQUENCE: 36
gggtccaccc acctgggctc ctgag                                          25

<210> SEQ ID NO 37
<211> LENGTH: 25
<212> TYPE: DNA
<213> ORGANISM: Artificial Sequence
<220> FEATURE:
<223> OTHER INFORMATION: Exemplary HGPS Targeting Sequence
<220> FEATURE:
<221> NAME/KEY: misc_feature
<222> LOCATION: (2)..(3)
<223> OTHER INFORMATION: apn intersubunit linkage
<220> FEATURE:
<221> NAME/KEY: misc_feature
<222> LOCATION: (8)..(9)
<223> OTHER INFORMATION: apn intersubunit linkage
<220> FEATURE:
<221> NAME/KEY: misc_feature
<222> LOCATION: (13)..(14)
<223> OTHER INFORMATION: apn intersubunit linkage
<220> FEATURE:
<221> NAME/KEY: misc_feature
<222> LOCATION: (19)..(20)
<223> OTHER INFORMATION: apn intersubunit linkage

<400> SEQUENCE: 37
gctaccactc acgtggtggt gatgg                                          25

<210> SEQ ID NO 38
<211> LENGTH: 25
<212> TYPE: DNA
<213> ORGANISM: Artificial Sequence
<220> FEATURE:
<223> OTHER INFORMATION: Exemplary HGPS Targeting Sequence
<220> FEATURE:
<221> NAME/KEY: misc_feature
<222> LOCATION: (3)..(4)
<223> OTHER INFORMATION: apn intersubunit linkage
<220> FEATURE:
<221> NAME/KEY: misc_feature
<222> LOCATION: (13)..(14)
<223> OTHER INFORMATION: apn intersubunit linkage
<220> FEATURE:
<221> NAME/KEY: misc_feature
<222> LOCATION: (18)..(19)
<223> OTHER INFORMATION: apn intersubunit linkage
<220> FEATURE:
<221> NAME/KEY: misc_feature
<222> LOCATION: (21)..(22)
<223> OTHER INFORMATION: apn intersubunit linkage

<400> SEQUENCE: 38
gggtccaccc acctgggctc ctgag                                          25

<210> SEQ ID NO 39

```
<211> LENGTH: 9
<212> TYPE: PRT
<213> ORGANISM: Artificial Sequence
<220> FEATURE:
<223> OTHER INFORMATION: Arginine-Rich Cell-Penetrating Peptide
      Transporter

<400> SEQUENCE: 39

Arg Arg Arg Gln Arg Arg Lys Lys Arg
1               5

<210> SEQ ID NO 40
<211> LENGTH: 9
<212> TYPE: PRT
<213> ORGANISM: Artificial Sequence
<220> FEATURE:
<223> OTHER INFORMATION: Arginine-Rich Cell-Penetrating Peptide
      Transporter

<400> SEQUENCE: 40

Arg Lys Lys Arg Arg Gln Arg Arg Arg
1               5

<210> SEQ ID NO 41
<211> LENGTH: 11
<212> TYPE: PRT
<213> ORGANISM: Artificial Sequence
<220> FEATURE:
<223> OTHER INFORMATION: Arginine-Rich Cell-Penetrating Peptide
      Transporter

<400> SEQUENCE: 41

Arg Arg Arg Arg Arg Arg Arg Arg Arg Phe Phe
1               5                   10

<210> SEQ ID NO 42
<211> LENGTH: 11
<212> TYPE: PRT
<213> ORGANISM: Artificial Sequence
<220> FEATURE:
<223> OTHER INFORMATION: Arginine-Rich Cell-Penetrating Peptide
      Transporter

<400> SEQUENCE: 42

Arg Arg Arg Arg Arg Phe Phe Arg Arg Arg Arg
1               5                   10

<210> SEQ ID NO 43
<211> LENGTH: 4
<212> TYPE: PRT
<213> ORGANISM: Artificial Sequence
<220> FEATURE:
<223> OTHER INFORMATION: Arginine-Rich Cell-Penetrating Peptide
      Transporters

<400> SEQUENCE: 43

Arg Arg Arg Arg
1

<210> SEQ ID NO 44
<211> LENGTH: 5
<212> TYPE: PRT
<213> ORGANISM: Artificial Sequence
<220> FEATURE:
<223> OTHER INFORMATION: Arginine-Rich Cell-Penetrating Peptide
      Transporter

<400> SEQUENCE: 44
```

```
Arg Arg Arg Arg Arg
1               5

<210> SEQ ID NO 45
<211> LENGTH: 6
<212> TYPE: PRT
<213> ORGANISM: Artificial Sequence
<220> FEATURE:
<223> OTHER INFORMATION: Arginine-Rich Cell-Penetrating Peptide
      Transporter

<400> SEQUENCE: 45

Arg Arg Arg Arg Arg Arg
1               5

<210> SEQ ID NO 46
<211> LENGTH: 7
<212> TYPE: PRT
<213> ORGANISM: Artificial Sequence
<220> FEATURE:
<223> OTHER INFORMATION: Arginine-Rich Cell-Penetrating Peptide
      Transporter

<400> SEQUENCE: 46

Arg Arg Arg Arg Arg Arg Arg
1               5

<210> SEQ ID NO 47
<211> LENGTH: 8
<212> TYPE: PRT
<213> ORGANISM: Artificial Sequence
<220> FEATURE:
<223> OTHER INFORMATION: Arginine-Rich Cell-Penetrating Peptide
      Transporter

<400> SEQUENCE: 47

Arg Arg Arg Arg Arg Arg Arg Arg
1               5

<210> SEQ ID NO 48
<211> LENGTH: 9
<212> TYPE: PRT
<213> ORGANISM: Artificial Sequence
<220> FEATURE:
<223> OTHER INFORMATION: Arginine-Rich Cell-Penetrating Peptide
      Transporter

<400> SEQUENCE: 48

Arg Arg Arg Arg Arg Arg Arg Arg Arg
1               5

<210> SEQ ID NO 49
<211> LENGTH: 16
<212> TYPE: PRT
<213> ORGANISM: Artificial Sequence
<220> FEATURE:
<223> OTHER INFORMATION: Arginine-Rich Cell-Penetrating Peptide
      Transporter
<220> FEATURE:
<221> NAME/KEY: MOD_RES
<222> LOCATION: (2)..(2)
<223> OTHER INFORMATION: Xaa = Acp
<220> FEATURE:
<221> NAME/KEY: MOD_RES
<222> LOCATION: (4)..(4)
<223> OTHER INFORMATION: Xaa = Acp
<220> FEATURE:
<221> NAME/KEY: MOD_RES
<222> LOCATION: (6)..(6)
<223> OTHER INFORMATION: Xaa = Acp
```

```
<220> FEATURE:
<221> NAME/KEY: MOD_RES
<222> LOCATION: (8)..(8)
<223> OTHER INFORMATION: Xaa = Acp
<220> FEATURE:
<221> NAME/KEY: MOD_RES
<222> LOCATION: (10)..(10)
<223> OTHER INFORMATION: Xaa = Acp
<220> FEATURE:
<221> NAME/KEY: MOD_RES
<222> LOCATION: (12)..(12)
<223> OTHER INFORMATION: Xaa - Acp
<220> FEATURE:
<221> NAME/KEY: MOD_RES
<222> LOCATION: (14)..(14)
<223> OTHER INFORMATION: Xaa = Acp
<220> FEATURE:
<221> NAME/KEY: MOD_RES
<222> LOCATION: (16)..(16)
<223> OTHER INFORMATION: Xaa = Acp

<400> SEQUENCE: 49

Arg Xaa Arg Xaa Arg Xaa Arg Xaa Arg Xaa Arg Xaa Arg Xaa Arg Xaa
1               5                   10                  15

<210> SEQ ID NO 50
<211> LENGTH: 12
<212> TYPE: PRT
<213> ORGANISM: Artificial Sequence
<220> FEATURE:
<223> OTHER INFORMATION: Arginine-Rich Cell-Penetrating Pepetide
      Transporter
<220> FEATURE:
<221> NAME/KEY: MOD_RES
<222> LOCATION: (2)..(2)
<223> OTHER INFORMATION: Xaa - 6-aminohexanoic acid
<220> FEATURE:
<221> NAME/KEY: MOD_RES
<222> LOCATION: (5)..(5)
<223> OTHER INFORMATION: Xaa = 6-aminohexanoic acid
<220> FEATURE:
<221> NAME/KEY: MOD_RES
<222> LOCATION: (8)..(8)
<223> OTHER INFORMATION: Xaa = 6-aminohexanoic acid
<220> FEATURE:
<221> NAME/KEY: MOD_RES
<222> LOCATION: (11)..(11)
<223> OTHER INFORMATION: Xaa = 6-aminohexanoic acid

<400> SEQUENCE: 50

Arg Xaa Arg Arg Xaa Arg Arg Xaa Arg Arg Xaa Arg
1               5                   10

<210> SEQ ID NO 51
<211> LENGTH: 15
<212> TYPE: PRT
<213> ORGANISM: Artificial Sequence
<220> FEATURE:
<223> OTHER INFORMATION: Arginine-Rich Cell-Penetrating Peptide
      Transporter
<220> FEATURE:
<221> NAME/KEY: MOD_RES
<222> LOCATION: (2)..(2)
<223> OTHER INFORMATION: Xaa = 6-aminohexanoic acid
<220> FEATURE:
<221> NAME/KEY: MOD_RES
<222> LOCATION: (5)..(5)
<223> OTHER INFORMATION: Xaa = 6-aminohexanoic acid
<220> FEATURE:
<221> NAME/KEY: MOD_RES
<222> LOCATION: (8)..(8)
<223> OTHER INFORMATION: Xaa = 6-aminohexanoic acid
<220> FEATURE:
<221> NAME/KEY: MOD_RES
<222> LOCATION: (11)..(11)
```

```
<223> OTHER INFORMATION: Xaa = 6-aminohexanoic acid
<220> FEATURE:
<221> NAME/KEY: MOD_RES
<222> LOCATION: (14)..(14)
<223> OTHER INFORMATION: Xaa = 6-aminohexanoic acid

<400> SEQUENCE: 51

Arg Xaa Arg Arg Xaa Arg Arg Xaa Arg Arg Xaa Arg Arg Xaa Arg
1               5                   10                  15

<210> SEQ ID NO 52
<211> LENGTH: 12
<212> TYPE: PRT
<213> ORGANISM: Artificial Sequence
<220> FEATURE:
<223> OTHER INFORMATION: Arginine-Rich Cell-Penetrating Peptide
      Transporter
<220> FEATURE:
<221> NAME/KEY: MOD_RES
<222> LOCATION: (2)..(2)
<223> OTHER INFORMATION: Xaa = 6-aminohexanoic acid
<220> FEATURE:
<221> NAME/KEY: MOD_RES
<222> LOCATION: (5)..(5)
<223> OTHER INFORMATION: Xaa = beta-alanine
<220> FEATURE:
<221> NAME/KEY: MOD_RES
<222> LOCATION: (8)..(8)
<223> OTHER INFORMATION: Xaa = 6-aminohexanoic acid
<220> FEATURE:
<221> NAME/KEY: MOD_RES
<222> LOCATION: (11)..(11)
<223> OTHER INFORMATION: Xaa = beta-alanine

<400> SEQUENCE: 52

Arg Xaa Arg Arg Xaa Arg Arg Xaa Arg Arg Xaa Arg
1               5                   10

<210> SEQ ID NO 53
<211> LENGTH: 15
<212> TYPE: PRT
<213> ORGANISM: Artificial Sequence
<220> FEATURE:
<223> OTHER INFORMATION: Arginine-Rich Cell-Penetrating Transporter

<400> SEQUENCE: 53

Arg Ala Arg Arg Ala Arg Arg Ala Arg Arg Ala Arg Phe Phe Cys
1               5                   10                  15

<210> SEQ ID NO 54
<211> LENGTH: 15
<212> TYPE: PRT
<213> ORGANISM: Artificial Sequence
<220> FEATURE:
<223> OTHER INFORMATION: Arginine-Rich Cell-Penetrating Peptide
      Transporter

<400> SEQUENCE: 54

Arg Gly Arg Arg Gly Arg Arg Gly Arg Arg Gly Arg Phe Phe Cys
1               5                   10                  15

<210> SEQ ID NO 55
<211> LENGTH: 20
<212> TYPE: DNA
<213> ORGANISM: Artificial Sequence
<220> FEATURE:
<223> OTHER INFORMATION: Forward primer

<400> SEQUENCE: 55
tctttgcagc cacattcccg                                              20
```

```
<210> SEQ ID NO 56
<211> LENGTH: 20
<212> TYPE: DNA
<213> ORGANISM: Artificial Sequence
<220> FEATURE:
<223> OTHER INFORMATION: Reverse primer

<400> SEQUENCE: 56
ggcttgcggg tgttaaaagc                                              20

<210> SEQ ID NO 57
<211> LENGTH: 22
<212> TYPE: DNA
<213> ORGANISM: Artificial Sequence
<220> FEATURE:
<223> OTHER INFORMATION: Forward primer

<400> SEQUENCE: 57
gcaacaagtc caatgaggac ca                                           22

<210> SEQ ID NO 58
<211> LENGTH: 30
<212> TYPE: DNA
<213> ORGANISM: Artificial Sequence
<220> FEATURE:
<223> OTHER INFORMATION: Primer sequence

<400> SEQUENCE: 58
catgatgctg cagttctggg ggctctggac                                   30

<210> SEQ ID NO 59
<211> LENGTH: 30
<212> TYPE: DNA
<213> ORGANISM: Artificial Sequence
<220> FEATURE:
<223> OTHER INFORMATION: Primer sequence

<400> SEQUENCE: 59
catgatgctg cagttctggg ggctctggat                                   30
```